United States Patent
Wu et al.

(10) Patent No.: US 7,253,169 B2
(45) Date of Patent: *Aug. 7, 2007

(54) AZA COMPOUNDS, PHARMACEUTICAL COMPOSITIONS AND METHODS OF USE

(75) Inventors: Yong-Qian Wu, Columbia, MD (US); Wei Huang, Wildwood, MO (US); Gregory S. Hamilton, Catonsville, MD (US)

(73) Assignee: Gliamed, Inc., New York, NY (US)

( * ) Notice: Subject to any disclaimer, the term of this patent is extended or adjusted under 35 U.S.C. 154(b) by 948 days.

This patent is subject to a terminal disclaimer.

(21) Appl. No.: 09/835,523

(22) Filed: Apr. 17, 2001

(65) Prior Publication Data

US 2002/0028814 A1    Mar. 7, 2002

Related U.S. Application Data

(63) Continuation-in-part of application No. 09/551,618, filed on Apr. 17, 2000, now Pat. No. 6,417,189.

(60) Provisional application No. 60/164,950, filed on Nov. 12, 1999.

(51) Int. Cl.
```
A61K 31/50     (2006.01)
A61K 31/501    (2006.01)
A61K 31/551    (2006.01)
A61K 31/675    (2006.01)
C07D 413/02    (2006.01)
C07D 43/02     (2006.01)
```
(52) U.S. Cl. ............ 514/252.05; 514/85; 514/92; 514/218; 514/249; 514/364; 514/365; 514/383; 514/397; 514/407; 544/232; 544/238; 544/239; 548/131; 548/266.2; 548/312.4; 548/365.1; 548/366.1; 540/553

(58) Field of Classification Search ................
514/252.01–252.06, 218, 406, 407, 403, 514/341, 247, 249, 85, 92, 364, 365, 383, 514/397; 540/553; 544/238, 239, 232; 548/356.1, 548/364.1–364.7, 266.2, 131, 312.4, 365.1, 548/366.1; 546/275.4

See application file for complete search history.

(56) References Cited

U.S. PATENT DOCUMENTS

| | | | |
|---|---|---|---|
| 3,706,743 A | 12/1972 | Moon | 260/250 |
| 4,399,136 A | 8/1983 | Hassall et al. | 424/250 |
| 4,431,644 A | 2/1984 | Smith et al. | 424/246 |
| 4,561,880 A | 12/1985 | Shimano et al. | 71/92 |
| 4,581,220 A | 4/1986 | Nelson et al. | 423/658.5 |
| 4,593,094 A | 6/1986 | Nagano et al. | 544/224 |
| 4,659,711 A | 4/1987 | Huang et al. | 514/247 |
| 4,743,687 A | 5/1988 | Lawton et al. | 540/487 |
| 4,766,110 A | 8/1988 | Ryan et al. | 514/19 |
| 4,801,706 A | 1/1989 | Winkley et al. | |
| 5,002,964 A | 3/1991 | Loscalzo | 514/423 |
| 5,034,051 A | 7/1991 | Kume et al. | 71/92 |
| 5,109,014 A * | 4/1992 | Jacobson | 514/403 |
| 5,128,483 A | 7/1992 | Trybulski | 548/531 |
| 5,149,872 A | 9/1992 | Messina et al. | 564/151 |
| 5,166,317 A | 11/1992 | Wallace et al. | 530/350 |
| 5,192,773 A | 3/1993 | Armistead et al. | 514/315 |
| 5,214,034 A | 5/1993 | Nakayama et al. | 514/159 |
| 5,215,969 A | 6/1993 | Springer et al. | 514/21 |
| 5,232,923 A | 8/1993 | Fukazawa et al. | 514/237.5 |
| 5,256,670 A * | 10/1993 | Jacobson | 514/304 |
| 5,310,738 A | 5/1994 | Nakayama | 544/224 |
| 5,321,009 A | 6/1994 | Baeder et al. | 514/4 |
| 5,330,993 A | 7/1994 | Armistead et al. | 514/330 |
| 5,342,942 A | 8/1994 | Jaen et al. | 544/250 |
| 5,359,138 A | 10/1994 | Takeuchi et al. | 562/567 |
| 5,399,565 A | 3/1995 | Greenwood et al. | |
| 5,453,437 A | 9/1995 | Schohe et al. | 514/424 |
| 5,504,197 A | 4/1996 | Schubert et al. | 536/23.5 |
| 5,506,243 A | 4/1996 | Ando et al. | 514/345 |
| 5,516,797 A | 5/1996 | Armistead et al. | 514/548 |
| 5,527,907 A | 6/1996 | Or et al. | 540/456 |
| 5,536,737 A | 7/1996 | Kobayashi et al. | 514/365 |
| 5,541,189 A | 7/1996 | Luly et al. | 514/291 |
| 5,543,423 A | 8/1996 | Zelle et al. | 514/332 |
| 5,614,547 A | 3/1997 | Hamilton et al. | 514/423 |
| 5,620,971 A | 4/1997 | Armistead et al. | 514/212 |
| 5,629,325 A | 5/1997 | Lin et al. | 514/318 |
| 5,643,908 A * | 7/1997 | Sugimura et al. | 514/247 |
| 5,665,774 A | 9/1997 | Armistead et al. | 514/533 |
| 5,670,503 A | 9/1997 | Kawai et al. | |
| 5,684,151 A | 11/1997 | Combs | 544/224 |
| 5,696,135 A | 12/1997 | Steiner et al. | 514/317 |
| 5,703,088 A | 12/1997 | Sharpe et al. | 514/278 |

(Continued)

FOREIGN PATENT DOCUMENTS

| | | |
|---|---|---|
| CA | 2271837 A1 | 11/1999 |
| DE | 3636278 | 10/1986 |
| DE | 197 42 263 | 9/1997 |
| EP | 0 104 484 A1 | 4/1984 |

(Continued)

OTHER PUBLICATIONS

Zouikri, Chemical Abstracts, vol. 129:216907, 1998.
Didierjean, Chemical Abstracts, vol. 128:137758, 1997.
Senoo, Chemical Abstracts, vol. 125:295188, 1996.
Bock, Chemical Abstracts, vol. 123:340467, 1995.

(Continued)

*Primary Examiner*—James O. Wilson
*Assistant Examiner*—Tamthorn N. Truong

(57) ABSTRACT

The present invention relates to N-substituted cyclic aza compounds, pharmaceutical compositions comprising such compounds, and methods of their use for effecting neuronal activities.

9 Claims, No Drawings

U.S. PATENT DOCUMENTS

| | | | |
|---|---|---|---|
| 5,714,485 A | 2/1998 | Lumma et al. | 514/247 |
| 5,714,510 A | 2/1998 | Proctor | 514/423 |
| 5,717,092 A | 2/1998 | Armistead et al. | 544/129 |
| 5,721,256 A | 2/1998 | Hamilton et al. | 514/330 |
| 5,744,485 A | 4/1998 | Zelle et al. | 514/318 |
| 5,750,690 A | 5/1998 | Broger et al. | 544/234 |
| 5,780,484 A | 7/1998 | Zelle et al. | 514/316 |
| 5,786,378 A | 7/1998 | Hamilton et al. | 514/423 |
| 5,795,908 A | 8/1998 | Hamilton et al. | 514/423 |
| 5,798,355 A | 8/1998 | Steiner et al. | 514/248 |
| 5,801,187 A | 9/1998 | Li et al. | 514/365 |
| 5,801,197 A | 9/1998 | Steiner et al. | 514/548 |
| 5,811,434 A | 9/1998 | Zelle | 514/307 |
| 5,840,736 A | 11/1998 | Zelle | 514/332 |
| 5,843,960 A | 12/1998 | Steiner et al. | 514/317 |
| 5,846,979 A | 12/1998 | Hamilton et al. | 514/311 |
| 5,846,981 A | 12/1998 | Steiner et al. | 514/317 |
| 5,859,031 A | 1/1999 | Hamilton et al. | 514/343 |
| 5,874,449 A | 2/1999 | Hamilton et al. | 514/330 |
| 5,898,029 A | 4/1999 | Lyons et al. | 514/12 |
| 5,935,989 A | 8/1999 | Hamilton et al. | 514/423 |
| 5,958,949 A | 9/1999 | Hamilton et al. | 514/318 |
| 5,968,957 A | 10/1999 | Hamilton et al. | 514/343 |
| 5,990,131 A | 11/1999 | Hamilton et al. | 514/330 |
| 6,022,878 A | 2/2000 | Steiner et al. | 514/317 |
| 6,037,370 A | 3/2000 | Armistead | 514/533 |
| 6,054,452 A | 4/2000 | Hamilton et al. | 514/212 |
| 6,069,163 A * | 5/2000 | Delaszlo | 514/247 |
| 6,417,189 B1 * | 7/2002 | Wu et al. | 514/252.01 |

FOREIGN PATENT DOCUMENTS

| | | | |
|---|---|---|---|
| EP | 104484 | * | 4/1984 |
| EP | 405994 | | 1/1991 |
| EP | 443983 | | 8/1991 |
| EP | 0 450 757 A2 | | 10/1991 |
| EP | 476933 | | 3/1992 |
| EP | 488 258 | | 6/1992 |
| EP | 572365 | * | 12/1993 |
| EP | 0 778 023 A1 | | 6/1997 |
| EP | 805 147 | | 11/1997 |
| WO | WO 88/09789 | | 12/1988 |
| WO | WO 89/06535 A1 | | 7/1989 |
| WO | WO 92/00278 | | 1/1992 |
| WO | WO 92/04370 | | 3/1992 |
| WO | WO 92/11245 | | 7/1992 |
| WO | WO 92/11850 | | 7/1992 |
| WO | WO 92/19593 | | 11/1992 |
| WO | WO 92/21313 | | 12/1992 |
| WO | WO 93/13066 | | 7/1993 |
| WO | WO 93/14072 | | 7/1993 |
| WO | WO 94/12474 | | 6/1994 |
| WO | WO 94/15900 | | 7/1994 |
| WO | WO 94/19350 A1 | | 9/1994 |
| WO | WO 95/35308 | | 12/1995 |
| WO | WO 95/35367 | | 12/1995 |
| WO | WO 96/05180 A1 | | 2/1996 |
| WO | WO 96/06846 | | 3/1996 |
| WO | WO 96/20725 | | 11/1996 |
| WO | WO 96/20949 | | 11/1996 |
| WO | WO 96/40140 | | 12/1996 |
| WO | WO 96/40633 | | 12/1996 |
| WO | WO 96/41609 | | 12/1996 |
| WO | WO 97/23202 | | 3/1997 |
| WO | WO 97/23458 | | 3/1997 |
| WO | WO 97/36869 | | 9/1997 |
| WO | WO 97/38008 | | 10/1997 |
| WO | WO 97/20554 | | 12/1997 |
| WO | WO 97/48681 | | 12/1997 |
| WO | WO 97/49695 | | 12/1997 |
| WO | WO 98/05333 A1 | | 2/1998 |
| WO | WO 98/13343 | | 2/1998 |
| WO | WO 98/08814 | | 3/1998 |
| WO | WO 98/08827 | | 3/1998 |
| WO | WO 98/37885 | | 3/1998 |
| WO | WO 98/20891 | | 5/1998 |
| WO | WO 98/20892 | | 5/1998 |
| WO | WO 98/20893 | | 5/1998 |
| WO | WO 98/29117 | | 9/1998 |
| WO | WO 98/55091 | | 10/1998 |
| WO | WO 98/24805 | | 11/1998 |
| WO | WO 99/10340 | | 3/1999 |
| WO | WO 99/20272 A1 | | 4/1999 |
| WO | WO 99/46248 A1 | | 9/1999 |
| WO | WO 01/02362 | | 1/2001 |

OTHER PUBLICATIONS

Kao, Chemical Abstracts, vol. 123:83100, 1995.
Didierjean, Chemical Abstracts, vol. 124:146778, 1995.
Pinnen, Chemical Abstracts, vol. 121:301283, 1994.
Casini, Chemical Abstracts, vol. 120:270095, 1993.
Brunner, Chemical Abstracts, vol. 119:95312, 1993.
Lecoq, Chemical Abstracts, vol. 119:181221, 1993.
Bock, Chemical Abstracts, vol. 117:111477, 1992.
Hosoda, Chemical Abstracts, vol. 118:255342, 1992.
Pissiotas, Chemical Abstracts, vol. 116:214522, 1992.
Lecoq, Chemical Abstracts, vol. 118:39364, 1992.
Sato, Chemical Abstracts, vol. 117:145248, 1992.
Kume, Chemical Abstracts, vol. 91:106452, 1991.
Onodera, Chemical Abstracts, vol. 116:20783, 1991.
Kume, Chemical Abstracts, vol. 113:211999, 1990.
Kume, Chemical Abstracts, vol. 90:13073, 1990.
Henke, Chemical Abstracts, vol. 112:179895, 1989.
Kume, Chemical Abstracts, vol. 110:173245, 1988.
Hagiwara, Chemical Abstracts, vol. 109:110447, 1988.
Haga, Chemical Abstracts, vol. 108:94578, 1987.
Haga, Chemical Abstracts, vol. 105:20519, 1986.
Nagano, Chemical Abstracts, vol. 86:63224, 1986.
Haga, Chemical Abstracts, vol. 86:60572, 1986.
Nagano, Chemical Abstracts, vol. 86:32884, 1986.
Sumitomo, Chemical Abstracts, vol. 102:132057, 1984.
Kobayashi, Chemical Abstracts, vol. 101:191944, 1984.
Nagano, Chemical Abstracts, vol. 84:31794, 1984.
Nagano, Chemical Abstracts, vol. 99:194984, 1983.
Kornet, Chemical Abstracts, vol. 95:62107, 1981.
Dutta, Chemical Abstracts, vol. 89:191427, 1978.
Wakabayashi, Chemical Abstracts, vol. 88:50904, 1977.
Wakabayashi, Chemical Abstracts, vol. 86:29859, 1976.
Wakabayashi, Chemical Abstracts, vol. 85:473445, 1976.
Dutta, Chemical Abstracts, vol. 83:193683, 1975.
Zinner, Chemical Abstracts, vol. 58:4577c, 1962.
Luttringhaus, Chemical Abstracts, vol. 54:4606h, 1959.
Rink, Chemical Abstracts, vol. 54:560d, 1959.
Gudasheva, T.A. et al., "Synthesis and antiamnesic activity of a series of N-acylprolyl-containing dipeptides," *Eur. J. Med. Chem.*, 1996, 31, 151-157.
Dawson, T. et al., "Immunosuppressant FK506 enhances phosphorylation of nitric oxide synthase and protects against glutamate neurotoxicity," *Proc. Natl. Acad. Sci. USA*, 1993, 90, 9808-9812.
Dawson, T. et al., "The immunophilins, FK506 binding protein and cyclophilin, are discretely localized in the brain: relationship to calcineurin," *Neuroscience*, 1994, 62, 569-580.
Gold, B. et al., "Regulation of the Transcription Factor c-JUN by nerve growth factor in adult sensory neurons," *Neuroscience Letters*, 1993, 154, 129-133.
Gold, B. et al., "Regulation of aberrant neurofilament phosphorylation in neuronal perikarya. IV. Evidence for the involvement of two signals," *Brain Research*, 1993, 626, 23-30.
Gold, B. et al., "the immunosuppressant FK506 increases functional recovery and nerve regeneration following peripheral nerve injury," *Restorative Neurology and Neuroscience*, 1994, 6, 287-296.

Gold, B. et al., "Multiple signals underlie the axotomy-induced up-regulation of c-JUN in adult sensory neurons," *Neuroscience Letters,* 1994, 176, 123-127.

Gold, B. et al., The immunosuppressant FK506 increases the rate of axonal regeneration in rat sciatic nerves *J., Neuroscience,* 1995, 15, 7509-7516.

Hamilton, G. et al., "Neuroimmunophilin Ligands as Novel Therapeutics for the Treatment of Degenerative Disorders of the Nervous System," 1-71.

Kitamura et al., "Suppressive Effect of FK-506, a Novel Immunosuppressant, Against MPTP-Induced Dopamine Depletion in the Striatum of Young C57BL/6 Mice," *J. Neuroimmunology,* 1994, 50, 221-224.

Lyons, W. E. et al., "Immunosuppressant FK506 promotes neurite outgrowth in cultures of PC 12 cells and sensory ganglia," *Proc. Natl. Acad. Sci. USA,* 1994, 91, 3191-3195.

Lyons, W. E. et al., "Neuronal Regeneration Enhances the Expression of the Immunophilin FKBP-12," *J. Neuroscience,* 1995, 15(4), 2985-2994.

Ryba et al., "Cyclosporine A Prevents Neurological Deterioration of Patients with SAH—A Preliminary Report," *Acta Neurochirurgica,* 1991, 112, 25-27.

Shiga et al., "Cyclosporin A Protects Against Ischemia-Reperfusion Injury in the Brain," *Brain Research,* 1992, 595, 145-148.

Snyder, S. et al., "Immunophilins and the Nervous Systems", *Nature Medicine,* 1995, 1, 32-37.

Steiner, J. et al., "High brain densities of the immunophilin FKBP colocalized with calcineurin," *Nature,* 1992, 358, 584-587.

Steiner, J. et al., "Nonimmunosuppressive ligands for neuroimmunophilins promote nerve extension in vitro and in vivo," *Society for Neuroscience Abstracts,* 1996, 22, 297.13.

Steiner, J. et al., "Neurotrophic immunophilin ligands stimulate structural and functional recovery in neurodegenerative animal models," *Proc. Natl. Acad. Sci. USA,* 1997, 94, 2019-2024.

Steiner, J. et al., "Neurotrophic actions of nonimmunosuppressive analogues of immunosuppressive drugs FK506, rapamycin and cyclosporin A," *Nature Medicine,* 1997, 421-428.

Teichner et al., "Treatment with Cyclosporine A Promotes Axonal Regneration in Rats Submitted to Transverse Section of the Spinal Cord," *Int'l J. Brain Research & Neurobio.,* 1993, 34(3), 343-349.

Kozikowski, A.P. et al., "Alzheimer's Therapy: An Approach to Novel Muscarinic Ligands Based Upon the Naturally Occurring Alkaloid Himbacine," *Bioorg & Med. Chem. Lett.,* 1992, 2, 797-802.

Nicolaides, E.D. et al., "Modified Di- and Tripeptions of the C-Terminal Portion of Oxytocin and Vasopressin as Possible Cognition Activation Agents," *J. Med. Chem.* 1986, 29, 959-971.

DeRuiter, Jack et al., "In Vitro Aldose Reductase Inhibitory Activity of Substituted N-Benzenesulfonyl-glycine Derivatives," *J. Pharm. Sci.,* 1987, 76(2), 149-152.

Caufield, C. et al., "Macrocyclic Immunomodulators," *Ann. Rep. Med. Chem.,* 1989, 195-204.

Baldwin et al., "Pyrazolotriazines: a new class of tumour-inhibitory agents," J. Pharm vol. 18, pp. 1S-4S (May 2, 1966).

Borloo et al., "Synthesis and evaluation of azaproline peptides as potential inhibitors of dipeptidyl peptidase IV and prolyl oligopeptidase," Letters in Peptide Science, vol. 2, pp. 198-202 (1995).

Steiner et al., "Neurotrophic actions of nonimmunosuppresive analogues of immunosuppressive drugs FK506, rapamycin and cyclosporin A," Nature Medicine, vol. 3, No. 4, pp. 421-428 (Apr. 1997).

US 5,654,332, 08/1997, Armistead (withdrawn)

* cited by examiner

AZA COMPOUNDS, PHARMACEUTICAL COMPOSITIONS AND METHODS OF USE

This application is a Continuation-in-Part of U.S. patent application Ser. No. 09/551,618, filed Apr. 17, 2000 now U.S. Pat. No. 6,417,189, which claims the benefit of U.S. Provisional Application No. 60/164,950 filed Nov. 12, 1999.

BACKGROUND OF THE INVENTION

1. Field of Invention

The present invention relates generally to N-substituted cyclic aza compounds, pharmaceutical compositions comprising such compounds, and their preparation and use for preventing and/or treating neurological disorders; for treating alopecia and promoting hair growth; for treating vision disorders and/or improving vision; for treating memory impairment and/or enhancing memory performance; and for preventing or treating hearing loss in an animal.

2. Description of Related Art

It has been found that picomolar concentrations of an immunosuppressant such as FK506 and rapamycin stimulate neurite outgrowth in PC12 cells and sensory nervous, namely dorsal root ganglion cells (DRGs). Lyons et al., *Proc. Of Natl. Acad. Sci.*, 1994 vol. 91, pp. 3191-3195. In whole animal experiments, FK506 has been shown to stimulate nerve regeneration following facial nerve injury and results in functional recovery in animals with sciatic nerve lesions.

Several neurotrophic factors effecting specific neuronal populations in the central nervous system have been identified. For example, it has been hypothesized that Alzheimer's disease results from a decrease or loss of nerve growth factor (NGF). It has thus been proposed to treat Alzheimer's patients with exogenous nerve growth factor or other neurotrophic proteins such as brain derived nerve factor (BDNF) glial derived nerve factor, ciliary neurotrophic factor, and neurotropin-3 to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressants exhibit a number of potentially serious side effects including nephrotoxicity, such as impairment of glomerular filtration and irreversible interstitial fibrosis (Kopp et al., 1991, *J. Am. Soc. Nephrol.* 1:162); neurological deficits, such as involuntary tremors, or non-specific cerebral angina such as non-localized headaches (De Groen et al., 1987, *N. Engl. J. Med.* 317:861); and vascular hypertension with complications resulting therefrom (Kahan et al., 1989 *N. Engl. J. Med.* 321: 1725).

Accordingly, there is a need for non-immunosuppressive, small-molecule compounds which are useful for neurotrophic effects and for treating neurodegenerative disorders.

Hair loss occurs in a variety of situations. These situations include male pattern alopecia, alopecia senilis, alopecia areata, diseases accompanied by basic skin lesions or tumors, and systematic disorders such as nutritional disorders and internal secretion disorders. The mechanisms causing hair loss are very complicated, but in some instances can be attributed to aging, genetic disposition, the activation of male hormones, the loss of blood supply to hair follicles, and scalp abnormalities.

The immunosuppressant drugs FK506, rapamycin and cyclosporin are well known as potent T-cell specific immunosuppressants, and are effective against graft rejection after organ transplantation. It has been reported that topical, but not oral, application of FK506 (Yamamoto et al., *J. Invest. Dermatol.*, 1994, 102, 160-164; Jiang et al., *J. Invest. Dermatol.* 1995, 104, 523-525) and cyclosporin (Iwabuchi et al., *J. Dermatol. Sci.* 1995, 9, 64-69) stimulates hair growth in a dose-dependent manner. One form of hair loss, alopecia areata, is known to be associated with autoimmune activities; hence, topically administered immunomodulatory compounds are expected to demonstrate efficacy for treating that type of hair loss. The hair growth stimulating effects of FK506 have been the subject of an international patent filing covering FK506 and structures related thereto for hair growth stimulation (Honbo et al., EP 0 423 714 A2). Honbo et al. discloses the use of relatively large tricyclic compounds, known for their immunosuppressive effects, as hair revitalizing agents.

The hair growth and revitalization effects of FK506 and related agents are disclosed in many U.S. patents (Goulet et al., U.S. Pat. No. 5,258,389; Luly et al., U.S. Pat. No. 5,457,111; Goulet et al., U.S. Pat. No. 5,532,248; Goulet et al., U.S. Pat. No. 5,189,042; and Ok et al., U.S. Pat. No. 5,208,241; Rupprecht et al., U.S. Pat. No. 5,284,840; Organ et al., U.S. Pat. No. 5,284,877). These patents claim FK506 related compounds. Although they do not claim methods of hair revitalization, they disclose the known use of FK506 for effecting hair growth. Similar to FK506 (and the claimed variations in the Honbo et al. patent), the compounds claimed in these patents are relatively large. Further, the cited patents relate to immunomodulatory compounds for use in autoimmune related diseases, for which FK506's efficacy is well known.

Other U.S. patents disclose the use of cyclosporin and related compounds for hair revitalization (Hauer et al., U.S. Pat. No. 5,342,625; Eberle, U.S. Pat. No. 5,284,826; Hewitt et al., U.S. Pat. No. 4,996,193). These patents also relate to compounds useful for treating autoimmune diseases and cite the known use of cyclosporin and related immunosuppressive compounds for hair growth.

However, immunosuppressive compounds by definition suppress the immune system and also exhibit other toxic side effects. Accordingly, there is a need for non-immunosuppressive, small molecule compounds which are useful as hair revitalizing compounds.

The visual system is composed of the eyes, ocular adnexa and the visual pathways. Dysfunction of the visual system may lead to permanent or temporary visual impairment, i.e. a deviation from normal in one or more functions of the eye. Visual impairment manifests itself in various ways and includes a broad range of visual dysfunctions and disturbances. Without limitation, these dysfunctions and disturbances include partial or total loss of vision, the need for correction of visual acuity for objects near and far, loss of visual field, impaired ocular motility without diplopia (double vision), impaired or skewed color perception, limited adaptation to light and dark, diminished accommodation, metamorphopsic distortion, impaired binocular vision, paresis of accommodation, iridoplegia, entropion, ectropion, epiphora, lagophthalmos, and scarring. See *Physicians' Desk Reference (PDR) for Ophthalmology*, 16th Edition, 6:47 (1988). The visual system may be adversely affected by various ophthalmologic disorders, diseases, injuries, and complications, including, without limitation, genetic disorders; disorders associated with aging or degenerative diseases; disorders correlating to physical injury to the eye, head, or other parts of the body resulting from external forces; disorders resulting from environmental factors; disorders resulting from a broad range of diseases; and combinations of any of the above.

The visual system is a complex system composed of numerous components. Visual impairment can involve the entire visual system, any one component, or any combination of components, depending upon the precise nature of the circumstances. The eye is composed of a lens, which is suspended in the zonules of Zinn and is focused by the ciliary body. The ciliary body also secretes aqueous humor, which fills the posterior chamber, passes through the pupil into the anterior chamber, then drains primarily via the canal of Schlemm. The iris regulates the quantity of light entering the eye by adjusting the size of its central opening, the pupil. A visual image is focused onto the retina, the fovea centralis being the retinal area of sharpest visual acuity. The conjunctiva is the mucus membrane which lines the eyelids and the eyeball, and ends abruptly at the limbus conjunctivae, the edge of the conjunctiva overlapping the cornea. The cornea is the clear, transparent anterior portion of the fibrous coat of the eye; it is important in light refraction and is covered with an epithelium that differs in many respects from the conjunctival epithelium.

The retina is the innermost, light sensitive portion of the eye, containing two types of photoreceptors, cones, which are responsible for color vision in brighter light, and rods, which are essential for vision in dim light but do not perceive colors. After light passes through the cornea, lens system, and the vitreous humor, it enters the retina from the inside; that is, it passes through the ganglion cells and nerve fibers, the inner and outer plexiform layers, the inner and outer nuclear layers, and the internal and external limiting membranes before it finally reaches the layer of photoreceptors located near the outside of the retina, just inside the outermost pigment epithelium layer. The cells of the pigment epithelium layer act as an anatomical barrier to liquids and substances located outside of the eye, forming the "blood-retina" barrier, and provide nourishment, oxygen, a source of functionally useful substances like vitamin A, and phagocytosis of decomposition products to photoreceptor cells. There is no anatomical connection between the pigment epithelium and the photoreceptor layer, permitting separation of the layers in some pathological situations.

When rods or cones are excited by light, signals are transmitted through successive neurons in the retina itself, into the optic nerve fibers, and ultimately to the cerebral cortex. Both rods and cones contain molecules that decompose on exposure to light and, in the process, excite the nerve fibers leading from the eye. The molecule in rods is rhodopsin. The three light-sensitive molecules in cones, collectively called iodopsin, have compositions only slightly different from that of rhodopsin and are maximally excited by red, blue, or green light, respectively.

Neither rods nor cones generate action potentials. Rather, the light-induced membrane hyperpolarization generated in the outer, photosensitive segment of a rod or cone cell is transmitted from the outer segment through the inner segment to the synaptic body by direct conduction of the electrical voltage itself, a process called electrotonic conduction. At the synaptic body, the membrane potential controls the release of an unknown transmitter molecule. In low light, rod and cone cell membranes are depolarized and the rate of transmitter release is greatest. Light-induced hyperpolarization causes a marked decrease in the release of transmitter molecules.

The transmitters released by rod and cone cells induce signals in the bipolar neurons and horizontal cells. The signals in both these cells are also transmitted by electrotonic conduction and not by action potential.

The rod bipolar neurons connect with as many as 50 rod cells, while the dwarf and diffuse bipolar cells connect with one or several cone cells. A depolarizing bipolar cell is stimulated when its connecting rods or cones are exposed to light. The release of transmitter molecules inhibits the depolarizing bipolar cell. Therefore, in the dark, when the rods and cones are secreting large quantities of transmitter molecules, the depolarizing bipolar cells are inhibited. In the light, the decrease in release of transmitter molecules from the rods and cones reduces the inhibition of the bipolar cell, allowing it to become excited. In this manner, both positive and negative signals can be transmitted through different bipolar cells from the rods and cones to the amacrine and ganglion cells.

As their name suggests, horizontal cells project horizontally in the retina, where they may synapse with rods, cones, other horizontal cells, or a combination of cells types. The function of horizontal cells is unclear, although some mechanism in the convergence of photoreceptor signaling has been postulated.

All types of bipolar cells connect with ganglion cells, which are of two primary types. A-type ganglion cells predominately connect with rod bipolar cells, while B-type ganglion cells predominately connect with dwarf and diffuse bipolar cells. It appears that A-type ganglion cells are sensitive to contrast, light intensity, and perception of movement, while B-type ganglion cells appear more concerned with color vision and visual acuity.

Like horizontal cells, the Amacrine cells horizontally synapse with several to many other cells, in this case bipolar cells, ganglion cells, and other Amacrine cells. The function of Amacrine cells is also unclear.

The axons of ganglion cells carry signals into the nerve fiber layer of the eye, where the axons converge into fibers which further converge at the optic disc, where they exit the eye as the optic nerve. The ganglion cells transmit their signals through the optic nerve fibers to the brain in the form of action potentials. These cells, even when unstimulated, transmit continuous nerve impulses at an average, baseline rate of about 5 per second. The visual signal is superimposed onto this baseline level of ganglion cell stimulation. It can be either an excitatory signal, with the number of impulses increasing above the baseline rate, or an inhibitory signal, with the number of nerve impulses decreasing below the baseline rate.

As part of the central nervous system, the eye is in some ways an extension of the brain; as such, it has a limited capacity for regeneration. This limited regeneration capacity further complicates the challenging task of improving vision, resolving dysfunction of the visual system, and/or treating or preventing ophthalmologic disorders. Many disorders of the eye, such as retinal photic injury, retinal ischemia-induced eye injury, age-related macular degeneration, free radical-induced eye diseases, as well as numerous other disorders, are considered to be entirely untreatable. Other ophthalmologic disorders, e.g., disorders causing permanent visual impairment, are corrected only by the use of ophthalmic devices and/or surgery, with varying degrees of success.

The immunosuppressant drugs FK506, rapamycin, and cyclosporin are well known as potent T-cell specific immunosuppressants, and are effective against autoimmunity, transplant or graft rejection, inflammation, allergic responses, other autoimmune or immune-mediated diseases, and infectious diseases. It has been disclosed that application of Cyclosporin, FK-506, Rapamycin, Buspirone, Spiperone, and/or their derivatives are effective in treating some ophthalmologic disorders of these types. Several ophthalmologic disorders or vision problems are known to be associated with autoimmune and immunologically-mediated activities; hence, immunomodulatory compounds are expected to demonstrate efficacy for treating those types of ophthalmologic disorders or vision problems.

The effects of FK506, Rapamycin, and related agents in the treatment of ophthalmologic diseases are disclosed in several U.S. patents (Goulet et al., U.S. Pat. No. 5,532,248; Mochizuki et al., U.S. Pat. No. 5,514,686; Luly et al., U.S. Pat. No. 5,457,111; Russo et al., U.S. Pat. No. 5,441,937; Kulkarni, U.S. Pat. No. 5,387,589; Asakura et al., U.S. Pat. No. 5,368,865; Goulet et al., U.S. Pat. No. 5,258,389; Armistead et al., U.S. Pat. No. 5,192,773; Goulet et al., U.S. Pat. No. 5,189,042; and Fehr, U.S. Pat. No. 5,011,844). These patents claim FK506 or Rapamycin related compounds and disclose the known use of FK506 or Rapamycin related compounds in the treatment of ophthalmologic disorders in association with the known immunosuppressive effects of FK506 and Rapamycin. The compounds disclosed in these patents are relatively large. Further, the cited patents relate to immunomodulatory compounds limited to treating autoimmunity or related diseases, or immunologically-mediated diseases, for which the efficacy of FK506 and Rapamycin is well known.

Other U.S. patents disclose the use of cyclosporin, Spiperone, Buspirone, their derivatives, and other immunosuppressive compounds for use in the treatment of ophthalmologic diseases (Sharpe et al., U.S. Pat. No. 5,703,088; Sharpe et al., U.S. Pat. No. 5,693,645; Sullivan, U.S. Pat. No. 5,688,765; Sullivan, U.S. Pat. No. 5,620,921; Sharpe et al., U.S. Pat. No. 5,574,041; Eberle, U.S. Pat. No. 5,284,826; Sharpe et al., U.S. Pat. No. 5,244,902; Chiou et al., U.S. Pat. Nos. 5,198,454 and 5,194,434; and Kaswan, U.S. Pat. No. 4,839,342). These patents also relate to compounds useful for treating autoimmune diseases and cite the known use of cyclosporin, Spiperone, Buspirone, their derivatives, and other immunosuppressive compounds in treating ocular inflammation and other immunologically-mediated ophthalmologic diseases.

The immunosuppressive compounds disclosed in the prior art suppress the immune system, by definition, and also exhibit other toxic side effects. Accordingly, there is a need for non-immunosuppressant, small molecule compounds, and compositions and methods for use of such compounds, that are useful in improving vision; preventing, treating, and/or repairing visual impairment or dysfunction of the visual system; and preventing, treating, and/or resolving ophthalmologic disorders.

There are also a number of patents on non-immunosuppressive compounds disclosing methods of use for permitting or promoting wound healing (whether from injury or surgery); controlling intraocular pressure (often resulting from glaucoma); controlling neurodegenerative eye disorders, including damage or injury to retinal neurons, damage or injury to retinal ganglion cells, and macular degeneration; stimulating neurite outgrowth; preventing or reducing oxidative damage caused by free radicals; and treating impaired oxygen and nutrient supply, as well as impaired waste product removal, resulting from low blood flow. These non-immunosuppressive substances fall into one of two general categories: naturally occurring molecules, such as proteins, glycoproteins, peptides, hormones, and growth factors; and synthetic molecules.

Within the group of naturally occurring non-immunosuppressive molecules, several hormones, growth factors, and signaling molecules have been patented for use as supplements to naturally occurring quantities of such molecules, as well as for targeting of specific cells where the particular molecule does not naturally occur in a mature individual. These patents generally claim methods of use for reducing or preventing the symptoms of ocular disease, or arresting or reversing vision loss.

Specifically, Louis et al., U.S. Pat. Nos. 5,736,516 and 5,641,749, disclose the use of a glial cell line derived neurotrophic factor (GDNF) to stop or reverse the degeneration of retinal neurons (i.e. photoreceptors) and retinal ganglion cells caused by glaucoma, or other degenerative or traumatic retinal diseases or injuries. O'Brien, et al., U.S. Pat. Nos. 5,714,459 and 5,700,909, disclose the use of a glycoprotein, Saposin, and its derivatives for stimulating neurite outgrowth and increasing myelination. To stop or reverse degeneration of retinal neurons, LaVail et al., U.S. Pat. No. 5,667,968, discloses the use of a variety of neurotrophic proteins, including brain-derived neurotrophic factor, ciliary neurotrophic factor, neurotrophin-3 or neurotrophin-4, acidic or basic fibroblast growth factors, interleukin, tumor necrosis factor-α, insulin-like growth factor-2 and other growth factors. Wong et al., U.S. Pat. No. 5,632,984, discloses the use of interferons, especially interferon α-2a, for treating the symptoms of macular degeneration by reducing hemorrhage and limiting neovascularization. Finally, Wallace et al., U.S. Pat. No. 5,441,937, discloses the use of a lung-derived neurotrophic factor (NTF) to maintain the functionality of ciliary ganglion and parasympathetic neuron cells.

A key characteristic of factors derived from specific cell lines is their localization to specific cell lines or tissues; systemic treatment with these molecules would run a substantial risk of unintended, and potentially dangerous, effects in cell lines where the genes encoding these molecules are inactive. Similarly, hormones and growth factors often activate a large number of genes in many cell lines; again, non-localized application of these molecules would run a substantial risk of provoking an inappropriate, and potentially dangerous, response.

Within the category of synthetic molecules, most of the patented compounds are immunosuppressive and disclose uses in treating inflammatory, autoimmune, and allergic responses, as discussed above. A few others are non-immunosuppressive and claim the ability to treat cellular degeneration, and in some cases promote cellular regeneration, most often in the context of their antioxidant properties.

Specifically, Tso et al., U.S. Pat. No. 5,527,533, discloses the use of astaxanthin, a carotenoid antioxidant, for preventing or reducing photoreceptor damage resulting from the presence of free radicals. Similarly, Babcock et al., U.S. Pat. No. 5,252,319, discloses the use of antioxidant aminosteroids for treating eye disease and injury, by increasing resistance to oxidative damage. Freeman, U.S. Pat. No. 5,468,752, discloses the use of the antiviral phosphonylmethoxyalkylcytosines to reduce abnormally increased intraocular pressure.

Naturally occurring hormones, growth factors, cytokines, and signaling molecules are generally multifunctional and activate many genes in diverse cell lines. The present compounds do not, thus avoiding the unexpected, and potentially dangerous, side effects of systemic use. Similarly, the present compounds also avoid the potential unexpected side effects of introducing cell line-specific molecules into other cell lines where they do not naturally occur.

The epithelial hair cells in the organ of Corti of the inner ear, transduce sound into neural activity, which is transmitted along the cochlear division of the eighth cranial nerve. This nerve consists of fibers from three types of neurons (Spoendllin, H. H., in Friedmann, I. Ballantyne, J., eds. "Ultrastructural Atlas of the Inner Ear", London, Butterworth, pp. 133-164, (1984)) 1) afferent neurons, which lie in the spiral ganglion and connect the cochlea to the brainstem; 2) efferent olivocochlear neurons, which originate in the superior olivary complex; and 3) autonomic adrenergic neurons, which originate in the cervical sympathetic trunk and innervate the cochlea. In the human, there are approximately 30,000 afferent cochlear neurons, with myelinated axons, each consisting of about 50 lamellae, and 4-6 µm in diameter. This histologic structure forms the basis of uniform conduction velocity, which is an important functional feature. Throughout the length of the auditory nerve, there is a trophic arrangement of afferent fibers, with 'basal' fibers wrapped over the centrally placed 'apical' fibers in a twisted rope-like fashion. Spoendlin (Spoendlin, H. H. in Naunton, R. F., Fernadex, C. eds., "Evoked Electrical Activity in the Auditory Nervous System", London, Academic Press, pp. 21-39, (1978)) identified two types of afferent neurons in the spiral ganglion on the basis of morphologic differences: type I cells (95%) are bipolar and have myelinated cell bodies and axons that project to the inner hair cells. Type II cells (5%) are monopolar with unmyelinated axons and project to the outer hair cells of the organ of Corti. Each inner hair cell is innervated by about 20 fibers, each of which synapses on only one cell. In contrast, each outer hair cell is innervated by approximately six fibers, and each fiber branches to supply approximately 10 cells. Within the cochlea, the fibers divide into: 1) an inner spiral group, which arises primarily ipsilaterally and synapses with the afferent neurons to the inner hair cells, and 2) a more numerous outer radial group, which arises mainly contralaterally and synapses directly with outer hair cells. There is a minimal threshold at one frequency, the characteristic or best frequency, but the threshold rises sharply for frequencies above and below this level (Pickles, J. O. in "Introduction to the Physiology of Hearing", London, Academic Press, pp. 71-106, (1982)). Single auditory nerve fibers therefore appear to behave as band-pass filters. The basilar membrane vibrates preferentially to different frequencies, at different distances along its length, and the frequency selectivity of each cochlear nerve fiber is similar to that of the inner hair cell to which the fiber is connected. Thus, each cochlear nerve fiber exhibits a tuning curve covering a different range of frequencies from its neighboring fiber (Evans, E. F. in Beagley H. A. ed., "Auditory investigation: The Scientific and Technological basis", New York, Oxford University Pressm (1979)). By this mechanism, complex sounds are broken down into component frequencies (frequency resolution) by the filters of the inner ear.

Impairment anywhere along the auditory pathway, from the external auditory canal to the central nervous system, may result in hearing loss. The auditory apparatus can be subdivided into the external and middle ear, inner ear and auditory nerve and central auditory pathways. Auditory information in humans is transduced from a mechanical signal to a neurally conducted electrical impulse by the action of approximately 15,000 epithelial cells (hair cells) and 30,000 first-order neurons (spiral ganglion cells) in the inner ear. All central fibers of spiral ganglion neurons form synapses in the cochlear nucleus of the pontine brainstem, The number of neurons involved in hearing increases dramatically from the cochlea to the auditory brain stem and the auditory cortex. All auditory information is transduced by only 15,000 hair cells, of which the so-called inner hair cells, numbering 3500, are critically important, since they from synapses with approximately 90 percent of the 30,000 primary auditory neurons. Thus, damage to a relatively few cells in the auditory periphery can lead to substantial hearing loss. Hence, most causes of sensorineural loss can be ascribed to lesions in the inner ear (Nadol, J. B., *New England Journal of Medicine*, (1993), 329:1092-1102).

Hearing loss can be on the level of conductivity, sensorineural and central level. Conductive hearing loss is caused by lesions involving the external or middle ear, resulting in the destruction of the normal pathway of airborne sound amplified by the tympanic membrane and the ossicles to the inner ear fluids. Sensorineural hearing loss is due to lesions of the central auditory pathways. These consist of the cochlear and dorsal olivary nucleus complex, inferior colliculi, medial geniculate bodies, auditory cortex in the temporal lobes and interconnecting afferent and efferent fiber tracts (Adams R. D. and Maurice, V., eds., in "Principles of Neurology", (1989), McGraw-Hill Information Services Company, pp. 226-246).

Trauma due to acoustic overstimulation is another leading cause of deafness. There is individual susceptibility to trauma from noise. Clinically important sensorineural hearing loss may occur in some people exposed to high-intensity noise, even below levels approved by the Occupational Safety and Health Agency (Osguthorpe, J. D., ed., Washington D.C., American Academy of Otolaryngology-Head and Neck Surgery Foundation, (1988)).

Demyelinating processes, such as multiple sclerosis, may cause sensorineural hearing loss (Noffsinger, D., et al., *Acto Otolaryngol. Suppl.* (Stockh.) (1972), 303:1-63). More recently, a form of immune-mediated sensorineural hearing loss has been recognized (McCabe, B. F., *Ann. Otol. Rhinol. Laryngol.* (1979), 88:585-9). The hearing loss is usually bilateral, is rapidly progressive (measured in weeks and months), and may or may not be associated with vestibular symptoms.

A variety of tumors, both primary and metastatic, can produce either a conductive hearing loss, or a sensorineural hearing loss, by invading the inner ear or auditory nerve (Houck, J. R., et al., *Otolaryngol. Head Neck Surg.* (1992), 106:92-7). A variety of degenerative disorders of unknown cause can produce sensorineural hearing loss. Meniere's syndrome (Nadol, J. B., ed., "Meniere's Disease: Pathogenesis, Pathophysiology, Diagnosis, And Treatment," Amsterdam: Kugler & Ghedini (1989)), characterized by fluctuating sensorineural hearing Loss, episodic certigo, and tinnitus, appears to be caused by a disorder of fluid homeostasis within the inner ear, although the pathogenesis remains unknown. Sudden idiopathic sensorineural hearing loss (Wilson, W. R., et al., *Arch. Otolaryngol.* (1980), 106:772-6), causing moderate-to-severe sensorineural deafness, may be due to various causes, including inner ear ischemia and viral labyrinthitis.

Regardless of the cause, there exists a need to prevent or treat sensorineural hearing loss. The present invention provides such a method.

SUMMARY OF THE INVENTION

The present invention is directed to novel N-substituted cyclic aza compounds, and their preparation and use for treating neurodegenerative disorders, for treating alopecia and related hair loss disorders, for treating vision disorders and/or improving vision, for treating memory impairment and/or enhancing memory performance, and for treating sensorineural hearing loss. Preferred compounds include N-diketo cyclic aza derivative compounds, N-sulfonyl cyclic aza derivative compounds, tertiary N-aminocarbonyl cyclic aza compounds, and secondary N-aminocarbonyl cyclic aza compounds, wherein the diketo, sulfonyl, or aminocarbonyl group is attached to one of the nitrogen atoms (the 1-nitrogen) of the central aza heterocyclic ring, with an additional substituent substituted onto the 2-nitrogen of the central aza heterocyclic ring. These novel classes of aza derivative compounds contain the additional feature of a 5-7 membered aza heterocyclic ring in the central structure.

These compounds stimulate neuronal regeneration and outgrowth and as such are useful for treating neurological disorders and neurodegenerative diseases. These compounds also promote hair growth and as such are useful for treating hair loss disorders. These compounds also are useful for treating vision disorders, improving vision, treating memory impairment, enhancing memory performance, or treating hearing loss. A preferred feature of the compounds of the present invention is that they do not exert any significant immunosuppressive activity and/or are non-immunosuppressive as defined herein.

A preferred embodiment of this invention is a compound having the formula I:

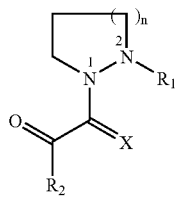

I or a pharmaceutically acceptable salt, ester or solvate thereof, wherein:

n is 1-3;

$R_1$ is selected from the group consisting of —$CR_3$, —$COOR_3$, —$COR_3$, —COOH, —$SO_3H$, —$SO_2HNR_3$, —$PO_2(R_3)_2$, —CN, —$PO_3(R_3)_2$, —$OR_3$, —$SR_3$, —NHCOR_3$, —$N(R_3)_2$, —$CON(R_3)_2$, —$CONH(O)R_3$, —$CONHNHSO_2R_3$, —$COHNSO_2R_3$, —$CONR_3CN$,

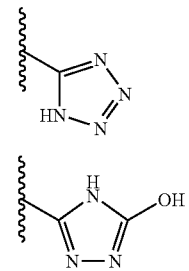

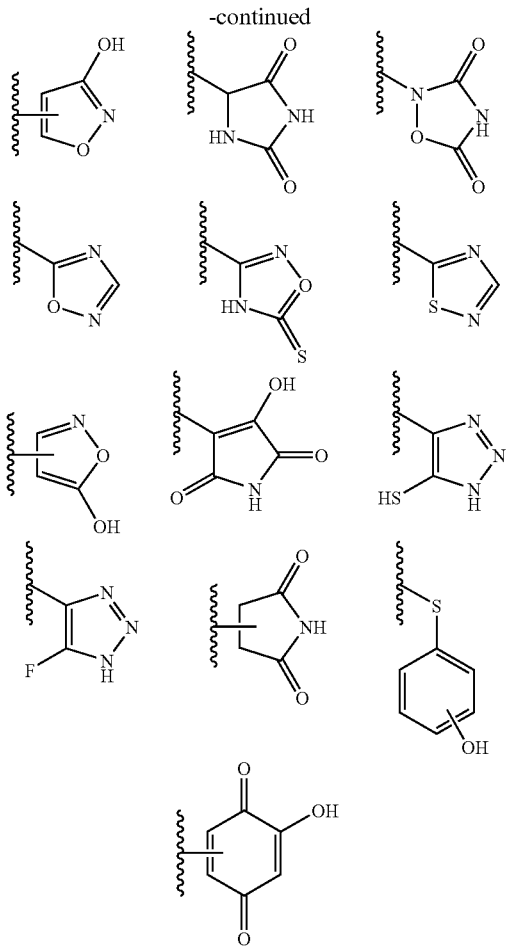

wherein said $R_1$ group is either unsubstituted or additionally substituted with $R_3$;

$R_2$ is selected from the group consisting of hydrogen, $C_1$-$C_9$ straight or branched chain alkyl, $C_2$-$C_9$ straight or branched chain alkenyl, $C_2$-$C_9$ straight or branched chain alkynyl, aryl, heteroaryl, carbocycle, or heterocycle, wherein said alkyl, alkenyl, alkynyl, aryl, heteroaryl, carbocycle, or heterocycle is unsubstituted on substituted with one or more substituents selected from $R_3$;

$R_3$ is selected from the group consisting of hydrogen, $C_1$-$C_9$ alkyl, $C_2$-$C_9$ straight or branched chain alkenyl, $C_2$-$C_9$ straight or branched chain alkynyl, $C_1$-$C_9$ alkoxy, $C_2$-$C_9$ alkenyloxy, aryloxy, phenoxy, benzyloxy, hydroxy, carboxy, $C_1$-$C_9$ thioalkyl, $C_2$-$C_9$ thioalkenyl, $C_1$-$C_9$ alkylamino, $C_2$-$C_9$ alkenylamino, cyano, nitro, imino, sulfonyl, thiocarbonyl, sulfhydryl, halo, haloalkyl, trifluoromethyl, aryl, heteroaryl, carbocycle, and heterocycle, wherein said alkyl, alkenyl, alkynyl, alkoxy, alkenyloxy, aryloxy, thioalkyl, thioalkenyl, alkylamino, alkenylamino, aryl, heteroaryl, carbocycle, or heterocycle group is optionally substituted with a hydroxy, carboxy, carbonyl, cyano, nitro, imino, sulfonyl, thiocarbonyl, sulfhydryl, halo, haloalkyl, trifluoromethyl, aryl, heteroaryl, carbocycle, or heterocycle group; and X is O or S.

Another preferred embodiment of this invention is a compound of formula II:

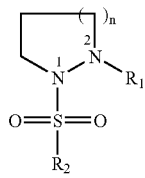

or a pharmaceutically acceptable salt, ester or solvate thereof, wherein:

n is 1-3;

$R_1$ is selected from the group consisting of —$CR_3$, —$COOR_3$, —$COR_3$, —COOH, —$SO_3H$, —$SO_2HNR_3$, —$PO_2(R_3)_2$, —CN, —$PO_3(R_3)_2$, —$OR_3$, —$SR_3$, —NH-$COR_3$, —$N(R_3)_2$, —$CON(R_3)_2$, —$CONH(O)R_3$, —$CONHNHSO_2R_3$, $COHNSO_2R_3$, —$CONR_3CN$,

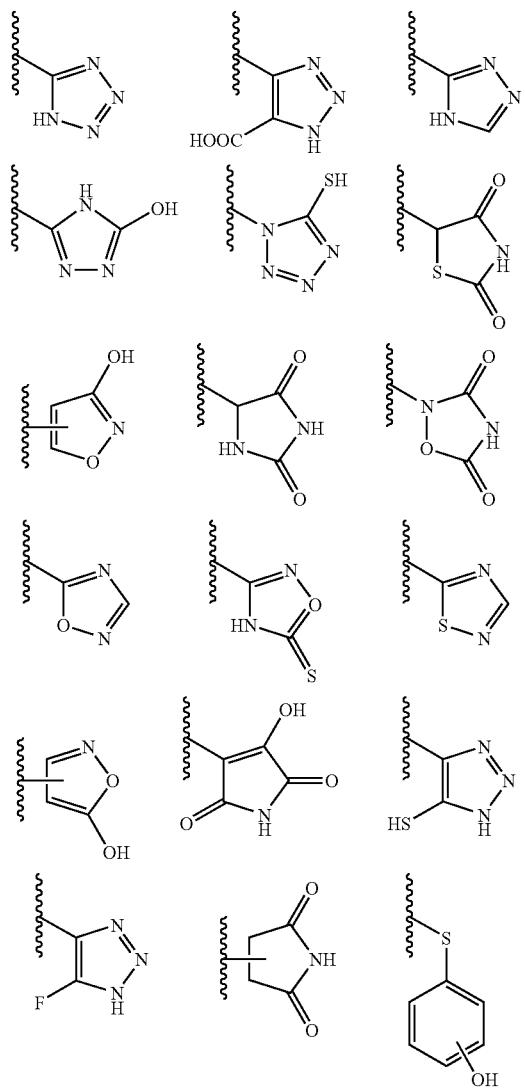

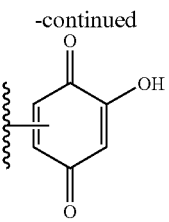

wherein said $R_1$ group is either unsubstituted or additionally substituted with $R_3$;

$R_2$ is selected from the group consisting of hydrogen, $C_1$-$C_9$ straight or branched chain alkyl, $C_2$-$C_9$ straight or branched chain alkenyl, $C_2$-$C_9$ straight or branched chain alkynyl, aryl, heteroaryl, carbocycle, or heterocycle, wherein said alkyl, alkenyl, alkynyl, aryl, heteroaryl, carbocycle, or heterocycle is unsubstituted or substituted with one or more substituents selected from $R_3$; and $R_3$ is selected from the group consisting of hydrogen, $C_1$-$C_9$ alkyl, $C_2$-$C_9$ straight or branched chain alkenyl, $C_2$-$C_9$ straight or branched chain alkynyl, $C_1$-$C_9$ alkoxy, $C_2$-$C_9$ alkenyloxy, aryloxy, phenoxy, benzyloxy, hydroxy, carboxy, $C_1$-$C_9$ thioalkyl, $C_2$-$C_9$ thioalkenyl, $C_1$-$C_9$ alkylamino, $C_2$-$C_9$ alkenylamino, cyano, nitro, imino, sulfonyl, thiocarbonyl, sulfhydryl, halo, haloalkyl, trifluoromethyl, aryl, heteroaryl, carbocycle, and heterocycle, wherein said alkyl, alkenyl, alkynyl, alkoxy, alkenyloxy, aryloxy, thioalkyl, thioalkenyl, alkylamino, alkenylamino, aryl, heteroaryl, carbocycle, or heterocycle group is optionally substituted with a hydroxy, carboxy, carbonyl, cyano, nitro, imino, sulfonyl, thiocarbonyl, sulfhydryl, halo, haloalkyl, trifluoromethyl, aryl, heteroaryl, carbocycle, or heterocycle group.

Yet another preferred embodiment of this invention is a compound of formula III:

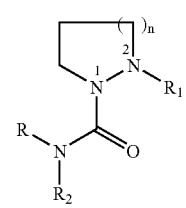

or a pharmaceutically acceptable salt, ester or solvate thereof, wherein:

n is 1-3;

$R_1$ is selected from the group consisting of —$CR_3$, —$COOR_3$, —$COR_3$, —COOH, —$SO_3H$, —$SO_2HNR_3$, —$PO_2(R_3)_2$, —CN, —$PO_3(R_3)_2$, —$OR_3$, —$SR_3$, —NH-$COR_3$, —$N(R_3)_2$, —$CON(R_3)_2$, —$CONH(O)R_3$, —$CONHNHSO_2R_3$, —$COHNSO_2R_3$, —$CONR_3CN$,

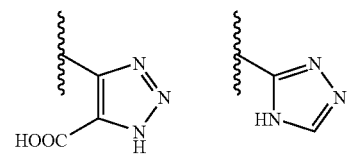

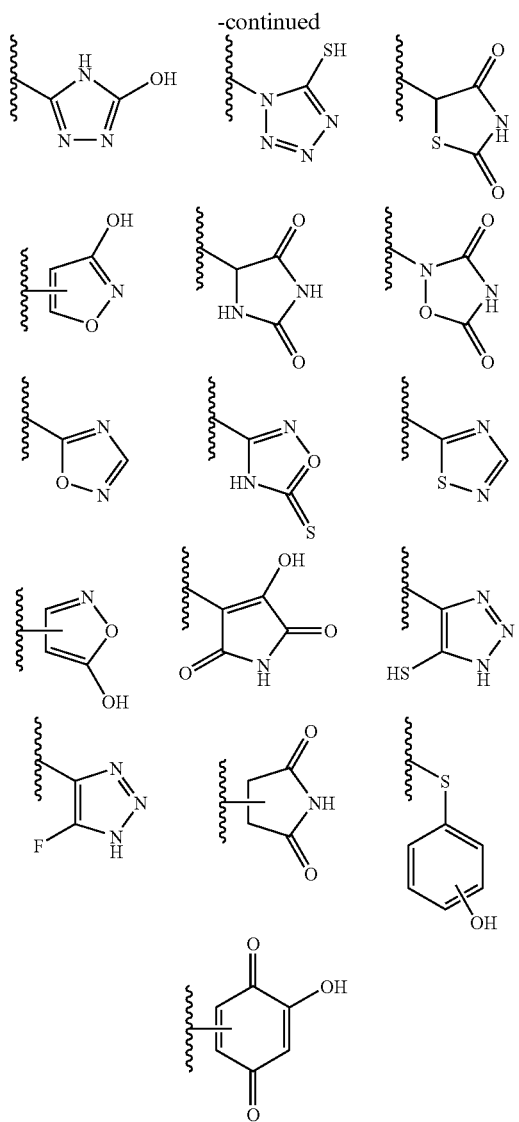

wherein said $R_1$ group is either unsubstituted or additionally substituted with $R_3$;

R and $R_2$ are independently $C_1$-$C_9$ alkyl, $C_2$-$C_9$ alkenyl, aryl, heteroaryl, carbocycle, or heterocycle, wherein said alkyl, alkenyl, aryl, heteroaryl, carbocycle, or heterocycle is unsubstituted or substituted with one or more substituent(s) selected from $R_3$; and $R_3$ is selected from the group consisting of hydrogen, $C_1$-$C_9$ alkyl, $C_2$-$C_9$ straight or branched chain alkenyl, $C_2$-$C_9$ straight or branched chain alkynyl, $C_1$-$C_9$ alkoxy, $C_2$-$C_9$ alkenyloxy, aryloxy, phenoxy, benzyloxy, hydroxy, carboxy, $C_1$-$C_9$ thioalkyl, $C_2$-$C_9$ thioalkenyl, $C_1$-$C_9$ alkylamino, $C_2$-$C_9$ alkenylamino, cyano, nitro, imino, sulfonyl, thiocarbonyl, sulfhydryl, halo, haloalkyl, trifluoromethyl, aryl, heteroaryl, carbocycle, and heterocycle, wherein said alkyl, alkenyl, alkynyl, alkoxy, alkenyloxy, aryloxy, thioalkyl, thioalkenyl, alkylamino, alkenylamino, aryl, heteroaryl, carbocycle, or heterocycle group is optionally substituted with a hydroxy, carboxy, carbonyl, cyano, nitro, imino, sulfonyl, thiocarbonyl, sulfhydryl, halo, haloalkyl, trifluoromethyl, aryl, heteroaryl, carbocycle, or heterocycle group.

Yet another preferred embodiment of this invention is a compound of formula IV:

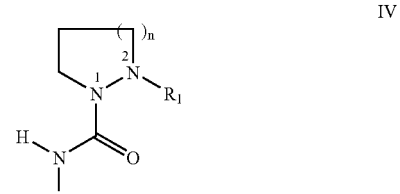

or a pharmaceutically acceptable salt, ester or solvate thereof, wherein:

n is 1-3;

$R_1$ is selected from the group consisting of —$CR_3$, —$COOR_3$, —$COR_3$, —COOH, —$SO_3H$, —$SO_2HNR_3$, —$PO_2(R_3)_2$, —CN, —$PO_3(R_3)_2$, —$OR_3$, —$SR_3$, —$NHCOR_3$, —$N(R_3)_2$, —$CON(R_3)_2$, —$CONH(O)R_3$, —$CONHNHSO_2R_3$, —$COHNSO_2R_3$, —$CONR_3CN$,

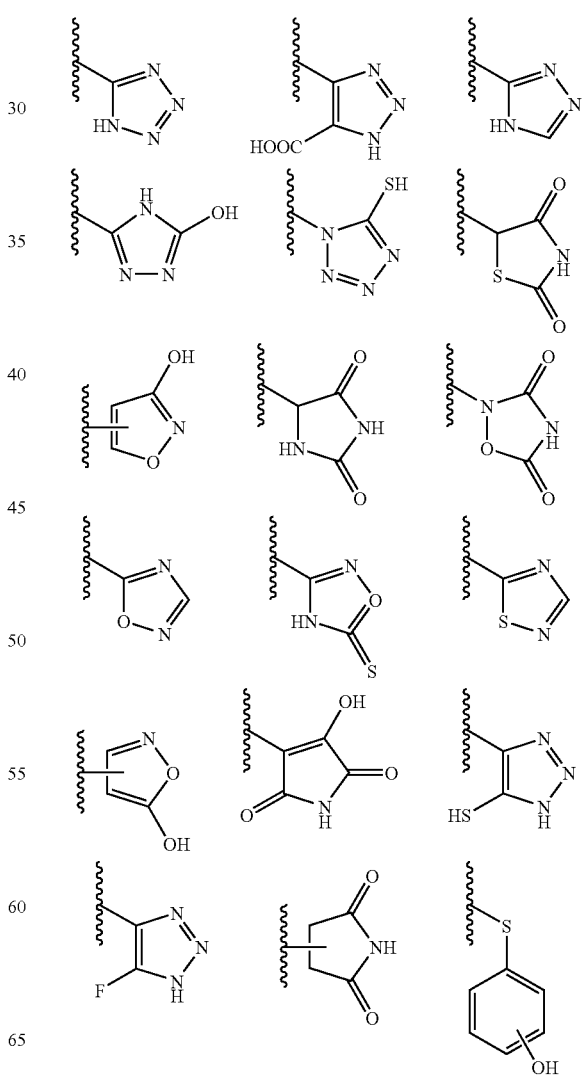

-continued

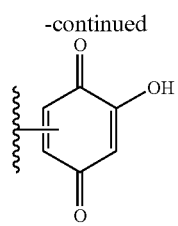

wherein said $R_1$ group is either unsubstituted or additionally substituted with $R_3$; and $R_2$ is $C_1$-$C_9$ alkyl, $C_2$-$C_9$ alkenyl, aryl, heteroaryl, carbocycle, or heterocycle, wherein said alkyl, alkenyl, aryl, heteroaryl, carbocycle, or heterocycle is substituted with one or more substituent(s) selected from $R_3$; and $R_3$ is selected from the group consisting of hydrogen, $C_1$-$C_9$ alkyl, $C_2$-$C_9$ straight or branched chain alkenyl, $C_2$-$C_9$ straight or branched chain alkynyl, $C_1$-$C_9$ alkoxy, $C_2$-$C_9$ alkenyloxy, aryloxy, phenoxy, benzyloxy, hydroxy, carboxy, $C_1$-$C_9$ thioalkyl, $C_2$-$C_9$ thioalkenyl, $C_1$-$C_9$ alkylamino, $C_2$-$C_9$ alkenylamino, cyano, nitro, imino, sulfonyl, thiocarbonyl, sulfhydryl, halo, haloalkyl, trifluoromethyl, aryl, heteroaryl, carbocycle, and heterocycle, wherein said alkyl, alkenyl, alkynyl, alkoxy, alkenyloxy, aryloxy, thioalkyl, thioalkenyl, alkylamino, alkenylamino, aryl, heteroaryl, carbocycle, or heterocycle group is optionally substituted with a hydroxy, carboxy, carbonyl, cyano, nitro, imino, sulfonyl, thiocarbonyl, sulfhydryl, halo, haloalkyl, trifluoromethyl, aryl, heteroaryl, carbocycle, or heterocycle group.

Another preferred embodiment is a pharmaceutical composition, comprising:

(i) an effective amount of the compound of formulae I, II, III, or IV; and (ii) a pharmaceutically acceptable carrier.

For neurotrophic compositions, a neurotrophic factor different from the present inventive compounds may also be administered or otherwise included in the composition.

Another preferred embodiment of the invention is a method of treating a neurological disorder in an animal, comprising administering to the animal an effective amount of the compound of formulae I, II, III, or IV to stimulate growth of damaged peripheral nerves or to promote neuronal regeneration.

Another preferred embodiment of the invention is a method of stimulating growth of damaged peripheral nerves, comprising administering to a damaged peripheral nerve an effective amount of the compound of formulae I, II, III, or IV to stimulate or promote growth of the damaged peripheral nerve.

Another preferred embodiment of the invention is a method of promoting neuronal regeneration and growth in animals, comprising administering to an animal an effective amount of the compound of formulae I, II, III, or IV to promote neuronal regeneration.

Another preferred embodiment of the invention is a method of preventing neurodegeneration in animals, comprising administering to an animal an effective amount of the compound of formulae I, II, III, or IV to prevent neurodegeneration.

Another preferred embodiment of the invention is a method for treating alopecia or promoting hair growth in an animal, comprising administering to an animal an effective amount of the compound of formulae I, II, III, or IV.

Another preferred embodiment of the invention is a method for treating a vision disorder, improving vision, treating memory impairment, enhancing memory performance, or treating sensorineural hearing loss in an animal, comprising administering to an animal an effective amount of the compound of formulae I, II, III, or IV.

The present invention further contemplates a process for preparing the cyclic aza derivative compounds of the invention.

The present invention further contemplates the compound(s) of the invention for use in treatment of a disease. In particular, the present invention contemplates the compound(s) of the invention for use in treatment of the disorders enumerated herein.

The present invention further contemplates the compound(s) of the invention for use in the preparation of a medicament or pharmaceutical composition. In particular, the invention contemplates the compound(s) of the invention for use in the preparation of a medicament or pharmaceutical composition for treatment of the disorders enumerated herein.

The invention also provides for the use of compound(s) of the invention for treating a disease. In particular, the invention provides for the use of compound(s) of the invention for treating the disorders enumerated herein.

The invention also provides for the use of compound(s) of the invention in the manufacture of a medicament or pharmaceutical composition. In particular, the invention provides for the use of compound(s) of the invention in the manufacture of a medicament or pharmaceutical composition for the treatment of the disorders enumerated herein. Such pharmaceutical compositions include, as appropriate to the specific disorder, topical, systemic, oral, or injectable formulations. It is further contemplated that the compound(s) of the invention may be administered with an effective amount of a second therapeutic agent for the treatment of the enumerated disorders. A variety of pharmaceutical formulations and different delivery techniques are described in further detail below.

DETAILED DESCRIPTION OF THE INVENTION

Definitions

"Alkyl", alone or in combination, refers to a straight-chain or branched-chain hydrocarbon radical containing a designated number of carbon atoms. For example, $C_1$-$C_9$ alkyl is a straight or branched hydrocarbon chain containing 1 to 9 carbon atoms. Examples of such radicals include methyl, ethyl, propyl, iso-propyl, butyl, iso-butyl, tert-butyl, n-pentyl, n-hexyl, and the like, unless otherwise indicated.

"Alkenyl", alone or in combination, refers to a straight-chain or branched-chain hydrocarbon radical having one more double bonds, preferably 1-2 double bonds and more preferably one double bond, and containing a designated number of carbon atoms. For example, $C_2$-$C_9$ alkenyl is a straight or branched hydrocarbon chain containing 2 to 9 carbon atoms having at least one double bond, and includes but is not limited to ethenyl, propenyl, iso-propenyl, butenyl, 2-methylpropenyl, iso-butenyl, tert-butenyl, 1,4-butadienyl, n-pentenyl, n-hexenyl, and the like, unless otherwise indicated.

"Alkynyl", alone or in combination, refers to a straight-chain or branched-chain hydrocarbon radical having one or more triple bonds, preferably 1-2 triple bonds and more preferably one triple bond, and containing a designated number of carbon atoms. For example, $C_2$-$C_9$ alkynyl is a straight or branched hydrocarbon chain containing 2 to 9 carbon atoms having at least one triple bond, and includes but is not limited to ethynyl, propynyl (propargyl), butynyl, and the like, unless otherwise indicated.

"Alkanoyl", alone or in combination, means a radical of the type "R—C(O)—" wherein "R" is an alkyl radical as defined above and "—C(O)—" is a carbonyl radical. Examples of such alkanoyl radicals include without limitation acetyl, trifluoroacetyl, hydroxyacetyl, propanoyl, butyryl, pentanoyl, and the like.

"Alkoxy", alone or in combination, refers to a radical of the type "—OR" wherein "R" is alkyl radical as defined above and "O" is an oxygen atom. Preferably, R is a branched or unbranched saturated hydrocarbon chain containing 1 to 9 carbon atoms. Examples of such alkoxy radicals include without limitation methoxy, ethoxy, n-propoxy, isopropoxy, n-butoxy, iso-butoxy, sec-butoxy, tert-butoxy, and the like, unless otherwise indicated.

It should be kept in mind that, throughout this application, "R" or "$R_n$", where n is a number, is used to designate various alkyl (and other) substituents. As indicated throughout, these R groups are independently selected. Thus, for example, the fact that $R_1$ may be a branched alkyl in one context does not require that $R_1$ be the same branched alkyl, and does not prohibit that $R_1$ be, for example, a straight chain alkenyl, in another context in the same molecule. It is intended that all "$R_n$" are selected independently of all other "$R_n$", whether or not the term "independently selected" is used or is inadvertently omitted.

"Aryl" or "aromatic" refers to an aromatic carbocyclic or heterocyclic moiety having one or more closed rings which is optionally substituted with one or more substituents selected from alkyl, alkoxy, halogen, hydroxy, amino, azido, nitro, cyano, haloalkyl, carboxy, alkoxycarbonyl, cycloalkyl, heterocyclo, alkanoylamino, amido, amidino, alkoxycarbonylamino, N-alkylamidino, alkylamino, dialkylamino, N-alkylamido, N,N-dialkylamido, aralkoxycarbonylamino, alkylthio, alkylsulfinyl, alkylsulfonyl, and the like. Any substituents attached to an aryl moiety in the compounds of the present invention may be configured in the ortho-, meta-, or para- orientations, with the para-orientation being preferred. Examples of preferred aryl radicals include, without limitation, phenyl, p-tolyl, 4-methoxyphenyl, 4-(tert-butoxy)phenyl, 3-methyl-4-methoxyphenyl, 4-$CF_3$-phenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 2-amino-3-methylphenyl, 2,4-dimethyl-3-aminophenyl, 4-hydroxyphenyl, 3-methyl-4-hydroxyphenyl, 4-(4-methoxyphenyl)phenyl, naphthyl, 3-amino-1-naphthyl, 2-methyl-3-amino-1-naphthyl, 6-amino-2-naphthyl, piperazinylphenyl, anthracenyl, phenanthracenyl, biphenyl, pyrenyl, and the like.

Other examples of typical aryl moieties included in the scope of the present invention may include, but are not limited to, the following:

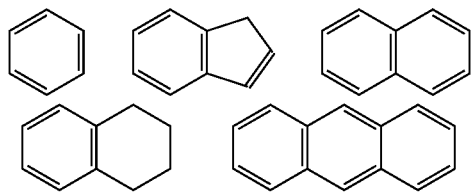

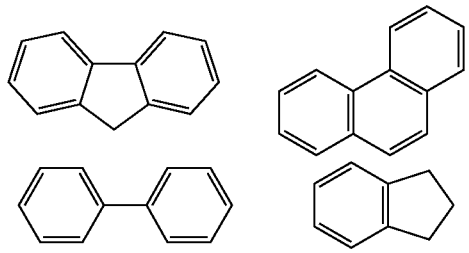

-continued

It should be kept in mind that, throughout this application, "Ar" or "$Ar_n$", where n is a number, is used to designate various cyclic (and other) substituents. As indicated throughout, these Ar groups are independently selected. Thus, for example, the fact that $Ar_2$ may be phenyl in one context does not require that $Ar_2$ be phenyl, nor prohibit that $Ar_2$ be, for example, pyridyl, in another context in the same molecule. It is intended that all "$Ar_n$" are selected independently of all other "$Ar_n$", whether or not the term "independently selected" is used or is inadvertently omitted.

"Bridged ring" or "bridged ring moiety", alone or in combination, refers to a carbocyclic or heterocyclic moiety where two or more atoms are shared between two or more ring structures, where any such shared atom is C, N, S, or other heteroatom arranged in a chemically reasonable substitution pattern and which is optionally substituted as defined herein with respect to the definition of aryl. Alternatively, a "bridged" compound also refers to a carbocyclic or heterocyclic ring structure where one atom at any position of a primary ring is bonded to a second atom on the primary ring through either a chemical bond or atom(s) other than a bond which do not comprise a part of the primary ring structure. The first and second atom may or may not be adjacent to one another in the primary ring. Illustrated below are specific nonlimiting examples of bridged ring structures contemplated by the present invention:

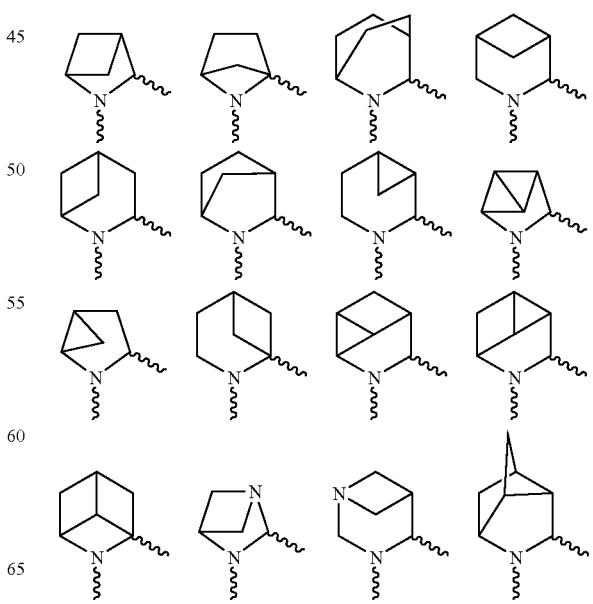

-continued

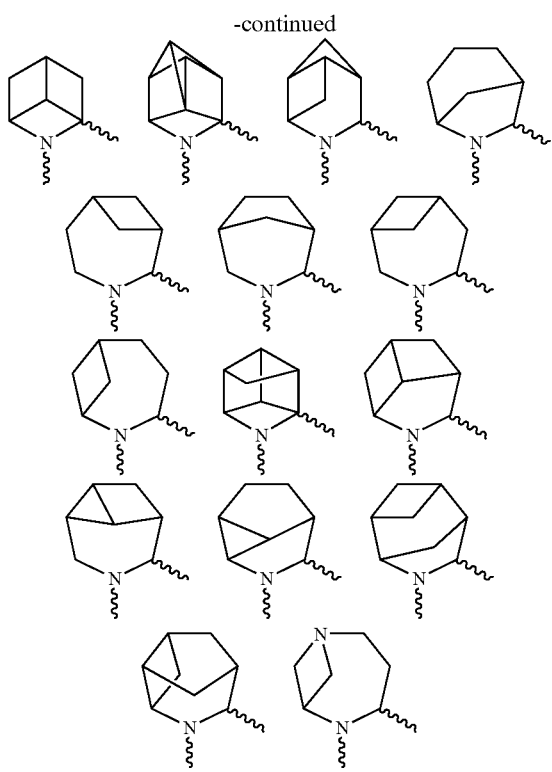

The present invention also contemplates other carbocyclic or heterocyclic bridged ring structures, including bridged rings wherein the bridging atoms are C or heteroatom(s) arranged in chemically reasonable substitution patterns, which are not described herein.

"Heteroaryl", alone or in combination, refers to an aromatic heterocyclic moiety having one or more closed rings with one or more heteroatoms (for example, sulfur, nitrogen or oxygen) in at least one of the rings and which is optionally substituted as defined herein with respect to the definition of aryl. Examples include, without limitation, pyrrole, thiophene, pyridine and isoxazole.

"Carbocycle" or "carbocyclic", alone or in combination, refers to a saturated or partially saturated hydrocarbon, cyclic moiety having one or more closed rings that is/are alicyclic, aromatic, fused and/or bridged, and which is optionally substituted as defined herein with respect to the definition of aryl. "Heterocycle" or "heterocyclic", alone or in combination, refers to a saturated or partially unsaturated, cyclic moiety having one or more closed rings that is/are alicyclic, aromatic, fused and/or bridged, with one or more heteroatoms (for example, sulfur, nitrogen or oxygen) in at least one of the rings and which may or may not include carbon and which is optionally substituted as defined herein with respect to the definition of aryl. "Heterocycle" is intended to include sulfone and sulfoxide derivatives of sulfur ring members and N-oxides of tertiary nitrogen ring members, and benzofused ring systems.

Examples of preferred carbocyclic and heterocyclic moieties include, without limitation, cyclopentyl, cyclohexyl, cycloheptyl, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, and adamantyl.

As one skilled in the art will appreciate, such heterocyclic moieties may exist in several isomeric forms, all of which are encompassed by the present invention. For example, a 1,3,5-triazine moiety is isomeric to a 1,2,4-triazine group. Such positional isomers are to be considered within the scope of the present invention. Likewise, the heterocyclic or heteroaryl groups can be bonded to other moieties in the compounds of the present invention. The point(s) of attachment to these other moieties is not to be construed as limiting on the scope of the invention. Thus, by way of example, a pyridyl moiety may be bound to other groups through the 2-, 3-, or 4-position of the pyridyl group. All such configurations are to be construed as within the scope of the present invention.

Examples of heterocyclic or heteroaryl moieties included in the scope of the present invention may include, but are not limited to, the following:

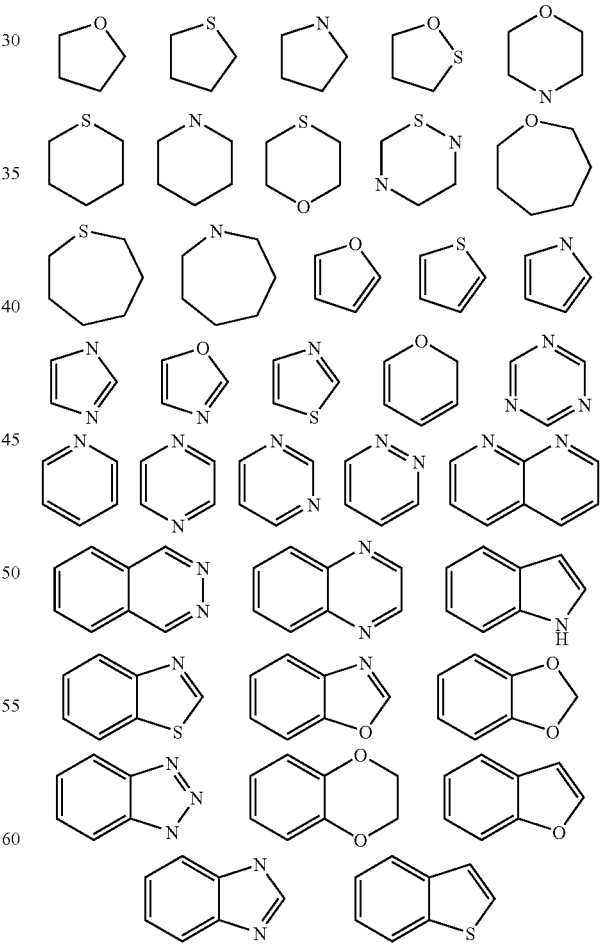

"Derivative" refers to a substance produced from another substance either directly or by modification or partial substitution. In particular, a "derivative" of a compound is a compound obtainable from the original compound by a simple chemical process.

"Activated derivative" of a compound means a reactive form of the original compound which renders the compound active in a desired chemical reaction, in which the original compound is only moderately reactive or non-reactive. Activation is achieved by formation of a derivative or a chemical grouping within the molecule with a higher free energy content than that of the original compound, which renders the activated form more susceptible to react with another reagent. One skilled in the art would be able to identify various activated derivatives useful in preparing the present inventive compounds. Particularly preferred activated derivatives can include, for example, halo, a lower acyloxy group, a carbodiimide group such as 1-ethyl-3-(3-dimethylaminopropyl) carbodiimide (EDAC), an isobutyrate group, an amino acid anhydride protected amino acid, N-carboxyanhydrides (NCA's), a triazole, a mixed anhydride (see, for example, G. E. Krejcarek and K. L. Tucker, Biochem., Biophys. Res. Commun. 1977, 581, the entire contents of which are hereby incorporated by reference), such as a coupling reagent with dicyclohexyl dicarbodiimide (DCC), acid halides, anhydrides, acid chlorides, acid hydrides, activated esters, nitrenes, isothiocyanates, and acyl cyanides or anhydrides (see Tetrahedron Letters, Volume 18, (1973), pp. 1595-1598, the entire contents of which are hereby incorporated by reference).

"Effective amount" refers to the amount required to produce the desired effect. "Therapeutically effective amount" refers to the amount required to effect a desired therapeutic activity as defined herein, such as stimulation of neuronal regeneration, treating neurological disorders, treating alopecia and related hair loss disorders, treating vision disorders and/or improving vision, treating memory impairment and/or enhancing memory performance, and treating sensorineural-hearing loss. A therapeutically effective amount can be determined according to assays known to one of ordinary skill in the art, such as the MPTP assay, described herein below.

"Halo" refers to at least one fluoro, chloro, bromo or iodo moiety.

"Isosteres" refer to elements, molecules, or ions having different molecular formulae but exhibiting similar or identical physical properties. For example, tetrazole is an isostere of carboxylic acid because it mimics the properties of carboxylic acid even though they both have very different molecular formulae. Tetrazole is one of many possible isosteric replacements for carboxylic acid. Similarly, carboxylic ester isosteres mimic the properties of an ester even though they have very different molecular formulae. Ideally, isosteric compounds should be isomorphic and able to co-crystallize. Among the other physical properties that isosteric compounds can share are boiling point, density, viscosity and thermal conductivity. The term "isosteres" encompass "bioisosteres".

"Bioisosteres" are isosteres which, in addition to their physical similarities, share some common biological properties. Typically, bioisosteres interact with the same recognition site or produce broadly similar biological effects.

"Carboxylic acid isosteres" and "carboxylic ester isosteres" include without limitation direct derivatives such as hydroxamic acids, acyl-cyanamides and acylsulfonamides; planar acidic heterocycles such as tetrazoles, mercaptoazoles, sulfinylazoles, sulfonylazoles, isoxazoles, isothiazoles, hydroxythiadiazoles and hydroxychromes; and nonplanar sulfur- or phosphorus-derived acidic functions such as phosphinates, phosphonates, phosphonamides, sulphonates, sulphonamides, and acylsulphonamides. The terms "carboxylic acid isostere" and "carboxylic ester isostere" are well known to a person of ordinary skill in the art, as evidenced by the teaching of Thornber et al., "Isosterism and molecular modification in drug design", Chem. Rev. 8(4), p. 563-565 and King, "Biosisosteres, Conformational Restriction, and Pro-drugs-Case History: An Example of a Conformational Restriction Approach", *Med. Chem. Principle Practice*, 1994, P. 206-109, the contents of which are incorporated herein by reference in their entirety. Examples of these types of isosteres include, without limitation: —COOH, —SO$_3$H, —SO$_2$HNR$_3$,—PO$_2$(R$_3$)$_2$, —CN, —PO$_3$(R$_3$)$_2$, —OR$_3$, —SR$_3$, —NHCOR$_3$, —N(R$_3$)$_2$, —CON(R$_3$)$_2$, —CONH(O)R$_3$, —CONHNHSO$_2$R$_3$, —COHNSO$_2$R$_3$, —CONR$_3$CN,

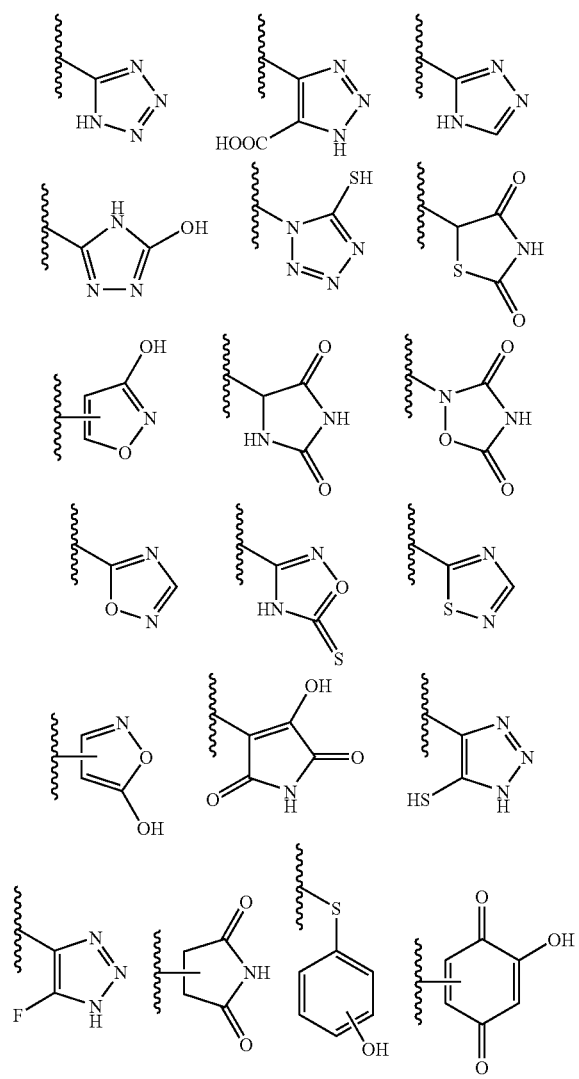

In addition, carboxylic acid isosteres can include 5-7 membered carbocycles or heterocycles containing any combination of CH$_2$, O, S, or N in any chemically stable oxidation state, where any of the atoms of said ring structure are optionally substituted in one or more positions.

The present invention contemplates that when chemical substituent(s) are added to a carboxylic acid or ester isostere, the inventive compound retains the properties of a carboxylic acid or ester isostere.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction, and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl, and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis (methylene)benzene, phthalimidyl, succinimidyl, maleimidyl, and the like and where these heterocyclic groups can further include adjoining aryl and cycloalkyl mono-, di-, or tri-substituted. Amino groups may also be protected against undesired reactions, such as oxidation, through the formation of an addition salt, such as hydrochloride, toluenesulfonic acid, trifluoroacetic acid, and the like. Many of the amino protecting groups are also suitable for protecting carboxy, hydroxy, and mercapto groups. Alkyl groups are also suitable groups for protecting hydroxy and mercapto groups.

"Low molecular weight, small molecule compounds" include, without limitation, molecules which are smaller in size, molecular weight, or both in relation to the compounds Rapamycin, Cyclosporin, and FK506. Preferably, such compounds have a molecular weight no more than about 800 daltons; more preferably, no more than about 650 daltons; most preferably, no more than about 500 daltons; even more preferably, no more than about 450 daltons; more preferably, no more than about 400 daltons; more preferably, no more than about 350 daltons, and more preferably, no more than about 300 daltons.

"Pharmaceutically acceptable carrier" as used herein refers to any carrier, diluent, excipient, suspending agent, lubricating agent, adjuvant, vehicle, delivery system, emulsifier, disintegrant, absorbent, preservative, surfactant, colorant, flavorant, or sweetener. For these purposes, the compounds of the present invention may be administered orally, parenterally, by inhalation spray, topically, rectally, nasally, buccally, vaginally, or via an implanted reservoir in dosage formulations containing conventional non-toxic pharmaceutically-acceptable carriers, adjuvants, and vehicles. The term parenteral as used herein includes subcutaneous, intravenous, intramuscular, intraperitoneal, intrathecal, intraventricular, intrasternal, and intracranial injection or infusion techniques.

"Pharmaceutically acceptable salt", as used herein, refers to an organic or inorganic salt of the inventive compounds which possesses the desired pharmacological activity and which is neither biologically nor otherwise undesirable. Such salts can be acid or basic addition salts, depending on the nature of the inventive compound to be used.

In the case of an acidic moiety in an inventive compound, a salt may be formed by treatment of the inventive compound with a basic compound, particularly an inorganic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine. Other suitable base salts, esters, or solvates include magnesium salts; salts with organic bases, such as dicyclohexylamine salts; and N-methyl-D-glucamine. An especially preferred salt is a sodium or potassium salt of an inventive compound. Free acids can be additionally preferred.

With respect to basic moieties, a salt is formed by the treatment of the desired inventive compound with an acidic compound, particularly an inorganic acid. Preferred inorganic salts of this type may include, for example, the hydrochloric, hydrobromic, hydroiodic, sulfuric, phosphoric or the like salts. Preferred organic salts of this type, may include, for example, salts formed with formic, acetic, succinic, citric, lactic, maleic, fumaric, palmitic, cholic, pamoic, mucic, d-glutamic, d-camphoric, glutaric, glycolic, phthalic, tartaric, lauric, stearic, salicyclic, methanesulfonic, benzenesulfonic, para-toluenesulfonic, sorbic, puric, benzoic, cinnamic and the like organic acids. Other suitable acids are adipate, alginate, aspartate, benzenesulfonate, bisulfate, butyrate, camphorsulfonate, cyclopentanepropionate, digluconate, dodecylsulfate, ethanesulfonate, glucoheptanoate, glycerophosphate, hemisulfate, heptanoate, hexanoate, 2-hydroxyethanesulfonate, methanesulfonate, naphthylate, 2-naphthalenesulfonate, nicotinate, oxalate, thiocyanate, tosylate and undecanoate. An especially preferred salt of this type is a hydrochloride or sulfate salt of the desired inventive compound. Also, the basic nitrogen-containing groups can be quarternized with such agents as: 1) lower alkyl halides, such as methyl, ethyl, propyl, and butyl chloride, bromides and iodides; 2) dialkyl sulfates like dimethyl, diethyl, dibutyl and diamyl sulfates; 3) long chain alkyls such as decyl, lauryl, myristyl and stearyl substituted with one or more halide such as chloride, bromide and iodide; and 4) aralkyl halides like benzyl and phenethyl bromide and others. Free bases can be additionally preferred.

"Isomers" refer to compounds having the same number and kind of atoms (same molecular formula), and hence the same molecular weight, but differing in respect to the arrangement or configuration of the atoms.

"Stereoisomers" refer to isomers that differ only in the arrangement of the atoms in space. "Diastereoisomers" are stereoisomers which are not mirror images of each other.

"Optical isomers" refer to either of two kinds of stereoisomers. One kind is represented by mirror-image structures called enantiomers, which result from the presence of one or more asymmetric carbon atoms in the compound (glyceraldehyde, lactic acid, sugars, tartaric acid, amino acids). The other kind is exemplified by diastereoisomers, which are not mirror images. These occur in compounds having two or more asymmetric carbon atoms; thus, such compounds have $2_n$ optical isomers, where n is the number of asymmetric carbon atoms.

"Enantiomers" refer to a pair of stereoisomers that are non-superimposable mirror images of each other.

"Racemic mixture" refers to a mixture containing equal parts of individual enantiomers. "Non-racemic mixture" is a mixture containing unequal parts of individual enantiomers or stereoisomers.

Further, as used throughout the teaching of the invention, a designation of:

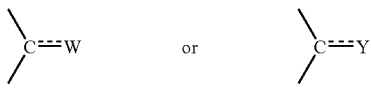

wherein W or Y is $H_2$, or similar designations, is meant to denote that two hydrogen atoms are attached to the noted carbon and that the bonds to each hydrogen are single bonds.

"Alopecia" refers to deficient hair growth and partial or complete loss of hair, including without limitation androgenic alopecia (male pattern baldness), toxic alopecia, alopecia senilis, alopecia areata, alopecia pelada and trichotillomania. Alopecia results when the pilar cycle is disturbed. The most frequent phenomenon is a shortening of the hair growth or anagen phase due to cessation of cell proliferation. This results in an early onset of the catagen phase, and consequently a large number of hairs in the telogen phase during which the follicles are detached from the dermal papillae, and the hairs fall out. Alopecia has a number of etiologies, including genetic factors, aging, local and systemic diseases, febrile conditions, mental stresses, hormonal problems, and secondary effects of drugs.

"Animal" refers to a living organism having sensation and the power of voluntary movement, and which requires for its existence oxygen and organic food. Examples include, without limitation, an animal such as a member of the human, equine, porcine, bovine, murine, canine, or feline species. A preferred animal is mammal. In the case of a human, an "animal" may also be referred to as a "patient".

"Disease" refers to any deviation from or interruption of the normal structure or function of any part, organ, or system (or combinations) of the body that is manifested by a characteristic set of symptoms and signs and whose etiology, pathology, and prognosis may be known or unknown. *Dorland's Illustrated Medical Dictionary*, (W.B. Saunders Co. 27th ed. 1988).

"Disorder" refers to any derangement or abnormality of function; a morbid physical or mental state. *Dorland's Illustrated Medical Dictionary*, (W.B. Saunders Co. 27th ed. 1988).

"Enhancing memory performance" refers to improving or increasing the mental faculty by which to register, retain or recall past experiences, knowledge, ideas, sensations, thoughts, or impressions.

"Eye" refers to the anatomical structure responsible for vision in humans and other animals, and encompasses the following anatomical structures, without limitation: lens, vitreous body, ciliary body, posterior chamber, anterior chamber, pupil, cornea, iris, canal of Schlemm, zonules of Zinn, limbus, conjunctiva, choroid, retina, central vessels of the retina, optic nerve, fovea centralis, macula lutea, and sclera.

"Memory impairment" refers to a diminished mental registration, retention or recall of past experiences, knowledge, ideas, sensations, thoughts or impressions. Memory impairment may affect short and long-term information retention, facility with spatial relationships, memory (rehearsal) strategies, and verbal retrieval and production. Common causes of memory impairment are age, severe head trauma, brain anoxia or ischemia, alcoholic-nutritional diseases, drug intoxications and neurodegenerative diseases. For example, memory impairment is a common feature of neurodegenerative diseases such as Alzheimer's disease and senile dementia of the Alzheimer type. Memory impairment also occurs with other kinds of dementia such as multi-infarct dementia, a senile dementia caused by cerebrovascular deficiency, and the Lewy-body variant of Alzheimer's disease with or without association with Parkinson's disease. Creutzfeldt-Jakob disease is a rare dementia with which memory impairment is associated. It is a spongiform encephalopathy caused by the prion protein; it may be transmitted from other sufferers or may arise from gene mutations. Loss of memory is also a common feature of brain-damaged patients. Brain damage may occur, for example, after a classical stroke or as a result of an anaesthetic accident, head trauma, hypoglycemia, carbon monoxide poisoning, lithium intoxication, vitamin ($B_1$, thiamine and $B_{12}$) deficiency, or excessive alcohol use. Korsakoff's amnesic psychosis is a rare disorder characterized by profound memory loss and confabulation, whereby the patient invents stories to conceal his or her memory loss. It is frequently associated with excessive alcohol intake. Memory impairment may furthermore be age-associated; the ability to recall information such as names, places and words seems to decrease with increasing age. Transient memory loss may also occur in patients, suffering from a major depressive disorder, after electro-convulsive therapy.

"Neopsic factors" or "neopsics" refers to compounds useful in treating vision loss, preventing vision degeneration, or promoting vision regeneration.

"Neopsis" refers to the process of treating vision loss, preventing vision degeneration, or promoting vision regeneration.

"Neurotrophic" includes without limitation the ability to stimulate neuronal regeneration or growth, and/or the ability to prevent or treat neurodegeneration. Assays for determining the neurotrophic abilities of a compound are well known to those of ordinary skill in the art. Specific, non-limiting examples of well known assays include MPTP and chick DRG assays. Preferably, neurotrophic compounds exhibit an MPTP Assay value which is greater than about 3% recovery of TH-stained dopaminergic neurons; more preferably, greater than about 10% recovery of TH-stained dopaminergic neurons; more preferably, greater than about 20% recovery of TH-stained dopaminergic neurons; more preferably, greater than about 35% recovery of TH-stained dopaminergic neurons; most preferably, greater than about 50% recovery of TH-stained dopaminergic neurons.

"Non-immunosuppressive" as used herein refers to the inability of the compounds of the present invention to trigger an immune response when compared to a control such as FK506 or cyclosporin A. Assays for determining immunosuppression are well known to those of ordinary skill in the art. Specific, non-limiting examples of well known assays include PMA and OKT3 wherein mitogens are used to stimulate proliferation of human peripheral blood lymphocytes (PBC) and the compounds are evaluated on their ability to inhibit such proliferation.

"Ophthalmological" refers to anything about or concerning the eye, without limitation, and is used interchangeably with "ocular", ophthalmic", "opthalmologic", and other such terms, without limitation.

"Pilar cycle" refers to the life cycle of hair follicles, and includes three phases:

(1) the anagen phase, the period of active hair growth which, insofar as scalp hair is concerned, lasts about three to five years;

(2) the catagen phase, the period when growth stops and the follicle atrophies which, insofar as scalp hair is concerned, lasts about one to two weeks; and (3) the telogen phase, the rest period when hair progressively separates and finally falls out which, insofar as scalp hair is concerned, lasts about three to four months.

Normally 80 to 90 percent of the follicles are in the anagen phase, less than 1 percent being in the catagen phase, and the rest being in the telogen phase. In the telogen phase, hair is uniform in diameter with a slightly bulbous, non-pigmented root. By contrast, in the anagen phase, hair has a large colored bulb at its root.

"Promoting hair growth" refers to maintaining, inducing, stimulating, accelerating, or revitalizing the germination of hair.

"Promoting vision regeneration" refers to maintaining, improving, stimulating or accelerating recovery of, or revitalizing one or more components of the visual system in a manner which improves or enhances vision, either in the presence or absence of any ophthalmologic disorder, disease, or injury.

"Preventing neurodegeneration" as used herein includes the ability to inhibit or prevent neurodegeneration in patients newly diagnosed as having a neurodegenerative disease, or at risk of developing a new degenerative disease and for inhibiting or preventing further neurodegeneration in patients who are already suffering from or have symptoms of a neurodegenerative disease when the compounds are given concurrently.

"Preventing vision degeneration" as used herein includes the ability to prevent degeneration of vision in patients newly diagnosed as having a degenerative disease affecting vision, or at risk of developing a new degenerative disease affecting vision, and for preventing further degeneration of vision in patients who are already suffering from or have symptoms of a degenerative disease affecting vision.

"Treating" or "treatment" as used herein refers to:

(i) preventing a disease, disorder, or condition from occurring in an animal which may be predisposed to the disease, disorder, and/or condition but has not yet been diagnosed as having it;

(ii) inhibiting the disease, disorder, or condition, i.e., arresting its development; and/or (iii) relieving the disease, disorder, or condition, i.e., causing regression of the disease, disorder, and/or condition.

"Treating alopecia" refers to:

(i) preventing alopecia in an animal which may be predisposed to alopecia; and/or (ii) inhibiting, retarding, or reducing alopecia; and/or (iii) promoting hair growth; and/or (iv) prolonging the anagen phase of the hair cycle; and/or (v) converting vellus hair to growth as terminal hair.

Terminal hair is coarse, pigmented, long hair in which the bulb of the hair follicle is seated deep in the dermis. Vellus hair, on the other hand, is fine, thin, non-pigmented short hair in which the hair bulb is located superficially in the dermis. As alopecia progresses, the hairs change from the terminal to the vellus type.

"Treating memory impairment" refers to:

(i) preventing memory impairment from occurring in an animal which may be predisposed to memory impairment but has not yet been diagnosed as having it;

(ii) inhibiting memory impairment, i.e., arresting its development;

(iii) relieving memory impairment, i.e., causing its regression; and/or (iv) enhancing memory.

"Enhancing memory performance" refers to improving or increasing the mental faculty by which to register, retain or recall past experiences, knowledge, ideas, sensations, thoughts or impressions.

"Vision" refers to the ability of humans and other animals to process images, and is used interchangeably with "sight", "seeing", and other such terms, without limitation.

"Vision disorder" refers to any disorder that affects or involves vision, including without limitation visual impairment, orbital disorders, disorders of the lacrimal apparatus, disorders of the eyelids, disorders of the conjunctiva, disorders of the cornea, cataracts, disorders of the uveal tract, disorders of the optic nerve or visual pathways, free radical induced eye disorders and diseases, immunologically-mediated eye disorders and diseases, eye injuries, and symptoms and complications of eye disease, eye disorder, or eye injury.

"Visual impairment" refers to any dysfunction in vision including, without limitation, disturbances or diminution in vision (e.g., binocular, central, peripheral, scotopic), visual acuity for objects near and for, visual field, ocular motility, color perception, adaptation to light and dark, accommodation, refraction, and lacrimation. See *Physicians' Desk Reference (PDR) for Ophthalmology*, 16th Edition, 6:47 (1988).

"Visual system" includes the eyes, the extraocular muscles which control eye position in the bony orbit (eye socket), the optic and other nerves that connect the eyes to the brain, and those areas of the brain that are in neural communication with the eyes.

Unless the context clearly dictates otherwise, the definitions of singular terms may be extrapolated to apply to their plural counterparts as they appear in the application; likewise, the definitions of plural terms may be extrapolated to apply to their singular counterparts as they appear in the application.

Compounds of the Present Invention

The present invention relates to the surprising discovery that the inventive N-substituted cyclic aza derivative compounds are neurotrophic, are able to treat alopecia, are able to treat vision and memory disorders, and are able to treat sensorineural hearing loss. Accordingly, a novel class of cyclic aza derivative compounds is provided. These compounds may be polycyclic. Preferably, the compounds are low molecular weight, small molecule, neurotrophic, and/or N,N'-disubstituted. A preferred feature of the compounds of the present invention is that they do not exert any significant immunosuppressive activity.

The neurotrophic compounds of this invention can be periodically administered to a patient undergoing treatment for neurological disorders or for other reasons in which it is desirable to stimulate neuronal regeneration and growth, such as in various peripheral neuropathies and neurological disorders relating to neurodegeneration. The compounds of this invention can also be administered to mammals other than humans for treatment of various mammalian neurological disorders.

In one embodiment, the compound of the present invention is an N-diketo cyclic aza derivative compound or a pharmaceutically acceptable salt, ester, or solvate thereof. In another embodiment, the compound of the present invention is an N-sulfonyl cyclic aza derivative compound, or a pharmaceutically acceptable salt, ester, or solvate thereof. In a further embodiment, the compound of the present invention is a tertiary N-aminocarbonyl cyclic aza compound, or a pharmaceutically acceptable salt, ester, or solvate thereof. In yet another embodiment, the compound of the present invention is a secondary N-aminocarbonyl cyclic aza compound, or a pharmaceutically acceptable salt, ester, or solvate thereof.

Possible substituents of any alkyl, alkenyl, aryl, heteroaryl, carbocycle or heterocycle group of the compounds of the present invention include, without limitation, $C_1$-$C_9$ straight or branched chain alkyl, $C_2$-$C_9$ straight or branched chain alkenyl, $C_1$-$C_9$ alkoxy, $C_2$-$C_9$ alkenyloxy, phenoxy, benzyloxy, $C_3$-$C_8$ cycloalkyl, $C_5$-$C_7$ cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, and carbocyclic and heterocyclic moieties. Carbocyclic moieties include alicyclic and aromatic structures.

Specific embodiments of the present inventive compounds are presented below in Tables I, II, and III. The present invention contemplates employing the compounds of Tables I, II, and III for use in compositions and methods to treat alopecia and promote hair growth in an animal, for use in compositions and methods to treat a vision disorder, improve vision, treat memory impairment, and enhance memory performance, and for use in compositions and methods to treat a sensorineural hearing loss in an animal, and all the other uses suggested in this specification.

Preferred compounds of formula I are present below in TABLE I.

TABLE I (I)

| No | n | X | $R_1$ | $R_2$ |
|---|---|---|---|---|
| 1 | 1 | O | 5-Phenylpentanoyl | 1,1-Dimethylpropyl |
| 2 | 1 | O | 3-Phenylpropanoyl | 1,1-Dimethylpropyl |
| 3 | 1 | O | 5-(3-Pyridyl)pent-4-ynoyl | 1,1-Dimethylpropyl |
| 4 | 1 | O | 5-(Cyano)pent-4-ynoyl | 1,1-Dimethylpropyl |
| 5 | 1 | O | 4-Phenylbutanoyl | 1,1-Dimethylpropyl |
| 6 | 1 | O | 6-Phenylhexanoyl | 1,1-Dimethylpropyl |
| 7 | 1 | O | 5-(3-Pyridyl)pentanoyl | 1,1-Dimethylpropyl |
| 8 | 1 | O | 3-Phenylpropyl ester | 1,1-Dimethylpropyl |
| 9 | 1 | O | 3-(3-Pyridyl)propyl ester | 1,1-Dimethylpropyl |
| 10 | 1 | O | 4-Phenylbutyl ester | 1,1-Dimethylpropyl |
| 11 | 1 | O | 2-Phenylethyl ester | 1,1-Dimethylpropyl |
| 12 | 2 | O | 6-Phenylhexanoyl | 1,1-Dimethylpropyl |
| 13 | 2 | O | 6-(3-Pyridyl)hexanoyl | 1,1-Dimethylpropyl |
| 14 | 2 | O | 3-Phenylpropyl ester | 1,1-Dimethylpropyl |
| 15 | 2 | O | 4-Phenylbutyl ester | 1,1-Dimethylpropyl |
| 16 | 2 | O | 5-Phenylpentyl ester | 1,1-Dimethylpropyl |
| 17 | 2 | O | 4-(3-Pyridyl-butyl ester | 1,1-Dimethylpropyl |
| 18 | 2 | O | 5-Phenylpentanoyl | 1,1-Dimethylpropyl |
| 19 | 1 | O | COOH | 3,4,5-trimethylphenyl |
| 20 | 2 | O | COOH | 3,4,5-trimethylphenyl |
| 21 | 1 | O | COOH | tert-butyl |
| 22 | 3 | O | COOH | tert-butyl |
| 23 | 1 | O | COOH | cyclopentyl |
| 24 | 2 | O | COOH | cyclopentyl |
| 25 | 3 | O | COOH | cyclopentyl |
| 26 | 1 | O | COOH | cyclohexyl |
| 27 | 2 | O | COOH | cyclohexyl |

TABLE I-continued (I)

| No | n | X | $R_1$ | $R_2$ |
|---|---|---|---|---|
| 28 | 3 | O | COOH | cyclohexyl |
| 29 | 1 | O | COOH | cycloheptyl |
| 30 | 2 | O | COOH | cycloheptyl |
| 31 | 3 | O | COOH | cycloheptyl |
| 32 | 1 | O | COOH | 2-thienyl |
| 33 | 2 | O | COOH | 2-thienyl |
| 34 | 3 | O | COOH | 2-thienyl |
| 35 | 1 | O | COOH | 2-furyl |
| 36 | 2 | O | COOH | 3-furyl |
| 37 | 3 | O | COOH | 4-furyl |
| 38 | 3 | O | COOH | phenyl |
| 39 | 1 | O | COOH | 1,1-dimethylpentyl |
| 40 | 2 | O | COOH | 1,1-dimethylhexyl |
| 41 | 3 | O | COOH | ethyl |
| 42 | 1 | O | $SO_3H$ | 1,1-dimethylpropyl |
| 43 | 1 | O | CN | 1,1-dimethylpropyl |
| 44 | 1 | O | tetrazole | 1,1-dimethylpropyl |
| 45 | 1 | O | $CONH_2$ | 1,1-dimethylpropyl |
| 46 | 2 | O | $CONH_2$ | 1,1-dimethylpropyl |
| 47 | 1 | O | COOH | α-methylbenzyl |
| 48 | 2 | O | COOH | 4-methylbenzyl |
| 49 | 1 | O | tetrazole | benzyl |
| 50 | 1 | O | $SO_3H$ | α-methylbenzyl |
| 51 | 1 | O | $SO_2HNMe$ | benzyl |
| 52 | 1 | O | CN | α-methylbenzyl |
| 53 | 1 | O | $PO_3H_2$ | 4-methylbenzyl |
| 54 | 2 | O | COOH | benzyl |
| 55 | 2 | O | COOH | α-methylbenzyl |
| 56 | 2 | O | COOH | 4-methylbenzyl |
| 57 | 2 | O | COOH | cyclohexyl |
| 58 | 2 | O | $PO_2HEt$ | i-propyl |
| 59 | 2 | O | $PO_3HPropyl$ | ethyl |
| 60 | 2 | O | $PO_3(Et)_2$ | methyl |
| 61 | 2 | O | methyl ester | tert-butyl |
| 62 | 1 | O | ethyl ester | n-pentyl |
| 63 | 2 | O | propyl ester | n-hexyl |
| 64 | 1 | O | butyl ester | cyclohexyl |
| 65 | 1 | O | pentyl ester | cyclopentyl |
| 66 | 1 | O | hexyl ester | n-heptyl |
| 67 | 1 | O | S-Me | n-octyl |
| 68 | 1 | O | S-Et | n-nonyl |
| 69 | 2 | O | S-propyl | 2-indolyl |
| 70 | 2 | O | S-butyl | 2-furyl |
| 71 | 2 | O | NHCOMe | 2-thiazolyl |
| 72 | 2 | O | NHCOEt | 2-thienyl |
| 73 | 1 | O | CONH(O)Me | benzyl |
| 74 | 1 | O | CONH(O)Et | a-methylphenyl |
| 75 | 1 | O | CONH(O)propyl | 4-methylphenyl |
| 76 | 3 | O | $CONHNHSO_2Me$ | benzyl |
| 77 | 3 | O | $CONHNHSO_2Et$ | α-methylphenyl |
| 78 | 3 | O | $CONHSO_2Me$ | 4-methylphenyl |
| 79 | 1 | O | $CONHNHSO_2Et$ | phenyl |
| 80 | 2 | O | CON(Me)CN | α-methylphenyl |
| 81 | 1 | O | CON(Et)CN | 4-methylphenyl |
| 82 | 1 | O | COOH | 1,1-dimethylpropyl |
| 83 | 2 | O | COOH | 1,1-dimethylpropyl |
| 84 | 2 | O | 5-(3-pyridyl)pentyl ester | 1,1-dimethylpropyl |
| 85 | 1 | O | 4-(3-pyridyl)-3-butynyl ester | 1,1-dimethylpropyl |
| 86 | 1 | O | 3-butynyl ester | 1,1-dimethylpropyl |
| 87 | 1 | O | 5-phenylpentyl ester | 1,1-dimethylpropyl |
| 88 | 1 | O | 4-(3-pyridyl)butyl ester | 1,1-dimethylpropyl |
| 89 | 1 | O | 3-phenylpropyl ester | 1,1-dimethylpentyl |
| 90 | 1 | O | 3-(3-pyridyl)propyl ester | 1,1-dimethylpentyl |
| 91 | 1 | O | 4-phenylbutyl ester | 1,1-dimethylpentyl |
| 92 | 1 | O | 2-phenylethyl ester | 1,1-dimethylpropyl |

TABLE I-continued (I)

| No | n | X | R₁ | R₂ |
|---|---|---|---|---|
| 93 | 1 | O | 2-phenylethanoyl | 1,1-dimethylpropyl |
| 94 | 2 | O | 5-(3-pyridyl)pentanoyl | 1,1-dimethylpropyl |
| 95 | 2 | O | 4-phenylbutanoyl | 1,1-dimethylpropyl |
| 96 | 1 | O | 4-(3-pyridyl)butanoyl | 1,1-dimethylpropyl |
| 97 | 2 | S | 2-phenylethyl ester | 1,1-dimethylpropyl |
| 98 | 2 | S | 3-phenylpropyl ester | 1,1-dimethylpropyl |
| 99 | 1 | S | 3-phenylpropyl ester | 1,1-dimethylpropyl |
| 100 | 1 | S | 2-phenethylester | 1,1-dimethylpropyl |
| 101 | 1 | S | COOH | 1,1-dimethylpropyl |
| 102 | 2 | S | PO₃H₂ | 2-furyl |
| 103 | 1 | S | COOH | phenyl |
| 104 | 2 | S | COOH | 3,4,5-trimethoxyphenyl |

Preferred compounds of TABLE I are named as follows:
3-phenyl-1-propyl 1-(3,3-dimethyl-1,2-dioxopentyl)-2-pyridazinecarboxylate,
4-phenyl-1-n-butyl 1-(3,3-dimethyl-1,2-dioxopentyl)-2-pyridazinecarboxylate,
5-phenyl-1-n-pentyl 1-(3,3-dimethyl-1,2-dioxopentyl)-2-pyridazinecarboxylate,
4-(3-pyridyl) -1-n-butyl 1-(3,3-dimethyl-1, 2-dioxopentyl)-2-pyridazinecarboxylate,
3-phenyl-1-propyl 1-(3,3-dimethyl-1,2-dioxopentyl)-2-pyrazinecarboxylate,
3-(3-pyridyl)-1-propyl 1-(3,3-dimethyl-1,2-dioxopentyl)-2-pyrazinecarboxylate,
4-phenyl-1-n-butyl 1-(3,3-dimethyl-1,2-dioxopentyl)-2-pyrazinecarboxylate,
2-phenyl-1-ethyl 1-(3,3-dimethyl-1,2-dioxopentyl)-2-pyrazinecarboxylate,
2-[(4-phenylbutyl)carbonyl]-1-(3,3-dimethyl-1,2-dioxopentyl)pyridazine,
2-[(2-phenylethyl)carbonyl]-1-(3,3-dimethyl-1,2-dioxopentyl)pyridazine,
2-[(5-phenylpentyl)carbonyl]-1-(3,3-dimethyl-1,2-dioxopentyl)piperazine,
2-[(5-(3-pyridyl)pentyl)carbonyl]-1-(3,3-dimethyl-1,2-dioxopentyl)piperazine,
2-[(4-phenylbutyl)carbonyl]-1-(3,3-dimethyl-1,2-dioxopentyl)piperazine,
2-[(3-phenylpropyl)carbonyl]-1-(3,3-dimethyl-1,2-dioxopentyl)pyridazine,
2-[(5-phenylpentyl)carbonyl]-1-(3,3-dimethyl-1,2-dioxopentyl)pyridazine, and
2-[(4-(3-pyridyl)butyl)carbonyl]-1-(3,3-dimethyl-1,2-dioxopentyl)pyridazine.

In some embodiments, the compounds are selected from
3,3-dimethyl-N-[2-(5-phenylpentanoyl)-tetrahydro-1H-1-pyrazolyl]-1,2-pentanedione;
3,3-dimethyl-N-[2-(3-phenylpropanoyl)tetrahydro-1H-1-pyrazolyl]-1,2-pentanedione;
3,3-dimethyl-1-[2-(5-(3-pyridyl)pent-4-ynoyl)-pyrazolidinyl]pentane-1,2-dione;
3,3-dimethyl-1-[2-(5-(cyano)pent-4-ynoyl)pyrazolidinyl]-pentane-1,2-dione;
3,3-dimethyl-1-[2-(4-phenylbutanoyl)pyrazolidinyl]-pentane-1,2-dione;
3,3-dimethyl-1-[2-(6-phenylhexanoyl)pyrazolidinyl]-pentane-1,2-dione;
3,3-dimethyl-1-[2-(5-(3-pyridyl)pentanoyl)-pyrazolidinyl]pentane-1,2-dione;
3-phenylpropyl 2-(3,3-dimethyl-2-oxopentanoyl)-pyrazolidinecarboxylate;
3-(3-pyridyl)propyl 2-(3,3-dimethyl-2-oxopentanoyl) pyrazolidinecarboxylate;
4-phenylbutyl 2-(3,3-dimethyl-2-oxopentanoyl)-pyrazolidinecarboxylate;
2-phenylethyl 2-(3,3-dimethyl-2-oxopentanoyl)-pyrazolidinecarboxylate;
3,3-dimethyl-1-[2-(6-phenylhexanoyl)perhydro-pyridazinyl]pentane-1,2-dione;
3,3-dimethyl-1-[2-(6-(3-pyridyl)hexanoyl)-perhydropyridazinyl]pentane-1,2-dione;
3-phenylpropyl 2-(3,3-dimethyl-2-oxopentanoyl)-perhydropyridazinecarboxylate;
4-phenylbutyl 2-(3,3-dimethyl-2-oxopentanoyl)perhydropyridazinecarboxylate;
5-phenylpentyl 2-(3,3-dimethyl-2-oxopentanoyl)-perhydropyridazinecarboxylate;
4-(3-pyridyl)butyl 2-(3,3-dimethyl-2-oxopentanoyl)-perhydropyridazinecarboxylate;
3,3-dimethyl-1-[2-((5-phenyl)pentanoyl)perhydro-pyridazinyl]pentane-1,2-dione; and pharmaceutically acceptable salts, esters and solvates thereof.

Preferred compounds of formula II are present below in TABLE II.

TABLE II (II)

| No. | n | R₁ | R₂ |
|---|---|---|---|
| 105 | 1 | 3-Phenylpropyl ester | benzyl |
| 106 | 2 | 4-Phenylbutyl ester | benzyl |
| 107 | 1 | 5-Phenylpentanoyl | benzyl |
| 108 | 1 | COOH | benzyl |
| 109 | 1 | COOH | α-methylbenzyl |
| 110 | 1 | COOH | 4-methylbenzyl |
| 111 | 1 | tetrazole | benzyl |
| 112 | 1 | SO₃H | α-methylbenzyl |
| 113 | 1 | SO₂HNMe | benzyl |
| 114 | 1 | CN | α-methylbenzyl |
| 115 | 1 | PO₃H₂ | 4-methylbenzyl |
| 116 | 2 | COOH | benzyl |
| 117 | 2 | COOH | α-methylbenzyl |
| 118 | 2 | COOH | 4-methylbenzyl |
| 119 | 2 | COOH | 3,4,5-trimethoxyphenyl |
| 120 | 2 | COOH | cyclohexyl |
| 121 | 2 | PO₂HEt | i-propyl |
| 122 | 2 | PO₃HPropyl | ethyl |
| 123 | 2 | PO₃(Et)₂ | methyl |
| 124 | 2 | methyl ester | tert-butyl |
| 125 | 2 | ethyl ester | n-pentyl |
| 126 | 2 | propyl ester | n-hexyl |
| 127 | 1 | butyl ester | cyclohexyl |
| 128 | 1 | pentyl ester | cyclopentyl |
| 129 | 1 | hexyl ester | n-heptyl |

TABLE II-continued

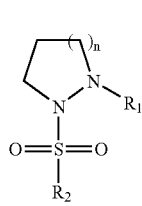

(II)

| No. | n | $R_1$ | $R_2$ |
|---|---|---|---|
| 130 | 1 | S-Me | n-octyl |
| 131 | 1 | S-Et | n-nonyl |
| 132 | 2 | S-propyl | 2-indolyl |
| 133 | 2 | S-butyl | 2-furyl |
| 134 | 2 | NHCOMe | 2-thiazolyl |
| 135 | 2 | NHCOEt | 2-thienyl |
| 136 | 1 | CONH(O)Me | benzyl |
| 137 | 1 | CONH(O)Et | α-methylphenyl |
| 138 | 1 | CONH(O)propyl | 4-methylphenyl |
| 139 | 2 | COOH | benzyl |
| 140 | 2 | COOH | α-methylphenyl |
| 141 | 2 | COOH | 4-methylphenyl |
| 142 | 3 | CONHNHSO$_2$Me | benzyl |
| 143 | 3 | CONHNHSO$_2$Et | α-methylphenyl |
| 144 | 3 | CONHSO$_2$Me | 4-methylphenyl |
| 145 | 2 | CONHNHSO$_2$Et | phenyl |
| 146 | 2 | CON(Me)CN | α-methylphenyl |
| 147 | 2 | CON(Et)CN | 4-methylphenyl |

Preferred compounds of TABLE II are named as follows:
4-phenyl-1-n-butyl 1-(phenylmethyl)sulfonyl-2-pyridazinecarboxylate, and
3-phenyl-1-propyl 1-(phenylmethyl)sulfonyl-2-pyrazinecarboxylate.

In some embodiments, the compounds are selected from
3-phenylpropyl 2-[benzylsulfonyl]pyrazolidine-carboxylate;
4-phenylbutyl 2-[benzylsulfonyl]perhydropyridazine-carboxylate;
1-(5-phenylpentanoyl)-2-(benzylsulfonyi)tetrahydro-1H-1-pyrazole; and pharmaceutically acceptable salts, esters and solvates thereof.

Preferred compounds of formula III are present below in TABLE III.

TABLE III

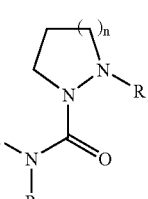

(III)

| No. | n | $R_1$ | $R_4$ | $R_5$ |
|---|---|---|---|---|
| 148 | 1 | 5-Phenylpentanoyl | cyclohexyl | cyclohexyl |
| 149 | 1 | COOH | cyclohexyl | methyl |
| 150 | 1 | COOH | cyclohexyl | ethyl |
| 151 | 1 | COOH | cyclohexyl | propyl |
| 152 | 1 | COOH | cyclohexyl | butyl |

Preferred compounds of formula IV are present below in TABLE IV.

TABLE IV

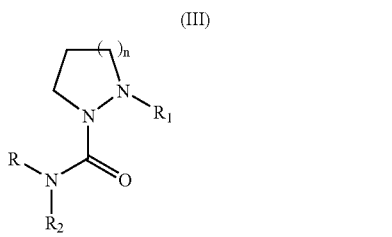

(IV)

| No. | n | $R_1$ | $R_2$ |
|---|---|---|---|
| 153 | 1 | 3-phenylpropyl ester | cyclohexyl |
| 154 | 2 | 4-phenylbutyl ester | cyclohexyl |
| 155 | 1 | 5-phenylpentanoyl | cyclohexyl |
| 156 | 1 | COOH | cyclohexyl |
| 157 | 1 | COOH | α-methylbenzyl |
| 158 | 1 | COOH | 4-methylbenzyl |
| 159 | 1 | tetrazole | benzyl |
| 160 | 1 | SO$_3$H | α-methylbenzyl |
| 161 | 1 | SO$_2$HNMe | benzyl |
| 162 | 1 | CN | α-methylbenzyl |
| 163 | 1 | PO$_3$H$_2$ | 4-methylbenzyl |
| 164 | 2 | COOH | benzyl |
| 165 | 2 | COOH | α-methylbenzyl |
| 166 | 2 | COOH | 2-butyl |
| 167 | 2 | COOH | cyclohexyl |
| 168 | 2 | PO$_2$HEt | i-propyl |
| 169 | 2 | PO$_3$HPropyl | ethyl |
| 170 | 2 | PO$_3$(Et)$_2$ | methyl |
| 171 | 2 | Methyl ester | tert-butyl |
| 172 | 2 | Ethyl ester | n-pentyl |
| 173 | 2 | propyl ester | n-hexyl |
| 174 | 1 | butyl ester | cyclohexyl |
| 175 | 1 | pentyl ester | cyclopentyl |
| 176 | 1 | hexyl ester | heptyl |
| 177 | 1 | SMe | n-octyl |
| 178 | 1 | SEt | n-hexyl |
| 179 | 2 | S-propyl | n-hexyl |
| 180 | 2 | S-butyl | n-hexyl |
| 181 | 2 | NHCOMe | n-hexyl |
| 182 | 2 | NHCOEt | 2-thienyl |
| 183 | 1 | CONH(O)Me | benzyl |
| 184 | 1 | CONH(O)Et | α-methylphenyl |
| 185 | 1 | CONH(O)propyl | 4-methylphenyl |
| 186 | 2 | COOH | benzyl |
| 187 | 2 | COOH | α-methylphenyl |
| 188 | 2 | COOH | 4-methylphenyl |
| 189 | 3 | CONHNHSO$_2$Me | benzyl |
| 190 | 3 | CONHNHSO$_2$Et | α-methylphenyl |
| 191 | 3 | CONHSO$_2$Me | 4-methylphenyl |
| 192 | 2 | CONHNHSO$_2$Et | phenyl |
| 193 | 2 | CON(Me)CN | α-methylphenyl |
| 194 | 2 | CON(Et)CN | 4-methylphenyl |
| 195 | 1 | 3-phenylpropyl ester | cyclohexyl |

Preferred compounds of TABLE IV are named as follows:
4-phenyl-1-n-butyl 1-(cyclohexyl)carbamoyl-2-pyridazinecarboxylate, and
3-phenyl-1-propyl 1-(cyclohexyl)carbamoyl-2-pyrazinecarboxylate.

Representative compounds of the present invention are set forth below.

| No. | Structure | Name |
|---|---|---|
| 1 | 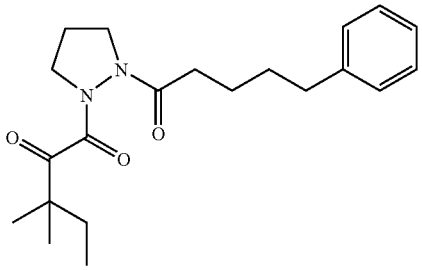 | 3,3-dimethyl-N-[2-(5-phenylpentanoyl)-tetrahydro-1H-1-pyrazolyl]-1,2-pentanedione |
| 2 | 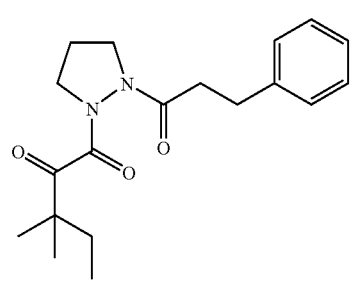 | 3,3-dimethyl-N-[2-(3-phenylpropanoyl)tetrahydro-1H-1-pyrazolyl]-1,2-pentanedione |
| 3 | 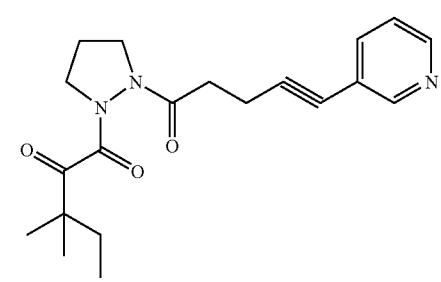 | 3,3-dimethyl-1-[2-(5-(3-pyridyl)pent-4-ynoyl)-pyrazolidinyl]-pentane-1,2-dione |
| 4 | 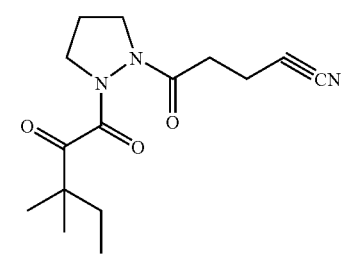 | 3,3-dimethyl-1-[2-(5-(cyano)pent-4-ynoyl)-pyrazolidinyl]-pentane-1,2-dione |
| 5 | 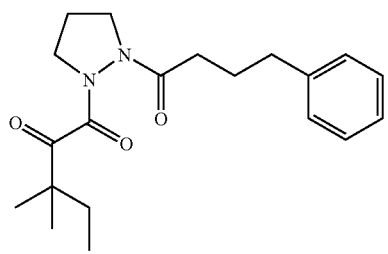 | 3,3-dimethyl-1-[2-(4-phenylbutanoyl)-pyrazolidinyl]pentane-1,2-dione |

-continued

| No. | Structure | Name |
|---|---|---|
| 6 | 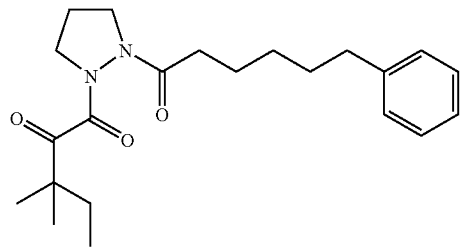 | 3,3-dimethyl-1-[2-(6-phenylhexanoyl)-pyrazolidinyl]pentane-1,2-dione |
| 7 | 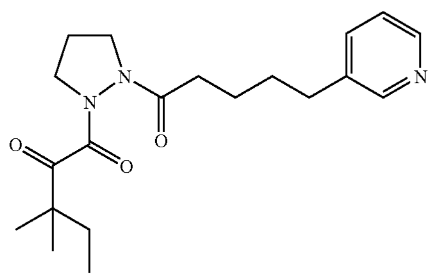 | 3,3-dimethyl-1-[2-(5-(3-pyridyl)pentanoyl)-pyrazolidinyl]pentane-1,2-dione |
| 8 | 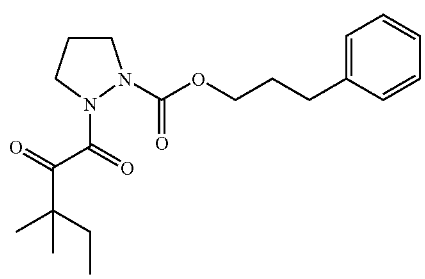 | 3-phenylpropyl 2-(3,3-dimethyl-2-oxopentanoyl)-pyrazolidinecarboxylate |
| 9 | 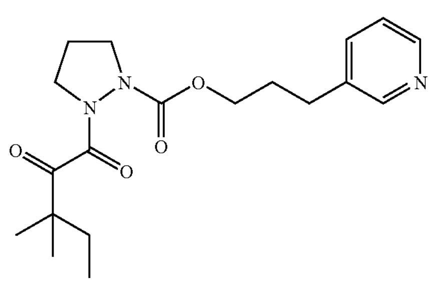 | 3-(3-pyridyl)propyl 2-(3,3-dimethyl-2-oxopentanoyl)-pyrazolidinecarboxylate |
| 10 | 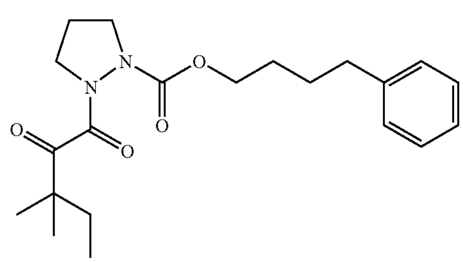 | 4-phenylbutyl 2-(3,3-dimethyl-2-oxopentanoyl)-pyrazolidinecarboxylate |

| No. | Structure | Name |
|---|---|---|
| 11 | 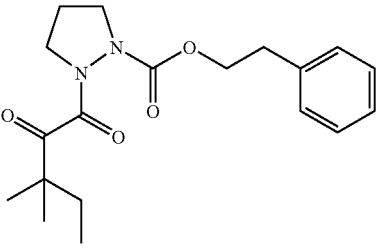 | 2-phenylethyl 2-(3,3-dimethyl-2-oxopentanoyl)-pyrazolidinecarboxylate |
| 12 | 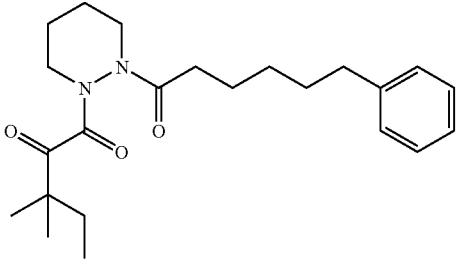 | 3,3-dimethyl-1-[2-(6-phenylhexanoyl)-perhydropyridazinyl]-pentane-1,2-dione |
| 13 | 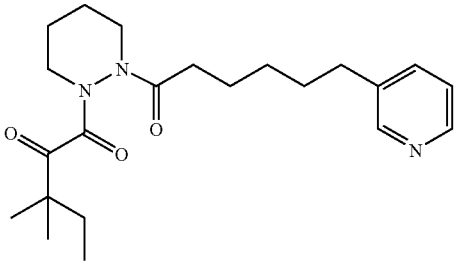 | 3,3-dimethyl-2-[2-(6-(3-pyridyl)hexanoyl)-perhydropyridazinyl]-pentane-1,2-dione |
| 14 | 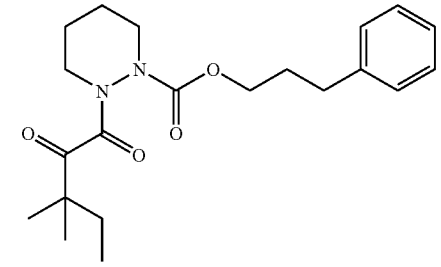 | 3-phenylpropyl 2-(3,3-dimethyl-2-oxopentanoyl)-perhydropyridazine-carboxylate |
| 15 | 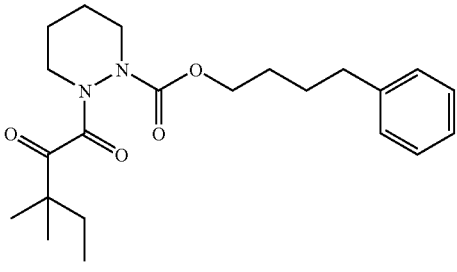 | 4-phenylbutyl 2-(3,3-dimethyl-2-oxopentanoyl)perhydro-pyridazinecarboxylate |

-continued

| No. | Structure | Name |
|---|---|---|
| 16 | 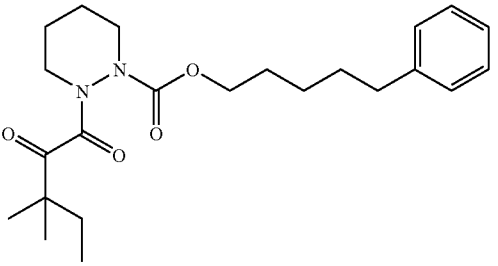 | 5-phenylpentyl 2-(3,3-dimethyl-2-oxopentanoyl)perhydro-pyridazinecarboxylate |
| 17 | 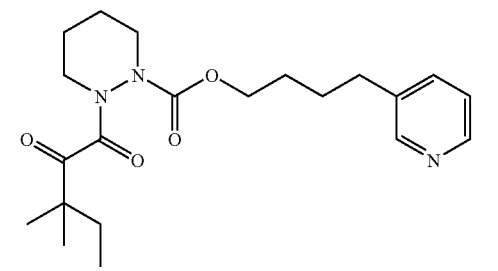 | 4-(3-pyridyl)butyl 2-(3,3-dimethyl-2-oxopentanoyl)-perhydropyridazine-carboxylate |
| 18 | 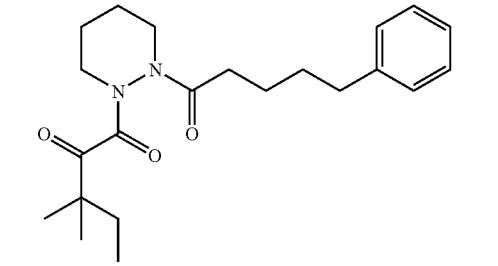 | 3,3-dimethyl-1-[2-({5-phenyl)pentanoyl)-perhydropyridazinyl]-pentane-1,2-dione |
| 105 | 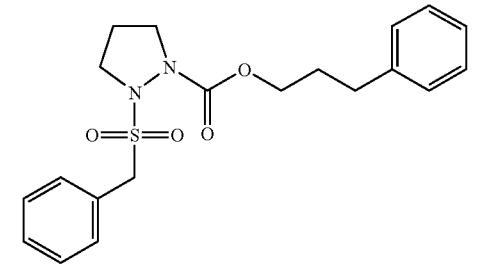 | 3-phenylpropyl 2-[benzylsulfonyl]-pyrazolidinecarboxylate |
| 106 | 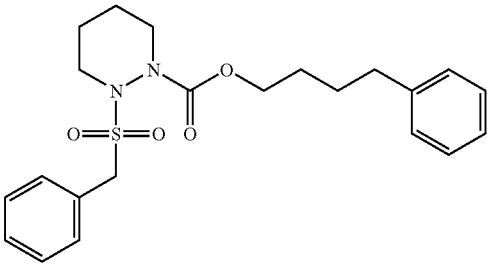 | 4-phenylbutyl 2-[benzylsunfonyl]-perhydropyridazine-carboxylate |

-continued

| No. | Structure | Name |
|---|---|---|
| 107 | 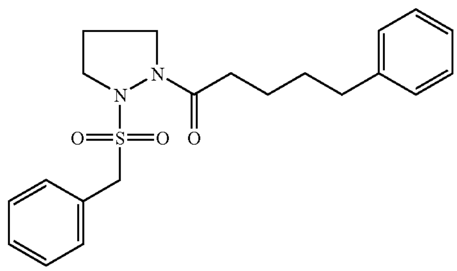 | 1-(5-phenylpentanoyl)-2-(benzylsulfonyl)-tetrahydro-1H-1-pyrazole |
| 153 | 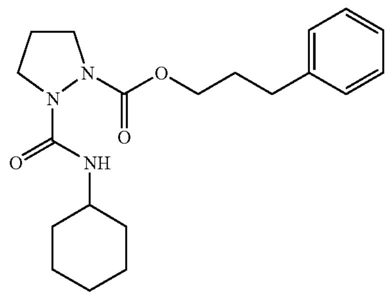 | 3-phenylpropyl 2-(N-cyclohexylcarbamoyl)-pyrazolidinecarboxylate |
| 154 | 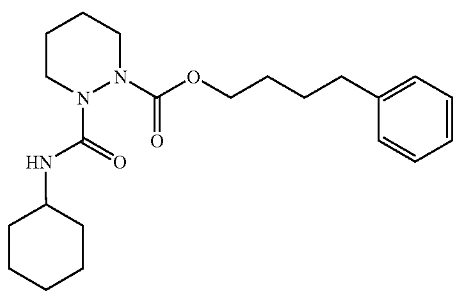 | 4-phenylbutyl 2-(N-cyclohexylcarbamoyl)-perhydropyridazine-carboxylate |
| 155 | 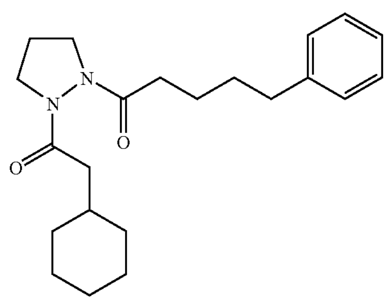 | 1-(5-phenylpentanoyl)-2-(N-cyclohexyl-carbamoyl)tetrahydro-1H-1-pyrazole |
| 148 | 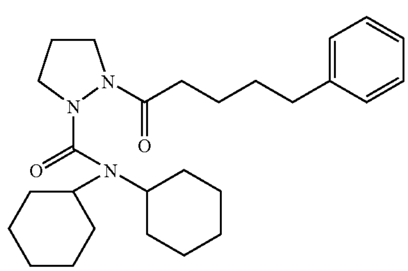 | 1-(5-phenylpentanoyl)-2-(N,N-dicyclohexyl-carbamoyl)tetrahydro-1H-1-pyrazole |

Other compounds which are cyclic aza derivative compounds within the scope of the present invention are those compounds which may possess immunosuppressive, non-immunosuppressive, or other activities as long as they also are useful in treating a disease. In particular, other cyclic aza derivative compounds falling within the scope of the present invention are useful for preventing and/or treating neurological disorders, including physically damaged nerves and neurodegenerative diseases; in treating alopecia and promoting hair growth; in treating vision disorders and/or improving vision; in treating memory impairment and/or enhancing memory performance; and/or in treating sensorineural hearing loss.

The compounds of this invention may possess at least one asymmetric center and thus can be produced as mixtures of stereoisomers or as individual R- and S-stereoisomers. The individual enantiomers may be obtained by using an optically active starting material, by resolving a racemic or non-racemic mixture of an intermediate at some appropriate stage of the synthesis, or by resolving a compound of the present invention. It is understood that the individual R- and S-stereoisomers as well as mixtures (racemic and non-racemic) of stereoisomers are encompassed by this invention.

Pharmaceutical Compositions of the Present Invention

The present invention also relates to a pharmaceutical composition comprising:
(i) an effective amount of a compound of the present invention, as defined above; and
(ii) a pharmaceutically acceptable carrier.

Preferably, the compound is present in an effective amount for effecting a neuronal activity.

The present invention also relates to a pharmaceutical composition comprising:
(i) an effective amount of a compound of the present invention, as defined above, for treating neurodegenerative diseases, neurological disorders, and nerve damage, or promoting nerve growth in animals; and
(ii) a pharmaceutically acceptable carrier.

The present invention also relates to a pharmaceutical composition comprising:
(i) an effective amount of a compound of the present invention, as defined above, for treating alopecia or promoting hair growth in an animal; and
(ii) a pharmaceutically acceptable carrier.

The present invention also relates to a pharmaceutical composition comprising:
(i) an effective amount of a compound of the present invention, as defined above, for treating a vision disorder, improving vision, treating memory impairment, or enhancing memory performance in an animal; and
(ii) a pharmaceutically acceptable carrier.

The present invention also relates to a pharmaceutical composition comprising:
(i) an effective amount of a compound of the present invention, as defined above, for treating sensorineural hearing loss in an animal; and
(ii) a pharmaceutically acceptable carrier.

In another preferred embodiment, the novel compounds of the present invention can be administered in pharmaceutical compositions additionally containing other neurotrophic agents such as neurotrophic growth factor, brain derived growth factor, glial derived growth factor, cilial neurotrophic factor, insulin growth factor and active truncated derivatives thereof, acidic fibroblast growth factor, basic fibroblast growth factor, platelet-derived growth factors, neurotropin-3 and neurotropin 4/5. The dosage level of other neurotrophic drugs will depend upon the factors stated elsewhere herein and the neurotrophic effectiveness of the drug combination.

Methods of the Present Invention

The present invention further relates to the use of any of the compounds of the present invention, as defined above, and other compounds not specifically mentioned or described herein, in the preparation of a medicament for the treatment of a disease. In particular, the compounds are used in the preparation of a medicament for treating any of the diseases enumerated herein.

The present invention also relates to the use of any of the compounds of the present invention, as defined above, and other compounds not specifically mentioned or described herein, for the treatment of a disease. In particular, the compounds are used for treating any of the diseases enumerated herein.

The present invention also relates to methods of using any the compounds of the present invention, as defined above, and other compounds not specifically mentioned or described herein, for treating any of the diseases enumerated herein.

The discussion below relating to the utility and administration of the compounds of the present invention also applies to the pharmaceutical compositions of the present invention.

Methods for Effecting Neuronal Activities

The novel compounds of the present invention possess an excellent degree of neurotrophic activity. Accordingly, the present invention further relates to a method for effecting a neuronal activity in a mammal, comprising administering to said mammal an effective amount of a compound of the present invention, as defined above.

The neuronal activity that is effected by the inventive method may be selected from the group consisting of stimulation of damaged neurons, promotion of neuronal regeneration, prevention of neurodegeneration, and treatment of a neurological disorder.

Examples of neurological disorders that are treatable by the methods of the present invention include without limitation: trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barré syndrome; multiple sclerosis; stroke and ischemia associated with stroke; neural paropathy; other neurodegenerative diseases; motor neuron diseases; sciatic crush; sciatica; sciatic nerve damage; peripheral neuropathy, particularly neuropathy associated with diabetes; spinal cord injuries; facial nerve crush; Alzheimer's disease; Huntington's disease; and Parkinson's disease.

The inventive method is particularly useful for treating a neurological disorder selected from the group consisting of peripheral neuropathy caused by physical injury or disease state, physical damage to the brain, physical damage to the spinal cord, stroke associated with brain damage, demyelinating disease and neurological disorder relating to neurodegeneration.

Examples of neurological disorders relating to neurodegeneration include Alzheimer's disease, Parkinson's disease, Huntington's disease and amyotrophic lateral sclerosis (ALS).

Methods for Treating Alopecia or Promoting Hair Growth

The present invention further relates to a method for treating alopecia or promoting hair growth in a mammal, comprising administering to the mammal an effective amount of a compound of the present invention, as defined above.

The inventive method is particularly useful for treating male pattern alopecia, alopecia senilis, alopecia areata, alopecia resulting from skin lesions or tumors, alopecia resulting from cancer therapy such as chemotherapy and radiation, and alopecia resulting from systematic disorders such as nutritional disorders and internal secretion disorders.

Methods for Treating Vision Disorders or Improving Vision

The present invention further relates to a method for treating a vision disorder, promoting vision regeneration, or improving vision in a mammal, comprising administering to the mammal an effective amount of a compound of the present invention, as defined above.

The inventive methods are particularly useful for treating various eye disorders including, but not limited to visual disorders, diseases, injuries, and complications, genetic disorders; disorders associated with aging or degenerative vision diseases; vision disorders correlating to physical injury to the eye, head, or other parts of the body resulting from external forces; disorders resulting from environmental factors; disorders resulting from a broad range of diseases; and combinations of any of the above.

In particular, the compositions and methods of the present invention are useful for improving vision, or correcting, treating, or preventing visual (ocular) impairment or dysfunction of the visual system, including permanent and temporary visual impairment, without limitation. The present invention is also useful in preventing and treating ophthalmologic diseases and disorders, treating damaged and injured eyes, and preventing and treating diseases, disorders, and injuries which result in vision deficiency, vision loss, or reduced capacity to see or process images, and the symptoms and complications resulting from same. The eye diseases and disorders which may be treated or prevented by the compositions and methods of the present invention are not limited with regard to the cause of said diseases or disorders. Accordingly, said compositions and methods are applicable whether the disease or disorder is caused by genetic or environmental factors, as well as any other influences. The compositions and methods of the present invention are particularly useful for eye problems or vision loss or deficiency associated with all of the following, without limitation: aging, cellular or physiological degeneration, central nervous system or neurological disorder, vascular defects, muscular defects, and exposure to adverse environmental conditions or substances.

The compositions and methods of the present invention are particularly useful in correcting, treating, or improving visual impairment, without limitation. Visual impairment in varying degrees occurs in the presence of a deviation from normal in one or more functions of the eye, including (1) visual acuity for objects at distance and near; (2) visual fields; and (3) ocular motility without diplopia. See *Physicians' Desk Reference (PDR) for Ophthalmology*, 16th Edition, . . . 6:47 (1988). Vision is imperfect without the coordinated function of all three. Id.

Said compositions and methods of use are also useful in correcting, treating, or improving other ocular functions including, without limitation, color perception, adaptation to light and dark, accommodation, metamorphopsia, and binocular vision. The compositions and methods of use are particularly useful in treating, correcting, or preventing ocular disturbances including, without limitation, paresis of accommodation, iridoplegia, entropion, ectropion, epiphora, lagophthalmos, scarring, vitreous opacities, non-reactive pupil, light scattering disturbances of the cornea or other media, and permanent deformities of the orbit.

The compositions and methods of use of the present invention are also highly useful in improving vision and treating vision loss. Vision loss ranging from slight loss to absolute loss may be treated or prevented using said compositions and methods of use. Vision may be improved by the treatment of eye disorders, diseases, and injuries using the compositions and methods of the invention. However, improvements in vision using the compositions and methods of use are not so limited, and may occur in the absence of any such disorder, disease, or injury.

Methods for Treating Memory Impairment or Enhancing Memory Performance

The present invention further relates to a method for treating memory impairment or enhancing memory performance in a mammal, comprising administering to the mammal an effective amount of a compound of the present invention, as defined above.

Methods for Treating Hearing Loss

The present invention further relates to a method for treating a sensorineural hearing loss in a mammal, comprising administering to the mammal an affective amount of the compound of the present invention, as defined above.

It is further contemplated that administration of an inventive compound will protect hair cells and spiral ganglion neurons from traumatic damage, for example damage caused by noise trauma, acute or chronic treatment with cisplatin and aminoglycoside antibiotics of from damage resulting from a lack of neurotrophic factors resulting from interruption of transport of the factors from the axon to the cell body. Such treatment is expected to allow hair cells and/or auditory neurons to tolerate intermittent insults from either environmental noise trauma or treatment with ototoxins, and to slow down, prevent or reverse the progressive degeneration of the auditory neurons and hair cells which is responsible for hearing loss in pathological conditions such as presbycusis (age-related hearing loss), inherited sensorineural degeneration, and post-idiopathic hearing losses and to preserve the functional integrity of the inner ear. Such treatment will also support the auditory neurons for better and longer performance of cochlear implants.

Methods for Preparing Inventive Compounds

The compounds of the present invention can be readily prepared by standard techniques of organic chemistry, utilizing the general synthetic pathways depicted below in Schemes I and II.

In the preparation of the compounds of the present invention, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed under conditions which will not affect the remaining portion of the molecule, for example by hydrolytic or hydrogenolytic means and the like. Such protection and deprotection steps are conventional in organic chemistry. One skilled in the art is referred to "Protective Groups in Organic Chemistry," McOmie, ed., Plenum Press, New York, N.Y.; and "Protective Groups in Organic Synthesis," Greene, ed., John Wiley & Sons, New York, N.Y. (1981) for the teaching of protective groups which may be useful in the preparation of compounds of the present invention. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can be readily neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

The product and intermediates may be isolated or purified using one or more standard purification techniques, including, for example, one or more of simple solvent evaporation, recrystallization, distillation, sublimation, filtration, chromatography, including thin-layer chromatography, HPLC (e.g. reverse phase HPLC), column chromatography, flash chromatography, radial chromatography, trituration, and the like.

SCHEME I

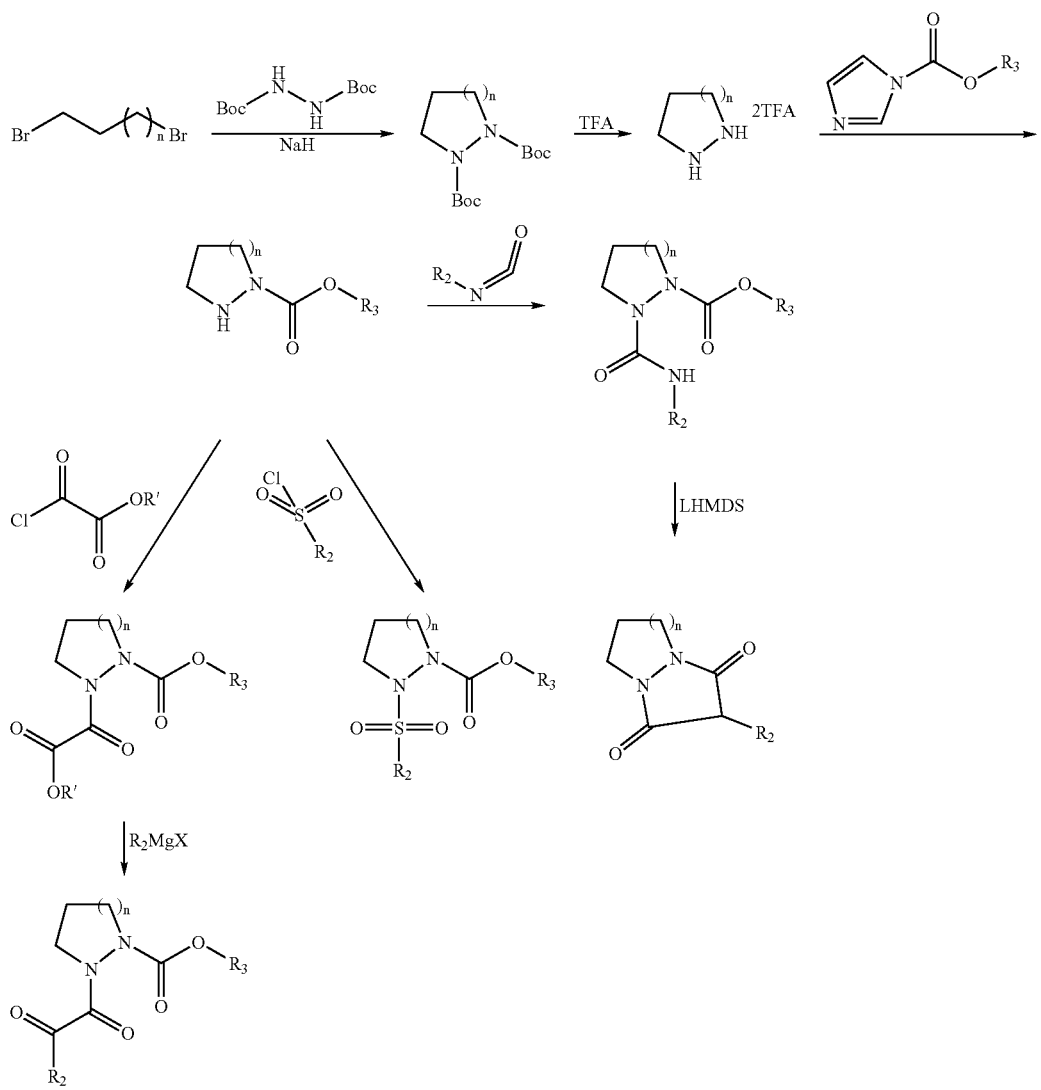

wherein, in Scheme I, n, $R_3$, and $R_2$ are as defined elsewhere throughout the specification; R' is a straight or branched chain alkyl group which is optionally substituted in one or more positions; and X is a halogen, wherein any of these substituents are formed in any chemically reasonable substitution pattern. It is further contemplated as within the scope of the present invention that the chlorine atoms depicted in Scheme I above can be replaced with any other halogen atom.

In particular, the process of scheme I further contemplates activated derivatives of any of the compounds embodied therein, as well as the removal of a protecting group from the product. One skilled in the art would be able to identify various activated derivatives useful in preparing the present inventive compounds. Particularly preferred activated derivatives can include, for example, halo, a lower acyloxy group, a carbodiimide group such as 1-ethyl-3-(3-dimethylaminopropyl) carbodiimide (EDAC), an isobutyrate group, an amino acid anhydride protected amino acid, N-carboxyanhydrides (NCA's), a triazole, a mixed anhydride (see, for example, G. E. Krejcarek and K. L. Tucker, Biochem., Biophys. Res. Commun. 1977, 581, the entire contents of which are hereby incorporated by reference), such as a coupling reagent with dicyclohexyl dicarbodiimide (DCC), acid halides, anhydrides, acid chlorides, acid hydrides, activated esters, nitrenes, isothiocyanates, and acyl cyanides or anhydrides (see Tetrahedron Letters, Volume 18, (1973), pp. 1595-1598, the entire contents of which are hereby incorporated by reference).

SCHEME II

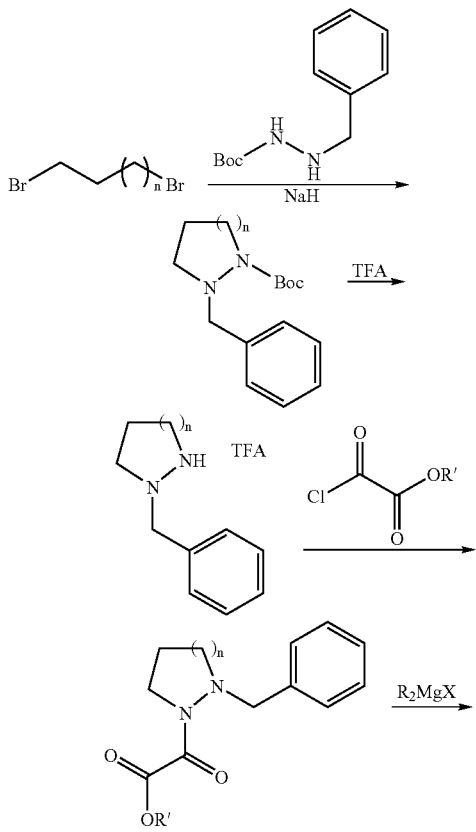

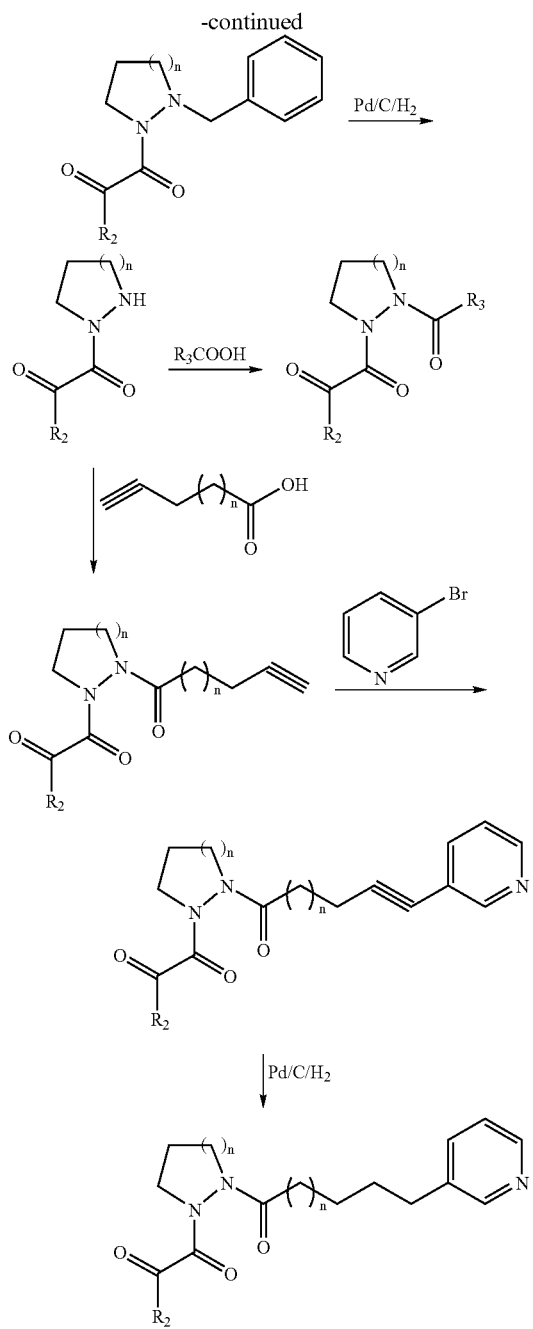

wherein, in Scheme II, n, $R_1$, and $R_2$ are as defined elsewhere throughout the specification; R' is a straight or branched chain alkyl group which is optionally substituted in one or more positions; and X is a halogen, wherein any of these substituents are formed in any chemically reasonable substitution pattern. It is further contemplated as within the scope of the present invention that the benzyl groups depicted in Scheme II above can be replaced with any $R_4$ group, wherein $R_4$ is an alkyl chain substituted with an aryl group; and that the chlorine atoms depicted in Scheme II above can be replaced with any other halogen atom.

In particular, the process of scheme II further contemplates activated derivatives of any of the compounds embodied therein, as well as the removal of a protecting group from the product. One skilled in the art would be able to identify various activated derivatives useful in preparing the present inventive compounds. Particularly preferred activated derivatives can include, for example, halo, a lower acyloxy group, a carbodiimide group such as 1-ethyl-3-(3-dimethylaminopropyl) carbodiimide (EDAC), an isobutyrate group, an amino acid anhydride protected amino acid, N-carboxyanhydrides (NCA's), a triazole, a mixed anhydride (see, for example, G. E. Krejcarek and K. L. Tucker, Biochem., Biophys. Res. Commun. 1977, 581, the entire contents of which are hereby incorporated by reference), such as a coupling reagent with dicyclohexyl dicarbodiimide (DCC), acid halides, anhydrides, acid chlorides, acid hydrides, activated esters, nitrenes, isothiocyanates, and acyl cyanides or anhydrides (see Tetrahedron Letters, Volume 18, (1973), pp. 1595-1598, the entire contents of which are hereby incorporated by reference).

Route of Administration

In the inventive methods, the compounds will generally be administered to a patient in the form of a pharmaceutical formulation. Such formulation preferably includes, in addition to the active agent, a physiologically acceptable carrier and/or diluent. The compounds may be administered by any means known to an ordinarily skilled artisan. For example, the compounds may be administered orally, parenterally, by inhalation spray, topically, rectally, nasally, buccally, vaginally, directly into the middle or inner ear, or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneal, intrathecal, intraventricular, intrasternal, intracranial, intracerebral, intraosseous, infusion, transdermal, and transpulmonary injection or infusion routes.

For oral administration, the compounds of the present invention may be provided in any suitable dosage form known in the art. For example, the compositions may be incorporated into tablets, powders, granules, beads, chewable lozenges, capsules, liquids, aqueous suspensions or solutions, or similar dosage forms, using conventional equipment and techniques known in the art. Tablet dosage forms are preferred. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient.

When preparing dosage form incorporating the compositions of the invention, the compounds may also be blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethylcellulose and sodium starch glycolate; suspending agents, such as povidone, polyvinyl alcohol, and the like; absorbents, such as silicon dioxide; preservatives, such as methylparaben, propylparaben, and sodium benzoate; surfactants, such as sodium lauryl sulfate, polysorbate 80, and the like; colorants such as F.D.& C. dyes and lakes; flavorants; and sweeteners.

Compositions and methods of the invention also may utilize controlled release technology. Thus, for example, the inventive compounds may be incorporated into a hydrophobic polymer matrix for controlled release over a period of days. Such controlled release films are well known to the art. Particularly preferred are transdermal delivery systems. Other examples of polymers commonly employed for this purpose that may be used in the present invention include nondegradable ethylene-vinyl acetate copolymer and degradable lactic acid-glycolic acid copolymers which may be used externally or internally. Certain hydrogels such as poly(hydroxyethylmethacrylate) or poly(vinylalcohol) also may be useful, but for shorter release cycles then the other polymer releases systems, such as those mentioned above.

The compounds of the present invention may be administered in the form of sterile injectable preparations, for example, as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil may be employed including synthetic mono- or di-glycerides. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

The compounds of this invention may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax and polyethylene glycols.

The compounds of this invention may also be administered topically, especially when the conditions addressed for treatment involve areas or organs readily accessible by topical application, including neurological disorders of the eye, the skin, or the lower intestinal tract. Suitable topical formulations are readily prepared for each of these areas.

For topical application to the eye, or ophthalmic use, the compounds can be formulated as micronized suspensions in isotonic, pH adjusted sterile saline, or, preferably, as solutions in isotonic, pH adjusted sterile saline, either with or without a preservative such as benzylalkonium chloride. Alternatively for the ophthalmic uses the compounds may be formulated in an ointment such as petrolatum.

For topical application to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract an be effected in a rectal suppository formulation (see below) or in a suitable enema formulation.

To be effective therapeutically as central nervous system targets, the compounds should readily penetrate the blood-brain barrier when peripherally administered. Compounds which cannot penetrate the blood-brain barrier can be effectively administered by an intraventricular route or other appropriate delivery system suitable for administration to the brain.

Dosage

The compounds and compositions of the present invention may be administered by a single dose, multiple discrete doses or continuous infusion. The compounds are well suited to continuous infusion. Pump means, particularly subcutaneous pump means, are preferred for continuous infusion.

Dose levels on the order of about 0.1 mg to about 10,000 mg of the active ingredient compound, but less than 40 mg/kg where the compound is Suramin, are useful in the treatment of the above conditions, with preferred levels being about 0.1 mg to about 1,000 mg. The specific dose level for any particular patient will vary depending upon a variety of factors, including the activity and the possible toxicity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

The specific dose may be calculated according to considerations of body weight, body surface area or organ size. Further refinement of the calculations necessary to determine the appropriate dosage for treatment involving each of the above mentioned formulations is routinely made by those of ordinary skill in the art and is within the ambit of tasks routinely performed, especially in light of the dosage information and assays disclosed herein. Appropriate dosages may be determined using established assays in conjunction with appropriate dose-response data. One skilled in the art will appreciate that the dosage used in localized formulations of the invention normally will be smaller as compared to that used in a systemic injection or oral administration.

Administration Regimen

For the methods of the present invention, any administration regimen well known to an ordinarily skilled artisan for regulating the timing and sequence of drug delivery can be used and repeated as necessary to effect treatment. Such regimen may include pretreatment and/or co-administration with additional therapeutic agents.

Co-Administration with Other Treatments

The compounds and compositions of the present invention may be used alone or in combination with one or more additional agent(s) for simultaneous, separate or sequential use.

The additional agent(s) may be any therapeutic agent(s) known to an ordinarily skilled artisan, including without limitation: one or more compound(s) of the present invention; and one or more neurotrophic factor(s) selected from the group consisting of neurotrophic growth factor, brain derived growth factor, glial derived growth factor, cilial neutrophic factor, insulin growth factor, acidic fibroblast growth factor, basic fibroblast growth factor, platelet-derived growth factor, neurotropin-3, neurotropin-4 and neurotropin-5; one or more neopsic factors.

The compounds of the present invention can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of a compound of the present invention, as well as one or more pharmaceutical excipients, such as wetting, emulsifying and pH buffering agents.

EXAMPLES

The following examples are illustrative of the present invention and are not intended to be limitations thereon.

Example 1

Synthesis of 4-Phenylbutyl 2-(3,3-dimethyl-2-oxo-pentanoyl)perhydropyridazinecarboxylate (Compound 15)

a. Synthesis of tert-butyl 2-[(tert-butyl)oxycarbonyl]-perhydropyridazinecarboxylate A solution of di-Boc hydrazine (20 g, 84.4 mmol) in 150 DMF was added dropwise to a suspended solution of 6.75 g (168.8 mmol) NaH in 75 ml DMF under nitrogen. After the mixture was stirred for 30 minutes at room temperature, a solution of 1,4 dibromobutane (18.2 g, 84.4 mmol) in 25 ml DMF was added dropwise. The reaction was allowed to stir overnight at room temperature. The reaction was then concentrated, followed by partition between 200 ml $CH_2Cl_2$ and 200 ml water. The aqueous layer was extracted with additional 200 ml $CH_2Cl_2$. The combined organic layers were dried over MgSO4, and filtered and concentrated. The crude product was further purified by silica gel chromatography to yield 20.2 g (82% yield) product. The product was analyzed by GC/MS as pure compound with $M^+$ 286.

b. Synthesis of perhydropyridazine 2.83 ml (36.7 mmol) TFA was added dropwise to a solution of tert-butyl 2-[(tert-butyl)oxycarbonyl]perhydro-pyridazinecarboxylate (1.5 g, 5.2 mmol) in 7 ml $CH_2Cl_2$, and the mixture was stirred overnight. At this time, the reaction was completed and 5.85 ml (42 mmol) triethylamine was added to quench the reaction. The reaction was concentrated and the residue, which contained product, was used without further purification.

c. Synthesis of 4-phenylbutyl perhydropyridazine-carboxylate

A solution containing 1,1'carbonyl diimidazole (0.893 g, 5.5 mmol) in 5 ml $CH_2Cl_2$ was added slowly to a solution of $CH_2Cl_2$ containing phenylbutyl alcohol (0.89 ml, 5.77 mmol). After stirring at room temperature for 1 hour, this solution was then added slowly to a solution containing perhydropyridazine mentioned above. The reaction was allowed to stir for overnight. The crude mixture was then concentrated and used without further purification.

d. Synthesis of methyl 2-oxo-2-{2-[(4-phenylbutyl) oxy-carbonyl]perhydropyridazinyl} acetate A solution of $CH_2Cl_2$ containing previous crude product of 4-phenylbutyl perhydropyridazinecarboxylate from last step was cooled to 0° C., and a solution of methyl oxalyl chloride (0.74 g, 5.77 mmol) in 5 ml $CH_2Cl_2$ was added dropwise over 0.5 hour. The resulting mixture was stirred at 0° C. for 4 hours, and then warmed up to room temperature. The reaction mixture was diluted with 50 ml $CH_2Cl_2$ and washed with water. The organic layer was dried over $MgSO_4$, and filtered and concentrated. The crude product was further purified by silica chromatography to yield 1.8 g (62% overall yield for three steps) product. $^1$H NMR ($CDCl_3$, 400 MHz): δ 1.39 (m, 2H); 1.69 (m, 6H); 2.62 (t, 2H, J=8); 2.83 (m, 1H); 3.10 (m, 1H); 3.79 (s, 3H); 4.16 (m, 3H); 4.31 (m, 1H); 7.22 (m, 5H).

e. Synthesis of 4-phenylbutyl 2-(3,3-dimethyl-2-oxopentanoyl)perhydropyridazine carboxylate A solution of methyl 2-oxo-2-{2-[(4-phenylbutyl)-oxy-carbonyl]perhydropyridazinyl} acetate (1.2 g, 3.45 mmol) in 15 ml dry THF was cooled to −78° C. and treated with 5.2 ml of 1.0 M solution of 1,1-dimethylpropylmagnesium chloride in THF. After stirring the resulting homogeneous mixture at −78° C. for 4 hours, the mixture was poured into saturated ammonium chloride (20 ml) and extracted into ethyl acetate. The organic layer was washed with water, dried and concentrated. The crude material was purified by silica gel column, eluting with 25% ethyl acetate in hexane, to obtain 0.98 g product (73% yield). $R_f$=0.73 (2:1 hexane: EtOAc). $^1$H NMR ($CDCl_3$, 400 MHz): δ 0.81 (t, 3H, J=7.1); 1.13 (s, 3H); 1.20 (s, 3H); 1.64 (m, 10H); 2.64 (m, 2H); 2.86 (m, 1H); 3.20 (m, 1H); 3.99 (m, 1H); 4.19 (m, 2H); 4.35 (m, 1H); 7.24 (m, 5H). Anal. Calcd. for $C_{22}H_{32}N_2O_4$: C, 68.01; H, 8.30; N, 7.21. Found: C, 68.10; H, 8.29; N, 7.15.

Example 2

Synthesis of 4-Phenylbutyl 2-[benzylsulfonyl]-perhydropyridazinecarboxylate (Compound 106)

A solution of α-toluene sulfonyl chloride (1.12 g, 5.77 mmol) in $CH_2Cl_2$ was added to a $CH_2Cl_2$ solution containing 4-phenylbutyl perhydropyridazinecarboxylate (1.37 g, 5.2 mmol) and triethylamine (0.83 ml, 6 mmol). The reaction was stirred overnight at room temperature under nitrogen atmosphere, and then diluted to 50 ml $CH_2Cl_2$. The organic layer was washed with water, dried, and concentrated. The crude material was purified by silica gel column to yield 1.4 g (64%) final product as clear oil. $R_f$=0.60 (2:1 hexane: EtOAc). $^1$H NMR ($CDCl_3$, 400 MHz): δ 1.68 (m, 8H); 2.67 (m, 2H); 2.90 (m, 1H); 3.38 (m, 2H); 4.22 (m, 5H); 7.32 (m, 10H). Anal. Calcd. for $C_{22}H_{28}N_2S_1O_4$: C, 63.44; H, 6.78; N, 6.73, S, 7.70. Found: C, 63.86; H, 6.83; N, 6.41, S, 7.58.

Example 3

Synthesis of 4-Phenylbutyl 2-(N-cyclohexylcarbamoyl)-perhydropyridazinecarboxylate (Compound 153)

Cyclohexylisocyanate (0.38 g, 3.0 mmol) was added to a $CH_2Cl_2$ solution containing 4-phenylbutyl perhydropyridazinecarboxylate (0.72 g, 2.75 mmol) and triethylamine (0.42 ml, 3 mmol). The reaction was stirred overnight at room temperature under nitrogen atmosphere, and then diluted to 50 ml $CH_2Cl_2$. The organic layer was washed with water, dried, and concentrated. The crude material was purified by silica gel column to yield 0.95 g (89%) final product as clear oil. $R_f$=0.28 (2:1 hexane:EtOAc). $^1$H NMR ($CDCl_3$, 400 MHz): δ 1.10 (m, 3H); 1.33 (m, 3H); 1.69 (m, 10H); 1.88 (m, 2H); 2.62 (m, 2H); 2.72 (m, 1H); 2.87 (m, 1H); 3.60 (m, 1H); 4.13 (m, 3H); 4.38 (m, 1H); 5.11 (d, 1H, J=8.3); 7.23 (m, 5H). Anal. Calcd. for $C_{22}H_{28}N_3O_3$-0.14$H_2O$: C, 67.75; H, 8.60; N, 10.77. Found: C, 67.75; H, 8.45; N, 10.90.

Example 4

Synthesis of 3,3-Dimethyl-1-[2-(6-phenylhexanoyl) perhydropyridazinyl]pentane-1,2-dione (Compound 12) using Scheme 2 a. Synthesis of (tert-butoxy)-N-[benzylamino]formamide

A solution of benzyl carbazate (25 g, 150.4 mmol), Boc anhydride (42.7 g, 195.5 mmol), triethylamine (19.8 g, 195.5 mmol), DMAP (0.9 g, 7.5 mmol) in 650 ml $CH_2Cl_2$ was stirred for 24 hours. The mixture was concentrated and purified by silica gel column, eluting with 20% ethyl acetate in hexane, to yield 36 g (90%) product. $^1$H NMR ($CDCl_3$, 400 MHz): δ 1.40 (m, 9H); 5.25 (m, 2H); 7.36 (m, 5H).

b. Synthesis of tert-butyl 2-benzylperhydropyridazine-carboxylate

A solution of (tert-butoxy)—N-[benzylamino]formamide (35 g, 131 mmol) in 300 DMF was added dropwise to a suspended solution of 6.3 g (262 mmol) NaH in 130 ml DMF under nitrogen. After the mixture was stirred for 30 minutes at room temperature, a solution of 1,4 dibromobutane (28.4 g, 131 mmol) in 50 ml DMF was added dropwise. The reaction was allowed to stir overnight at room temperature. The reaction was then concentrated, followed by partition between 200 ml $CH_2Cl_2$ and 200 ml water. The aqueous layer was extracted with additional 200 ml $CH_2Cl_2$. The combined organic layers were dried over $MgSO_4$, and filtered and concentrated. The crude product was further purified by silica chromatography to yield 13.5 g (32% yield) product. $^1$H NMR ($CDCl_3$, 400 MHz): δ 1.46 (m, 9H); 1.64 (m, 4H); 2.88 (m, 2H); 4.20 (m, 2H); 5.16 (m, 2H); 7.31 (m, 5H).

c. Synthesis of methyl 2-oxo-2-[2-benzylperhydropyridazinyl]acetate

20% TFA in $CH_2Cl_2$ was cooled to 0° C. and added dropwise to a solution of tert-butyl 2-benzylperhydropyridazinecarboxylate (13.34 g, 41.7 mmol) in 10 ml $CH_2Cl_2$. The mixture was stirred overnight. At this time, the mixture was cooled to 0° C. and 12.66 ml (125 mmol) triethylamine was added, followed by addition dropwise of methyl oxalyl chloride (5.62, 45.9 mmol) in 5 ml $CH_2Cl_2$. The mixture was allowed to stirred 2 hours at 0° C. and warmed up to room temperature overnight. The reaction was diluted with addition of $CH_2Cl_2$ and washed with water. The organic layer was dried over $MgSO_4$, and filtered and concentrated. The crude product was further purified by silica chromatography to yield 9.2 g (72.4% yield) product as clear oil. $^1$H NMR ($CDCl_3$, 400 MHz): δ 1.72 (m, 4H); 2.85 (m, 1H); 3.12 (m, 1H); 3.67 (s, 3H); 4.15 (m, 1H); 4.35 (m, 1H); 5.20 (m, 2H); 7.35 (m, 5H)

d. Synthesis of 3,3-dimethyl-1-[2-benzylperhydropyridazinyl]pentane-1,2-dione A solution of methyl 2-oxo-2-[2-benzylperhydropyridazinyl]acetate (9.0 g, 29.4 mmol) in 30 ml dry THF was cooled to −78° C. and treated with 35 ml of 1.0 M solution of 1,1-dimethylpropylmagnesium chloride in THF. After stirring the resulting homogeneous mixture at for 5 hours, the mixture was poured into saturated ammonium chloride (150 ml) and extracted into ethyl acetate. The organic layer was washed with water, dried and concentrated. The crude material was purified by silica gel column, eluting with 10% ethyl acetate in hexane, to obtain 7.0 g product (69% yield) as clear oil. $^1$H NMR (CDCl$_3$, 400 MHz): δ 0.76 (t, 3H, J=7.0); 1.06 (s, 6H) 1.69 (m, 6H); 2.80 (m, 1H); 3.15 (m, 1H), 4.03 (m, 1H); 4.13 (m, 1H); 5.18 (m, 2H), 7.36 (m, 5H).

e. Synthesis of 3,3-dimethyl-1-perhydropyridazinyl-pentane-1,2-dione 1 g 10% Pd/C was added to a solution of 3,3-dimethyl-1-[2-benzylperhydropyridazinyl] pentane-1,2-dione (7.0 g, 20.2 mmol) in 70 ml EtOH. The mixture was under hydrogenation at room pressure (1 atm) overnight. The product was obtained as white solid after filtering Pd catalyst and concentration (3.8 g, 89%). $^1$H NMR (CDCl$_3$, 400 MHz): δ 0.88 (t, 3H, J=7.0); 1.19 (s, 6H); 1.65 (m, 4H); 1.79 (m, 2H); 2.85 (m, 2H); 3.42 (m, 1H); 3.56 (m, 1H).

f. Synthesis of 3,3-dimethyl-1-[2-(6-phenylhexanoyl)-perhydropyridazinyl]pentane-1,2-dione To a solution of 5-phenylvalaric acid (0.2 g, 1.1 mmol) in 3 ml CH$_2$Cl$_2$ was added triethylamine (0.15 ml, 1.1 mmol), followed by isobutyl chloroformate (0.15 g, 1.1 mmol) at 0° C. After stirring for 5 minutes, a solution of 3,3-dimethyl-1-perhydropyridazinylpentane-1,2-dione (0.212 g, 1 mmol) in 1 ml CH$_2$Cl$_2$ was added. The reaction was gradually warmed up to room temperature. The crude material was subject to silica gel purification to yield final product as clear oil (0.20 g, 55%). R$_f$=0.58 (33% EtOAc/hexane). $^1$H NMR (CDCl$_3$, 400 MHz): δ 0.89 (t, 3H, J=7.5); 1.24 (s, 6H); 1.37 (m, 2H); 1.68 (m, 6H); 1.74 (m, 4H); 2.23 (m, 2H); 2.62 (t, 2H, J=7.60); 2.80 (m, 1H); 4.53 (m, 2H); 7.21 (m, 5H). Anal. Calcd. for C$_{23}$H$_{34}$N$_2$O$_3$: C, 71.47; H, 8.87; N, 7.25. Found: C, 71.54; H, 8.80; N, 7.32.

Example 5

Synthesis of 3,3-Dimethyl-1-[2-(6-(3-pyridyl)hexanoyl)-perhydropyridazinyl]-pentane-1,2-dione (Compound 13) using Scheme 2 a. Synthesis of 1-(2-hex-5-ynoylperhydropyridazinyl)-3,3-dimethylpentane-1,2-dione To a solution of 5-hexynoic acid (0.467 g, 4 mmol) in 10 ml CH$_2$Cl$_2$ was added triethylamine (0.56 ml, 4 mmol), followed by isobutyl chloroformate (0.53 ml, 4 mmol) at 0° C. After stirring for 5 minutes, a solution of 3,3-dimethyl-1-perhydropyridazinyl pentane-1,2-dione (0.424 g, 2 mmol) in 1 ml CH$_2$Cl$_2$ was added. The reaction was gradually warmed up to room temperature. The crude material was subject to silica gel purification to yield final product as clear oil (0.385 g, 63%). $^1$H NMR (CDCl$_3$, 400 MHz): δ 0.91 (t, 3H, J=7.0); 1.26 (s, 6H); 1.76(m, 8H); 2.28 (m, 2H); 2.50 (m, 2H); 2.88 (m, 2H); 3.60 (m, 1H); 4.50 (m, 2H).

b. Synthesis of 3,3-dimethyl-1-[2-(6-(3-pyridyl)hex-5-ynoyl)perhydropyridazinyl] pentane-1,2-dione To a solution of 1-(2-hex-5-ynoylperhydropyridazinyl)-3,3-dimethylpentane-1,2-dione (0.384 g, 1.25 mmol) in 10 ml CH$_2$Cl$_2$ under nitrogen was added 3-iodopyridine (0.283 g, 1.38 mmol), (Ph$_3$P)$_2$PdCl$_2$ (0.044 g, 0.06 mmol), CuI (0.0024 g, 0.013 mmol) and triethylamine(0.3 ml, 2 mmol). The reaction mixture was stirred 30 minutes at room temperature and then refluxed overnight. The mixture was concentrated and purified by silica gel column, eluting with 30% ethyl acetate in hexane, to yield product as light yellow oil (0.31 g, 65%). $^1$H NMR (CDCl$_3$, 400 MHz): δ 0.84 (t, 3H, J=7.4); 1.21 (s, 6H); 1.70 (m, 6H); 1.96(m, 2H), 2.52 (m, 3H); 2.90 (m, 2H); 3.60 (m, 1H); 4.42(m, 2H); 7.20 (m, 1H); 7.66 (m, 1H); 8.49 (m, 1H); 8.62 (m, 1H).

c. Synthesis of 3,3-dimethyl-1-[2-(6-(3-pyridyl)-hexanoyl)perhydropyridazinyl] pentane-1,2-dione 0.1 g PtO$_2$ was added to a solution of 3,3-dimethyl-1-[2-(6-(3-pyridyl)hex-5 ynoyl)perhydropyridazinyl] pentane-1,2-dione (0.3 g, 0.8 mmol) in 20 ml dry MeOH. The mixture was under hydrogenation at room pressure (1 atm) overnight. The product was obtained as clear oil after filtering the catalyst, concentration and purifying on a silica gel (0.125 g, 41%). R$_f$=0.18 (EtOAc). $^1$H NMR (CDCl$_3$, 400 MHz): δ 0.89 (t, 3H, J=7.4); 1.24 (s, 6H); 1.38 (m, 2H); 1.66 (m, 10H)i 2.14 (m, 2H); 2.63 (m, 2H); 2.82 (m, 2H); 4.60 (m, 2H); 7.23 (m, 4H). Anal. Calcd. for C$_{22}$H$_{33}$N$_3$O$_3$: C, 68.19; H, 8.58; N, 10.84. Found: C, 68.40; H. 8.52; N, 10.62.

Example 6

Synthesis of 2-Cyclohexyl-2,5,6,7,8,8a-hexahydro-2,8a-diazaindolizine-1,3-dione using Scheme 1

To a solution of 4-phenylbutyl 2-(N-cyclohexyl-carbamoyl)perhydropyridazine carboxylate (0.53 g, 1.37 mmol) in 5 ml THF at 0° C. under nitrogen was added 1.37 ml of 1 M LHMDS in THF. The mixture was allowed to stir overnight, gradually warming up to room temperature. The mixture was concentrated and purified by silica gel column, eluting with 30% ethyl acetate in hexane, to afford product (0.27 g, 83%). R$_f$=0.32 (2:1 hexane:EtOAc). $^1$H NMR (CDCl$_3$, 400 MHz): δ 1.27(m, 3H); 1.75(m, 9H); 2.12(m, 2H); 3.50(m, 4H); 3.87(m, 1H). Anal. Calcd. for C$_{12}$H$_{19}$N$_3$O$_2$: C, 60.74; H, 8.07; N, 17.71. Found: C, 60.61; H, 8.11; N, 17.82.

Example 7

Synthesis of Compounds 1, 2, 5, 6 and 18

Compounds 1, 2, 5, 6 and 18 were synthesized by the general method illustrated in Scheme 2 and exemplified in Example 4.

1) 3,3-Dimethyl-N-[2-(5-phenylpentanoyl)tetrahydro-1H-1-pyrazolyl]-1,2-pentane-dione. R$_f$=0.25 (2:1 hexane: EtOAc). $^1$H NMR (CDCl$_3$, 300 MHz): δ 0.81-0.83 (m, 3H); 1.14 (s, 6H); 1.21 (m, 2H); 1.55-1.62 (m, 8H); 2.02 (m, 2H); 2.61 (m, 4H); 7.14-7.28 (m, 5H). Anal. Calcd. for C$_{21}$H$_{30}$N$_2$O$_3$: C, 70.36; H, 8.44; N, 7.81. Found: C, 70.10; H, 8.41; N, 7.77.

2) 3,3-Dimethyl-N-[2-(3-phenylpropanoyl)tetrahydro-1H-1-pyrazolyl]-1,2-pentanedione. R$_f$=0.60 (2:1 hexane:EtOAc). $^1$HNMR (CDCl$_3$, 300 MHz): δ 0.80-0.85 (t, 3H); 1.11-1.15 (m, 8H); 1.58-2.02 (m, 6H); 2.50-2.95 (m, 4H);

7.17-7.28 (m, 5H). Anal. Calcd. for $C_{19}H_{26}N_2O_3$: C, 69.06; H, 7.93; N, 8.48. Found: C, 68.98; H, 7.90; N, 8.41.

5) 3,3-Dimethyl-1-[2-(4-phenylbutanoyl)pyrazolidinyl]-pentane-1,2-dione. $R_f$=0.5 (Hexane:EtAc 1:1). $^1$H NMR (CDCl$_3$, 400 MHz): δ 0.87 (t, 3H, J=7.5); 1.22 (s, 3H); 1.26 (s, 3H); 1.64 (m, 2H); 1.92-2.07 (m, 5H), 2.20 (m, 1H), 2.63 (m, 2H); 3.25 (m, 2H); 3.80 (m, 2H); 7.27 (m, 1H, aromatic). Anal. Calcd. for $C_{20}H_{28}N_2O_3$: C, 69.05 (69.02); H, 8.27 (8.22); N, 8.06 (8.05).

6) 3,3-Dimethyl-1-[2-(6-phenylhexanoyl)pyrazolidinyl]-pentane-1,2-dione. $R_f$=0.5 (Hexane:EtAc 1:1). $^1$H NMR (CDCl$_3$, 400 MHz): δ 0.87 (t, 3H, J=7.5); 1.22 (s, 3H); 1.26 (s, 3H), 1.35 (m, 2H); 1.59 (m, 6H); 2.07 (m, 2H), 2.20 (m, 1H), 2.60 (m, 3H); 3.25 (m, 2H); 3.70 (m, 2H); 7.26 (m, 5H, aromatic). Anal. Calcd. for $C_{24}H_{32}N_2O_3$: C, 70.65 (70.94); H, 8.70 (8.66); N, 7.36 (7.52).

18) 3,3-Dimethyl-1-[2-({5-phenyl}pentanoyl)perhydro-pyridazinyl]pentane-1,2-dione. $R_f$=0.53 (33% EtOAc/hexane). $^1$H NMR (CDCl$_3$, 400 MHz): δ 0.90 (t, 3H, J=7.44); 1.24 (s, 6H); 1.64 (m, 8H); 2.28 (m, 2H); 2.65 (m, 2H); 2.80 (m, 2H); 3.12 (m, 1H); 3.58 (m, 1H); 4.54 (m,2H); 7.22 (m, 5H). Anal. Calcd. for $C_{22}H_{32}N_2O_3$: C, 70.94; H, 8.66; N, 7.52. Found: C, 71.07; H. 8.59; N, 7.51.

Example 8

Synthesis of Compounds 3, 4 and 7

Compounds 3, 4 and 7 were synthesized by the general method illustrated in Scheme 2 and exemplified by Example 5.

3) 3,3-Dimethyl-1-[2-(5-(3-pyridyl)pent-4-ynoyl)-pyrazolidinyl]pentane-1,2-dione. $R_f$=0.2 (EtOAc). $^1$H NMR (CDCl$_3$, 400 MHz): δ 0.87 (t, 3H, J=7.5); 1.22 (s, 3H); 1.26 (s, 3H); 1.63 (m, 2H); 2.1 (m, 2H); 2.73 (m, 4H); 3.20-3.85 (m, 4H); 7.19 (m, 1H); 7.66 (m, 1H); 8.5 (m, 2H). Anal. Calcd. for $C_{20}H_{25}N_3O_3$: C, 67.67 (64.58), H: 6.91 (7.09), N: 10.63 (10.82).

4) 3,3-Dimethyl-1-[2-(5-(cyano)pent-4-ynoyl)pyrazolidinyl]-pentane-1,2-dione. $R_f$=0.45 (EtAc). $^1$H NMR (CDCl$_3$, 400 MHz): δ 0.87 (t, J=7.5); 0.90 (m, 2H); 1.22 (s, 3H); 1.26 (s, 3H); 1.64 (m, 2H); 2.03-2.20 (m, 3H), 2.52 (m, 2H), 2.63 (m, 1H); 3.69 (m, 3H). Anal. Calcd. for $C_{15}H_{22}N_2O_3$: C, 64.55 (64.73); H, 7.98 (7.97); N, 9.98 (10.06).

7) 3,3-Dimethyl-1-[2-(5-(3-pyridyl)pentanoyl)-pyrazolidinyl]pentane-1,2-dione. $R_f$=0.3 (EtAc). $^1$H NMR (CDCl$_3$, 400 MHz): δ 0.87 (t, 3H, J=7.5); 1.22 (s, 3H); 1.26 (s, 3H); 1.37 (m, 2H); 1.65 (m, 6H); 2.1 (m, 2H); 2.30 (m, 1H); 2.62 (m, 3H); 3.20-3.85 (m, 4H); 7.19 (m, 1H); 7.66 (m, 1H); 8.5 (m, 2H). Anal. Calcd. for $C_{20}H_{29}N_3O_3$: C, 65.74 (65.98); H, 8.06 (8.20); N, 11.09 (10.89).

Example 9

Synthesis of Compounds 8-10, 11, 14, 16 and 17

Compounds 8-10, 13, 16, 18 and 21 were synthesized by the general method illustrated in Scheme 1 and exemplified in Example 1.

8) 3-Phenylpropyl 2-(3,3-dimethyl-2-oxopentanoyl)-pyrazolidinecarboxylate. $R_f$=0.4 (25% EtOAc/Hexane). $^1$H NMR (CDCl$_3$, 400 MHz): δ 0.86 (t, 3H, J=7.4); 1.22 (s, 6H); 1.66 (t, 2H, J=7.5); 2.00-2.12 (m, 4H), 2.72 (t, 2H, J=7.4); 3.60 (br s, 4H); 4.18 (t, 2H, J=6.5); 7.18-7.31 (m, 5H). Anal. Calcd. for $C_{20}H_{28}N_2O_4$: C, 66.64; H, 7.83; N, 7.77. Found: C, 66.73; H. 7.81; N, 7.72.

9) 3-(3-Pyridyl)propyl 2-(3,3-dimethyl-2-oxopentanoyl)-pyrazolidinecarboxylate. $R_f$=0.1 (100% EtOAc). $^1$H NMR (CDCl$_3$, 400 MHz): δ 0.85 (t, 3H, J=7.5); 1.21 (s, 6H); 1.67 (t, 2H, J=7.5); 2.00-2.13 (m, 4H); 2.72 (t, 2H, J=7.5); 3.62 (br s, 4H); 4.19 (t, 2H, J=6.4); 7.28 (br s, 1H), 7.54 (d, 1H, J=7.7); 8.48 (s, 2H). Anal. Calcd. for $C_{19}H_{27}N_3O_4$·0.35 H$_2$O: C, 62.06; H, 7.59; N, 11.43. Found: C, 61.77; H, 7.53; N, 11.36.

10) 4-Phenylbutyl 2-(3,3-dimethyl-2-oxopentanoyl)-pyrazolidinecarboxylate. $R_f$=0.6 (25% EtOAc/Hexane). $^1$H NMR (CDCl$_3$, 400 MHz): δ 0.83 (t, 3H, J=7.5); 1.19 (s, 6H); 1.67 (t, 2H, J=7.5); 1.60-1.69 (m, 4H); 2.07 (t, 2H, J=7.4); 2.62 (t, 2H, J=6.4); 3.60 (br s, 4H); 4.13 (t, 2H, J=6.1); 7.28-7.15 (m, 5H). Anal. Calcd. for $C_{21}H_{30}N_2O_4$: C, 67.35; H, 8.07; N, 7.48. Found: C, 67.54; H, 8.31; N, 7.40.

11) 2-Phenylethyl 2-(3,3-dimethyl-2-oxopentanoyl)-pyrazolidinecarboxylate. $R_f$=0.5 (25% EtOAc/Hexane). $^1$H NMR (CDCl$_3$, 400 MHz): δ 0.83 (t, 3H, J=7.5); 1.18 (s, 6H); 1.63 (m, 2H); 1.99 (m, 2H); 2.97 (t, 2H, J=7.1); 3.60 (br s, 4H); 4.35 (t, 2H, J=6.6); 7.19-7.30 (m, 5H). Anal. Calcd. for $C_{17}H_{26}N_2O_4$: C, 65.88; H, 7.56; N, 8.09. Found: C, 65.82; H, 7.51; N, 8.02.

14) 3-phenylpropyl 2-(3,3-dimethyl-2-oxopentanoyl)-perhydropyridazinecarboxylate. $R_f$=0.73 (2:1 hexane:EtOAc). $^1$H NMR (CDCl$_3$, 400 MHz): 0.82 (t, 3H, J=7.4); 1.16 (s, 3H); 1.22 (s, 3H); 1.67 (m, 6H); 2.00 (m, 2H); 2.69 (t, 2H, J=7.9); 2.86 (m, 1H); 3.23 (m, 1H); 4.00 (m, 1H); 4.20 (m, 2H); 4.37 (m, 1H); 7.23 (m, 5H). Anal. Calcd. for $C_{21}H_{30}N_2O_4$: C, 67.35; H, 8.07; N, 7.48. Found: C, 67.51; H, 8.11; N, 7.39.

16) 5-Phenylpentyl 2-(3,3-dimethyl-2-oxopentanoyl)-perhydropyridazinecarboxylate. $R_f$=0.74 (2:1 hexane:EtOAc). $^1$H NMR (CDCl$_3$, 400 MHz): δ 0.82 (t, 3H, J=7.4); 1.14 (s, 3H); 1.21 (s, 3H); 1.38 (m, 2H); 1.65 (m, 10H); 2.62 (t, 2H, J=7.6); 2.83 (m, 1H); 3.20 (m, 1H); 3.98 (m, 1H); 4.15 (m, 2H); 4.33 (m, 1H); 7.23 (m, 5H). Anal. Calcd. for $C_{23}H_{34}N_2O_4$: C, 68.63; H, 8.51; N, 6.96. Found: C, 68.70; H, 8.47; N, 7.08.

17) 4-(3-Pyridyl)butyl 2-(3,3-dimethy-2-oxopentanoyl)-perhydropyridazinecarboxylate. $R_f$=0.45 (100% EtOAc). $^1$H NMR (CDCl$_3$, 400 MHz): δ 0.81 (t, 3H, J=7.5); 1.14 (s, 3H); 1.20 (s, 3H); 1.70 (m, 10H); 2.66 (m, 2H); 2.86 (m, 1H); 3.20 (m, 1H); 4.00 (m, 1H); 4.18 (m, 2H); 4.36 (m, 1H); 7.22 (m, 1H); 7.50 (m, 1H); 8.45 (m, 2H). Anal. Calcd. for $C_{21}H_{31}N_3O_4$·0.14 H$_2$O: C, 64.34; H. 8.04; N, 10.72. Found: C, 64.34; H, 8.02; N, 10.83.

Example 10

Synthesis of Compound 105

Compound 105 was synthesized by the general method illustrated in Scheme 1 and exemplified in Example 2.

3-Phenylpropyl 2-[benzylsulfonyl]pyrazolidine-carboxylate. $R_f$=0.5 (40% EtOAc/Hexane). $^1$H NMR (CDCl$_3$, 400 MHz): δ 2.01-2.17 (m, 4H); 2.72 (t, 2H, J=7.8); 3.68 (br s, 4H); 4.23 (t, 2H, J=6.6); 4.51 (s, 2H); 7.17-7.50 (m, 10H). Anal. Calcd. for $C_{20}H_{24}N_2SO_4$: C, 61.83; H, 6.23; N, 7.21; S, 8.25. Found: C, 61.63; H, 6.21; N, 7.05; S, 8.07.

Example 11

Synthesis of Compound 153

Compound 153 was synthesized by the general method illustrated in Scheme 1 and exemplified in Example 3.

3-Phenylpropyl 2-(N-cyclohexylcarbamoyl)pyrazolidinecarboxylate. $R_f$=0.5 (60% EtOAc/Hexane). $^1$H NMR (CDCl$_3$, 400 MHz): δ 1.09-2.00 (m, 15H); 2.69 (t, 2H, J=7.8); 3.70 (br s, 4H); 4.18 (t, 2H, J=6.4); 5.46 (d, 1H, J=8.2); 7.16-7.30 (m, 5H). Anal. Calcd. for $C_{20}H_{29}N_3O_3$: C, 66.83; H. 8.13; N, 11.69. Found: C, 66.73; H, 8.28; N, 11.59.

Example 12

$K_i$ Test

Inhibition of the peptidyl-prolyl isomerase (rotamase) activity of the inventive compounds can be evaluated by known methods described in the literature (Harding et al., *Nature*, 1989, 341:758-760; Holt et al. *J. Am. Chem. Soc.*, 115:9923-9938). These values are obtained as apparent $K_i$'s and are presented for representative compounds in Table V. The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent $K_i$ values.

In a plastic cuvette are added 950 mL of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 seconds using a spectrophotometer and the rate constants are determined from the absorbance versus time data files.

The results of these experiments are presented in TABLE V under the column "Ki".

Example 13

MPTP Model of Parkinson's Disease

The neurotrophic and neuroregenerative effects of the inventive compounds were demonstrated in an animal model of neurodegenerative disease. MPTP lesioning of dopaminergic neurons in mice was used as an animal model of Parkinson's Disease. Four week old male CD1 white mice were dosed i.p. with 30 mg/kg of MPTP for 5 days. Test compounds (4 or 10 mg/kg) or vehicle, were administered s.c. along with the MPTP for 5 days, as well as for an additional 5 days following cessation of MPTP treatment. At 18 days following MPTP treatment, the animals were sacrificed and the striata were dissected and homogenized. Immunostaining was performed on saggital and coronal brain sections using anti-tyrosine hydroxylase 1 g to quantitate survival and recovery of dopaminergic neurons. In animals treated with MPTP and vehicle, a substantial loss of functional dopaminergic terminals was observed as compared to non-lesioned animals. Lesioned animals receiving test compounds showed a significant recovery of TH-stained dopaminergic neurons.

The results of these experiments are presented in TABLE V under the column "% TH recovery".

TABLE V

| No. | Structure | Ki nM | % TH recov 4 mg/kg s.c. | % TH recov 10 mg/kg p.o. |
|---|---|---|---|---|
| 1 | 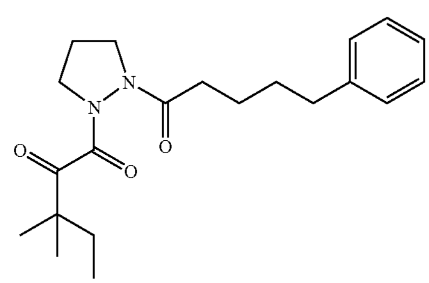 | 1175 | 14 | |
| 2 | 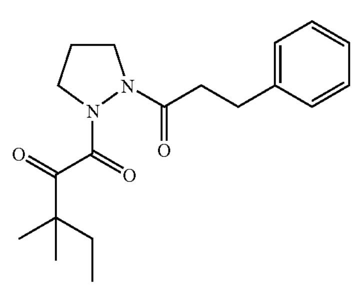 | | | 10 |

TABLE V-continued

| No. | Structure | Ki nM | % TH recov 4 mg/kg s.c. | % TH recov 10 mg/kg p.o. |
|---|---|---|---|---|
| 3 | 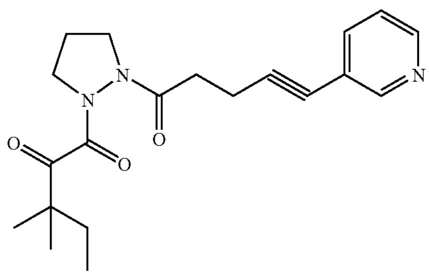 | | | 26 |
| 5 | 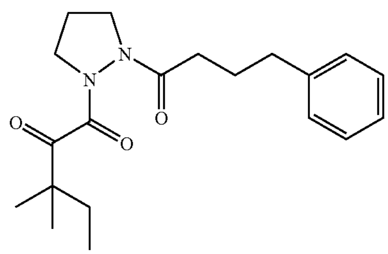 | | | 4 |
| 6 | 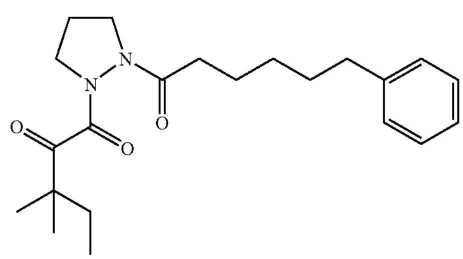 | | | 32 |
| 7 | 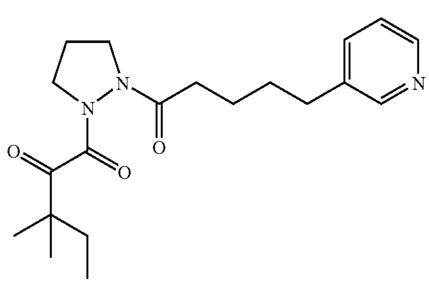 | | | 57 |
| 12 | 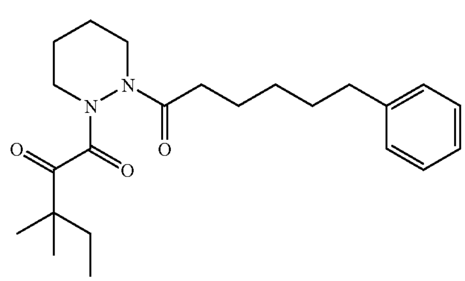 | | | 35 |

TABLE V-continued

| No. | Structure | Ki nM | % TH recov 4 mg/kg s.c. | % TH recov 10 mg/kg p.o. |
|-----|-----------|-------|-------------------------|--------------------------|
| 13  | 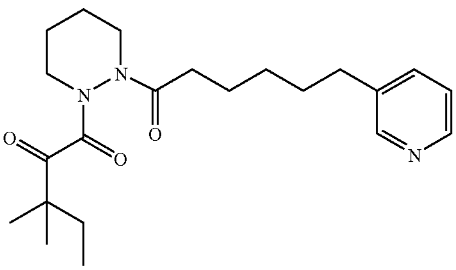          | 3208  |                         | 18                       |
| 14  | 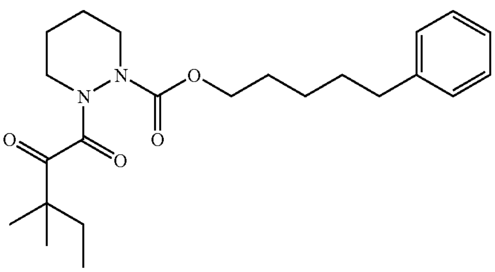          |       |                         | 3                        |
| 15  | 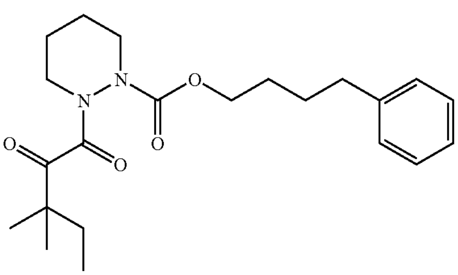          |       |                         | 21                       |
| 16  | 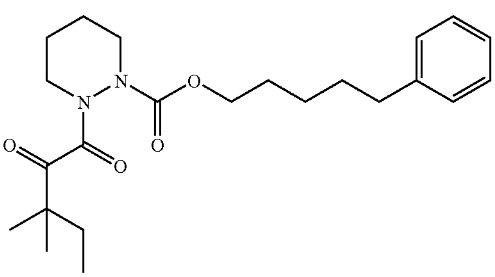          |       |                         | 49                       |
| 17  | 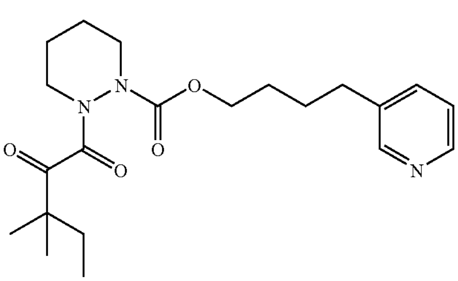          |       |                         | 38                       |

TABLE V-continued

| No. | Structure | Ki nM | % TH recov 4 mg/kg s.c. | % TH recov 10 mg/kg p.o. |
|---|---|---|---|---|
| 18 | 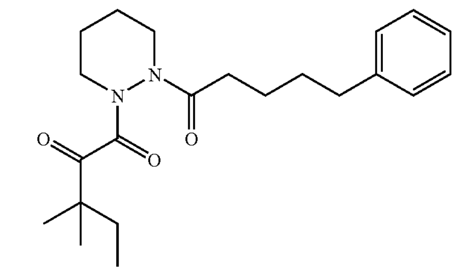 | | | 18 |
| 106 | 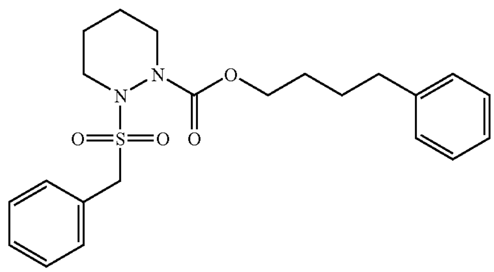 | | | 23 |
| 154 | 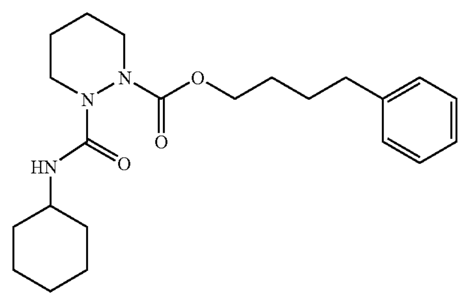 | | | 46 |

Example 14

A patient is suffering from a disease, disorder or condition described above. The patient may then be administered an effective amount of a compound of the present invention. It is expected that after such treatment, the patient would not suffer any significant injury due to, would be protected from further injury due to, or would recover from the disease, disorder or condition.

The invention being thus described, it will be obvious that the same may be varied in many ways. Such variations are not to be regarded as a departure from the spirit and scope of the invention and all such modifications are intended to be included within the scope of the following claims.

We claim:
1. A compound of formula I

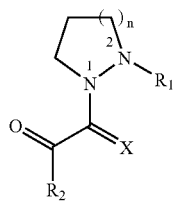

I or a pharmaceutically acceptable salt or ester thereof, wherein:

n=1-3;

$R_1$ is selected from the group consisting of —$C(R_3)_3$, —$COOR_3$, —$COR_3$, —COOH, —$SO_3H$, —$SO_2HNR_3$, —$PO_2(R_3)_2$, —CN, —$PO_3(R_3)_2$, —$OR_3$, —$SR_3$, —$NHCOR_3$, —$N(R_3)_2$, —$CON(R_3)_2$, —CONH(O)$R_3$, —CONHNHSO$_2R_3$, —COHNSO$_2R_3$, and —CONR$_3$CN;

$R_2$ is selected from the group consisting of hydrogen, $C_1$-$C_9$ straight or branched chain alkyl, $C_2$-$C_9$ straight or branched chain alkenyl, $C_2$-$C_9$ straight or branched chain alkynyl, aryl, heteroaryl, carbocycle, and heterocycle, wherein said alkyl, alkenyl, alkynyl, aryl, heteroaryl, carbocycle, and heterocycle is unsubstituted or substituted with one or more substituents selected from $R_3$;

R3 is selected from the group consisting of hydrogen, $C_1$-$C_9$ alkyl, $C_2$-$C_9$ straight or branched chain alkenyl, $C_2$-$C_9$ straight or branched chain alkynyl, $C_1$-$C_9$ alkoxy, $C_2$-$C_9$ alkenyloxy, aryloxy, phenoxy, benzyloxy, hydroxy, carboxy, ($C_1$-$C_9$ thioalkyl, $C_2$-$C_9$ thioalkenyl, $C_1$-$C_9$ alkylamino, $C_2$-$C_9$ alkenylamino, cyano, nitro, imino, sulfonyl, sulfhydryl, halo, haloalkyl, trifluoromethyl, aryl, heteroaryl, carbocycle, and heterocycle,
wherein said alkyl, alkenyl, alkynyl, alkoxy, alkenyloxy, aryloxy, thioalkyl, thioalkenyl, alkylamino, alkenylamino, aryl, heteroaryl, carbocycle, or heterocycle group is optionally substituted with a hydroxy, carboxy, cyano, nitro, imino, sulfonyl, thiocarbonyl, sulfhydryl, halo, haloalkyl, trifluoromethyl, aryl, heteroaryl, carbocyle, or heterocycle group; and
X is O or S,
wherein the heteroaryl, carbocycle, and heterocycle are selected from cyclopentyl, cyclohexyl, cycloheptyl, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphihyridinyl, pteridinyl, carbazolyl, acridinyl, phenazinyl, phenothiazinyl, phenoxazinyl, adamantly, pyrrole groups, thiophene groups, pyridine groups, and isoxazole groups.

2. The compound of claim 1, wherein the compound is non-immunosuppressive.

3. The compound of claim 1, wherein said compound is selected from the group consisting of:

3,3-dimethyl-N-[2-(5-phenylpentanoyl)-tetrahydro-1H-1-pyrazolyl]-1,2-pentanedione;

3,3-dimethyl-N-[2-(3-phenylpropanoyl)-tetrahydro-1H-1-pyrazolyl]-1,2-pentanedione;

3,3-dimethyl-1-[2-(5-(3-pyridyl) pent-4-ynoyl)-pyrazolidinyl]pentane-1,2-dione;

3,3-dimethyl-1-[2-(5 -(cyano) pent-4-ynoyl)pyrazolidinyl]-pentane-1,2-dione;

3,3-dimethyl-1-[2-(4-phenylbutanoyl) pyrazolidinyl]-pentane-1,2-dione;

3,3-dimethyl-1-[2-(6-phenylhexanoyl) pyrazolidinyl]-pentane-1,2-dione;

3,3-dimethyl-1-[2-(5-(3-pyridyl) pentanoyl)-pyrazolidinyl] pentane-1,2-dione;

3-phenyipropyl 2-(3,3-dimethyl-2-oxopentanoyl)-pyrazolidinecarboxylate;

3-(3-pyridyl) propyl 2-(3,3-dimethyl-2-oxopentanoyl) pyrazolidinecarboxylate;

4-phenylbutyl 2-(3,3-dimethyl-2-oxopentanoyl)-pyrazolidinecarboxylate;

2-phenylethyl 2-(3,3-dimethyl-2-oxopentanoyl)-pyrazolidinecarboxylate;

3,3-dimethyl-1-[2-(6-phenylhexanoyl) perhydro-pyridazinyl]pentane-1,2-dione;

3,3-dimethyl-1-[2-(6-(3-pyridyl) hexanoyl)-perhydropyridazinyl] pentane-1,2-dione;

3-phenyipropyl 2-(3,3 -dimethyl-2-oxopentanoyl)perhydropyridazinecarboxylate;

4-phenylbutyl 2-(3,3-dimethyl-2-oxopentanoyl)-perhydropyridazinecarboxylate;

5-phenylpentyl 2-(3,3-dimethyl-2-oxopentanoyl)-perhydropyridazinecarboxylate;

4-(3-pyridyl) butyl 2-(3,3-dimethyl-2-oxopentanoyl)-perhydropyridazinecarboxylate;

3,3-dimethyl-1-[2-((5-phenyl) pentanoyl) perhydropyridazinyl] pentane-1,2-dione; and a pharmaceutically acceptable salt or ester thereof.

4. A pharmaceutical composition comprising:
(i) a therapeutically effective amount of a compound of formula I:

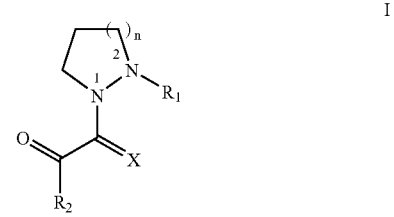

or a pharmaceutically acceptable salt or ester thereof, wherein:

n=1-3;

$R_1$ is selected from the group consisting of —$C(R_3)_3$, —$COOR_3$, —$COR_3$, —COOH, —$SO_3H$, —$SO_2HNR_3$, —$PO_2(R_3)_2$, —CN, —$PO_3(R_3)_2$, —$OR_3$, —$SR_3$, —$NHCOR_3$, —$N(R_3)_2$, —$CON(R_3)_2$, —$CONH(O)R_3$, —$CONHNSO_2R_3$, —$COHNSO_2R_3$, and —$CONR_3CN$;

$R_2$ is selected from the group consisting of hydrogen, $C_1$-$C_9$ straight or branched chain alkyl, $C_{12}$-$C_{19}$ straight or branched chain alkenyl, $C_{12}$-$C_{19}$ straight or branched chain alkynyl, aryl, heteroaryl, carbocycle, and heterocycle, wherein said alkyl, alkenyl, alkynyl, aryl, heteroaryl, carbocycle, and heterocycle is unsubstituted or substituted with one or more substituents selected from $R_3$;

$R_3$ is selected from the group consisting of hydrogen, $C_1$-$C_9$ alkyl, $C_2$-$C_9$ straight or branched chain alkenyl, $C_2$-$C_9$ straight or branched chain alkynyl, $C_1$-$C_9$ alkoxy, $C_2$-$C_9$ alkenyloxy, aryloxy, phenoxy, benzyloxy, hydroxy, carboxy, $C_1$-$C_9$ thioalkyl, $C_2$-$C_9$ thioalkenyl, $C_1$-$C_9$ alkylamino, $C_2$-$C_9$ alkenylamino, cyano, nitro, imino, sulfonyl, sulfhydryl, halo, haloalkyl, trifluoromethyl, aryl, heteroaryl, carbocycle, and heterocycle, wherein said alkyl, alkenyl, alkynyl, alkoxy, alkenyloxy, aryloxy, thioalkyl, thioalkenyl, alkylamino, alkenylamino, aryl, heteroaryl, carbocycle, or heterocycle group is optionally substituted with a hydroxy, carboxy, cyano, nitro, imino, sulfonyl, sulfhydryl, halo, haloalkyl, trifluoromethyl, aryl, heteroaryl, carbocyle, or heterocycle group; and X is O or S; and (ii) a pharmaceutically acceptable carrier, wherein the heteroaryl, carbocycle, and heterocycle are selected from cyclopentyl, cyclohexyl, cycloheptyl, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, adamantly, pyrrole groups, thiophene groups, pyridine groups, and isoxazole groups.

5. A method for treating peripheral neuropathy or Parkinson's disease in a mammal, comprising administering to the mammal an effective amount of a compound of formula I:

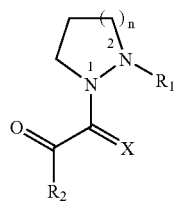

I or a pharmaceutically acceptable salt or ester thereof, wherein:

$n=1-3$;

$R_1$ is selected from the group consisting of —$C(R_3)_3$, —$COOR_3$, —$COR_3$, —COOH, —$SO_3H$, —$SO_2HNR_3$, —$PO_2(R_3)_2$, —CN, —$PO_3(R_3)_2$, —$OR_3$, —$SR_3$, —$NHCOR_3$, —$N(R_3)_2$, —$CON(R_3)_2$, —$CONH(O)R_3$, —$CONHNSO_2R_3$, —$COHNSO_2R_3$, and —$CONR_3CN$;

$R_2$ is selected from the group consisting of hydrogen, $C_1$-$C_9$ straight or branched chain alkyl, $C_2$-$C_9$ straight or branched chain alkenyl, $C_2$-$C_9$ straight or branched chain alkynyl, aryl, heteroaryl, carbocycle, and heterocycle, wherein said alkyl, alkenyl, alkynyl, aryl, heteroaryl, carbocycle, and heterocycle is unsubstituted or substituted with one or more substituents selected from $R_3$;

$R_3$ is selected from the group consisting of hydrogen, $C_1$-$C_9$ alkyl, $C_2$-$C_9$ straight or branched chain alkenyl, $C_2$-$C_9$ straight or branched chain alkynyl, $C_1$-$C_9$ alkoxy, $C_2$-$C_9$ alkenyloxy, aryloxy, phenoxy, benzyloxy, hydroxy, carboxy, $C_1$-$C_9$ thioalkyl, $C_2$-$C_9$ thioalkenyl, $C_1$-$C_9$ alkylamino, $C_2$-$C_9$ alkenylamino, cyano, nitro, imino, sulfonyl, suithydryl, halo, haloalkyl, trifluoromethyl, aryl, heteroaryl, carbocycle, and heterocycle, wherein said alkyl, alkenyl, alkynyl, alkoxy, alkenyloxy, aryloxy, thioalkyl, thioalkenyl, alkylamino, alkenylamino, aryl, heteroaryl, carbocycle, or heterocycle group is optionally substituted with a hydroxy, carboxy, cyano, nitro, imino, sulfonyl, sulfhydryl, halo, haloalkyl, trifluoromethyl, aryl, heteroaryl, carbocyle, or heterocycle group; and X is O or S, wherein the heteroaryl, carbocycle, and heterocycle are selected from cyclopentyl, cyclohexyl, cycloheptyl, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, adamantly, pyrrole groups, thiophene groups, pyridine groups, and isoxazole groups.

6. The method of claim 5, wherein the method is for treating peripheral neuropathy.

7. The method of claim 6, wherein the peripheral neuropathy is caused by physical injury or disease state.

8. The method of claim 5, wherein the method is for treating Parkinson's disease.

9. A method of making a pharmaceutical composition, comprising adding together a pharmaceutically acceptable carrier and a compound of claim 1.

* * * * *